US008592566B2

(12) United States Patent
Iwamura et al.

(10) Patent No.: US 8,592,566 B2
(45) Date of Patent: Nov. 26, 2013

(54) IMMUNOSTIMULATORY OLIGONUCLEOTIDES AND USE THEREOF IN PHARMACEUTICALS

(75) Inventors: Tomokatsu Iwamura, Kanagawa (JP); Hideki Narumi, Kanagawa (JP); Hajime Masumoto, Kanagawa (JP); Akihito Kaneda, Kanagawa (JP); Akiko Soneda, Kanagawa (JP); Shizuo Akira, Osaka (JP)

(73) Assignees: Toray Industries, Inc., Tokyo (JP); Osaka University, Suita-Shi (JP)

( * ) Notice: Subject to any disclaimer, the term of this patent is extended or adjusted under 35 U.S.C. 154(b) by 780 days.

(21) Appl. No.: 12/301,746

(22) PCT Filed: May 31, 2007

(86) PCT No.: PCT/JP2007/061105
§ 371 (c)(1),
(2), (4) Date: Nov. 20, 2008

(87) PCT Pub. No.: WO2007/139190
PCT Pub. Date: Dec. 6, 2007

(65) Prior Publication Data
US 2009/0263413 A1    Oct. 22, 2009

(30) Foreign Application Priority Data

May 31, 2006 (JP) ................. 2006-152544
Feb. 27, 2007 (JP) ................. 2007-046556

(51) Int. Cl.
*A61K 31/711* (2006.01)
*A61K 31/7125* (2006.01)
*A61K 39/29* (2006.01)
*A61K 39/35* (2006.01)

(52) U.S. Cl.
USPC .................. 536/22.1; 514/45; 424/189.1

(58) Field of Classification Search
None
See application file for complete search history.

(56) References Cited

U.S. PATENT DOCUMENTS

| | | | |
|---|---|---|---|
| 6,194,388 B1 | 2/2001 | Krieg et al. | |
| 6,207,646 B1 | 3/2001 | Krieg et al. | |
| 6,239,116 B1 | 5/2001 | Krieg et al. | |
| 6,498,148 B1 | 12/2002 | Raz | |
| 6,949,520 B1 | 9/2005 | Hartmann et al. | |
| 7,585,847 B2 * | 9/2009 | Bratzler et al. | 514/44 R |
| 7,718,623 B2 * | 5/2010 | Kitagawa et al. | 514/44 R |
| 7,960,356 B2 * | 6/2011 | Klinman et al. | 514/44 R |
| 2002/0098199 A1 | 7/2002 | Van Nest et al. | |
| 2003/0216340 A1 | 11/2003 | Van Nest et al. | |
| 2004/0067902 A9 * | 4/2004 | Bratzler et al. | 514/44 |
| 2004/0198685 A1 * | 10/2004 | Agrawal et al. | 514/44 |
| 2005/0169888 A1 | 8/2005 | Hartmann et al. | |
| 2005/0209184 A1 * | 9/2005 | Klinman et al. | 514/44 |
| 2006/0003962 A1 | 1/2006 | Ahluwalia et al. | |
| 2006/0246035 A1 | 11/2006 | Ahluwalia et al. | |
| 2007/0078104 A1 | 4/2007 | Krieg et al. | |
| 2007/0179101 A1 | 8/2007 | Kitagawa et al. | |

FOREIGN PATENT DOCUMENTS

| | | |
|---|---|---|
| EP | 0 468 520 A3 | 1/1992 |
| JP | 4-352724 A | 12/1992 |
| JP | 10-506265 A | 6/1998 |
| JP | 2001-503267 A | 3/2001 |
| JP | 2002-500159 A | 1/2002 |
| JP | 2002-517156 A | 6/2002 |
| JP | 2003-510290 A | 3/2003 |
| JP | 2003-526662 A | 9/2003 |
| JP | 2003-286174 A | 10/2003 |
| JP | 2005-237328 A | 9/2005 |
| JP | 2006-515277 A | 5/2006 |
| JP | 2008-000001 A | 1/2008 |
| KR | 1020010063153 A | 7/2001 |
| WO | WO-96/02555 A1 | 2/1996 |
| WO | WO 97/28259 * | 8/1997 |
| WO | WO-98/18810 A1 | 5/1998 |
| WO | WO-98/55495 A2 | 12/1998 |
| WO | WO-99/11275 A2 | 3/1999 |
| WO | WO-00/61151 A2 | 10/2000 |

(Continued)

OTHER PUBLICATIONS

Yamamoto S et al. "In vitro augmentation of natural killer cell activity and production of interferon-alpha/beta and -gamma with deoxyribonucleic acid fraction from *Mycobacterium bovis* BCG." Jul. 1988, Jpn J Cancer Res. 79(7): p. 866-73.

(Continued)

*Primary Examiner* — Bao Li
(74) *Attorney, Agent, or Firm* — Birch, Stewart, Kolasch & Birch, LLP

(57) ABSTRACT

A novel immunostimulatory oligonucleotide by which an IFN-inducing activity is enhanced and an inflammatory cytokine-inducing activity is reduced, and a pharmaceutical containing the same, and an application thereof are provided. That is, the present invention provides the immunostimulatory oligonucleotide composed of a base sequence represented by a formula: 5'-$(G)_M$PXCGYQ$(G)_N$-3' (SEQ ID NO: 118) (X and Y are mutually independent and represent an arbitrary sequence which has a length of 0 to 10 nucleotides and does not contain 4 or more consecutive G residues, and a length of X+Y is 6 to 20 nucleotides; XCGY contains a palindrome sequence having a length of at least 8 nucleotides and has a length of 8 to 22 nucleotides; P and Q are mutually independent and represent one nucleotide other than G; M represents an integer of 6 to 10 and N represents an integer of 0 to 3 wherein a full length thereof is 16 to 37 nucleotides (except for an oligonucleotide composed of a base sequence represented by SEQ ID NO:5), the pharmaceutical application thereof.

16 Claims, 15 Drawing Sheets

(56) References Cited

FOREIGN PATENT DOCUMENTS

| WO | WO-01/68078 A2 | 9/2001 |
|---|---|---|
| WO | WO-03/015711 A2 | 2/2003 |
| WO | WO-2004/039829 A2 | 5/2004 |
| WO | WO-2004/058179 A2 | 7/2004 |
| WO | WO 2005/001055 A2 * | 1/2005 |
| WO | WO-2005/014110 A1 | 2/2005 |
| WO | WO 2005/083076 A1 * | 9/2005 |
| WO | WO-2005/083076 A1 | 9/2005 |
| WO | WO-2006/035939 A1 | 4/2006 |

OTHER PUBLICATIONS

Klinman et al. "CpG motifs present in bacterial DNA rapidly induce lymphocytes to secrete interleukin 6, interkeukin 12, and interferonγ", Apr. 1996, vol. 93, p. 2879-2883, Proc. Natl. Acad. Sci.
Yamamoto et al. "Unique Palindromic Sequences in Synthetic Oligonucleotides are required to induce INF and augment INF-mediated natural killer activity", Jun. 15, 1992, vol. 148, p. 4072-4076.
Hemmi et al. "A toll-like receptor recognized bacterial DNA" Dec. 2000, vol. 408, p. 740-745.
Bauer et al. "Human TLR9 confers responsiveness to bacterial DNA via species-specific CpG motif recognition", Jul. 31, 2001, PNAS vol. 98, No. 16, p. 9237-9242.
Tighe et al. "Conjugation of immunostimulatory DNA to the short ragweed allergen Amb a 1 enhances its immunogenicity and reduces its allergenicity", 2000,106, p. 124-34, J Allergy Clin Immunol.
Till et al. "Mechanisms of immunotherapy", 2004, 113, p. 1025-1034, J Allergy Clim Immunol.
Aman et al. "Interferon-alpha stimulates production of interkeukin-10 in activated CD4+ T cells and monocytes", 1996 87, p. 4731-4736 by American Society of Hematology.
Abe K et al. "Role of CpG ODN in concanavalin A-induced hepatitis in mice", Jun. 2005, p. 41-9, Fukushima J Med Sci. 51(1).
Iho et al. Oligodeoxynucleotides Containing Palindrome Sequences with Internal 5'-CpG-3' Act Directly on Human NK and activated T cells to Induce IFN-γ Production in Vitro., Journal of Immunology, 1999, vol. 163, No. 7, p. 3642-3652.
Bartz et al., "Poly-Gluanosine Strings Improve Cellular Uptake and Stimulatory Activity of Phosphodiester CpG Oligonucleotides in Human Leukocytes", Vaccine, vol. 23, No. 2, Nov. 2004, pp. 148-155.
Krieg, Arthur M., "CpG Motifs in Bacterial DNA and Their Immune Effects", Annual Review of Immunology, vol. 20, 2002, pp. 709-760.
Lipford et al., "Poly-LGuanosine Motifs Costimulate Antigen-Reactive CD8 T Cells While Bacterial CpG-DNA Affect T-Cell Activation Via Antigen-Presenting Cell-Derived Cytokines", Immunology, vol. 101, No. 1, Sep. 2000, pp. 46-52.
Marshall et al., "Identification of a Novel CpG DNA Class and Motif that Optimally Stimulate B Cell and Plasmacytoid Dentritic Cell Functions", J. of Leukocyte Biology, vol. 73, No. 6, Jun. 2003, pp. 781-792.
Sugauchi et al., "Vigorous Hepatitis C Virus-Specific CD4+ and CD5+ T Cell Responses induced by Protein Immunization in the Presence of Montanide ISA720 Plus Synthetic Oligodeoxynucleotides Containing Immunostimulatory Cytosine-Guanine Dinucleotide Motifs", J. of Infectious Diseases, vol. 193, No. 4, Feb. 15, 2006, pp. 563-572.
Vollmer et al., "Characterization of Three CpG Oligodeoxynucleotide Classes with Distinct Immunostimulatory Activities", Eur. J. of Immunology. vol. 34, No. 1, Jan. 2004, pp. 251-262.
Wattrang et al., "Immunostimulatory DNA Activates Production of Type I Interferons and Interleukin-6 in Equine Peripheral Blood Mononuclear Cells in Vitro", Vet. Immunology and Immunopathology, vol. 107, No. 3-4, Sep. 15, 2005, pp. 265-279.
Zimmermann et al., "Immunostimulatory DNA as Adjuvant: Efficacy of Phosphodiester CpG Oligonucleotides is Enhanced by 3' Sequence Modifications", Vaccine, vol. 21, No. 9-10, Feb. 14, 2003, pp. 990-995.
Office Action issued in Australian Patent Application No. 2007268534 on Oct. 5, 2010.

* cited by examiner

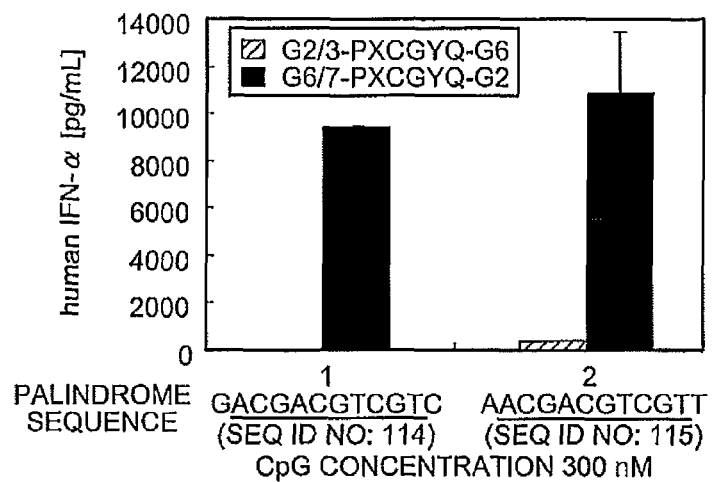
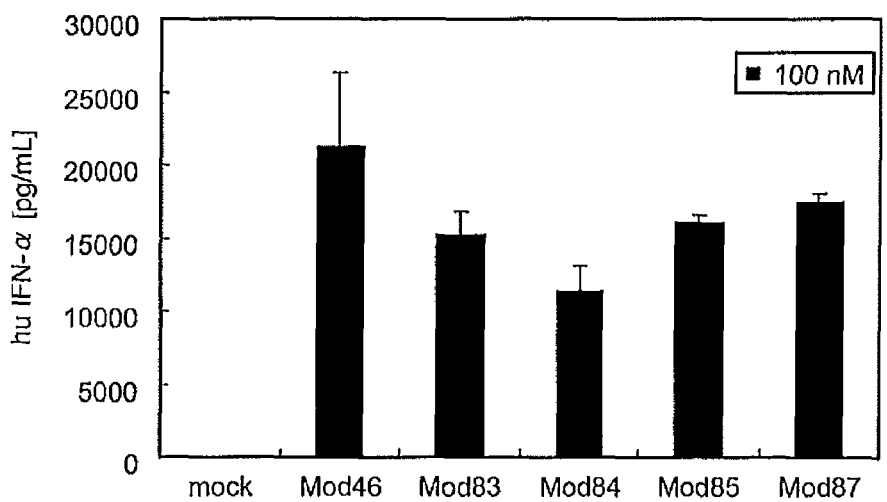

SEQUENCE LISTING

```
<160> NUMBER OF SEQ ID NOS: 118

<210> SEQ ID NO 1
<211> LENGTH: 20
<212> TYPE: DNA
<213> ORGANISM: Artificial
<220> FEATURE:
<223> OTHER INFORMATION: Mod2.  Contains palindrome sequence.

<400> SEQUENCE: 1
ggtgccgatc ggcagggggg                                                    20

<210> SEQ ID NO 2
<211> LENGTH: 18
<212> TYPE: DNA
<213> ORGANISM: Artificial
<220> FEATURE:
<223> OTHER INFORMATION: Mod52. Contains palindrome sequence.

<400> SEQUENCE: 2
gggtgccgat cggcaggg                                                      18

<210> SEQ ID NO 3
<211> LENGTH: 19
<212> TYPE: DNA
<213> ORGANISM: Artificial
<220> FEATURE:
<223> OTHER INFORMATION: Mod51. Contains palindrome sequence.

<400> SEQUENCE: 3
ggggtgccga tcggcaggg                                                     19

<210> SEQ ID NO 4
<211> LENGTH: 20
<212> TYPE: DNA
<213> ORGANISM: Artificial
<220> FEATURE:
<223> OTHER INFORMATION: Mod42. Contains palindrome sequence.

<400> SEQUENCE: 4
gggggtgccg atcggcaggg                                                    20
```

```
<210> SEQ ID NO 5
<211> LENGTH: 21
<212> TYPE: DNA
<213> ORGANISM: Artificial
<220> FEATURE:
<223> OTHER INFORMATION: Mod33. Contains palindrome sequence.

<400> SEQUENCE: 5 gggggggtgcc gatcggcagg g                                              21

<210> SEQ ID NO 6
<211> LENGTH: 22
<212> TYPE: DNA
<213> ORGANISM: Artificial
<220> FEATURE:
<223> OTHER INFORMATION: Mod53. Contains palindrome sequence.

<400> SEQUENCE: 6 ggggggggtgc cgatcggcag gg                                             22

<210> SEQ ID NO 7
<211> LENGTH: 23
<212> TYPE: DNA
<213> ORGANISM: Artificial
<220> FEATURE:
<223> OTHER INFORMATION: Mod54. Contains palindrome sequence.

<400> SEQUENCE: 7 gggggggggtg ccgatcggca ggg                                            23

<210> SEQ ID NO 8
<211> LENGTH: 19
<212> TYPE: DNA
<213> ORGANISM: Artificial
<220> FEATURE:
<223> OTHER INFORMATION: Mod56. Contains palindrome sequence.

<400> SEQUENCE: 8
gggggtgccg atcggcagg                                                  19

<210> SEQ ID NO 9
<211> LENGTH: 20
<212> TYPE: DNA
<213> ORGANISM: Artificial
<220> FEATURE:
<223> OTHER INFORMATION: Mod40. Contains palindrome sequence.

<400> SEQUENCE: 9
ggggggtgcc gatcggcagg                                                 20

<210> SEQ ID NO 10
<211> LENGTH: 21
<212> TYPE: DNA
<213> ORGANISM: Artificial
<220> FEATURE:
<223> OTHER INFORMATION: Mod55.  Contains palindrome sequence.

<400> SEQUENCE: 10 ggggggggtgc cgatcggcag g                                              21

<210> SEQ ID NO 11
<211> LENGTH: 19
<212> TYPE: DNA
<213> ORGANISM: Artificial
<220> FEATURE:
<223> OTHER INFORMATION: Mod41. Contains palindrome sequence.
```

```
<400> SEQUENCE: 11 gggggggtgcc gatcggcag                                               19

<210> SEQ ID NO 12
<211> LENGTH: 22
<212> TYPE: DNA
<213> ORGANISM: Artificial
<220> FEATURE:
<223> OTHER INFORMATION: Mod48. Contains palindrome sequence.

<400> SEQUENCE: 12 gggggggtgcc gatcggcagg gg                                           22

<210> SEQ ID NO 13
<211> LENGTH: 23
<212> TYPE: DNA
<213> ORGANISM: Artificial
<220> FEATURE:
<223> OTHER INFORMATION: Mod49. Contains palindrome sequence.

<400> SEQUENCE: 13 gggggggtgcc gatcggcagg ggg                                          23

<210> SEQ ID NO 14
<211> LENGTH: 24
<212> TYPE: DNA
<213> ORGANISM: Artificial
<220> FEATURE:
<223> OTHER INFORMATION: Mod50. Contains palindrome sequence.

<400> SEQUENCE: 14 gggggggtgcc gatcggcagg gggg                                         24

<210> SEQ ID NO 15
<211> LENGTH: 18
<212> TYPE: DNA
<213> ORGANISM: Artificial
<220> FEATURE:
<223> OTHER INFORMATION: Mod61. Contains palindrome sequence.

<400> SEQUENCE: 15 gggggggtgcc gatcggca                                                18

<210> SEQ ID NO 16
<211> LENGTH: 19
<212> TYPE: DNA
<213> ORGANISM: Artificial
<220> FEATURE:
<223> OTHER INFORMATION: Mod62. Contains palindrome sequence.

<400> SEQUENCE: 16 ggggggggtgc cgatcggca                                               19

<210> SEQ ID NO 17
<211> LENGTH: 20
<212> TYPE: DNA
<213> ORGANISM: Artificial
<220> FEATURE:
<223> OTHER INFORMATION: Mod63. Contains palindrome sequence.

<400> SEQUENCE: 17 gggggggggtg ccgatcggca                                              20

<210> SEQ ID NO 18
<211> LENGTH: 22
<212> TYPE: DNA
```

```
<213> ORGANISM: Artificial
<220> FEATURE:
<223> OTHER INFORMATION: Mod64. Contains palindrome sequence.

<400> SEQUENCE: 18
gggggggggg tgccgatcgg ca                                              22

<210> SEQ ID NO 19
<211> LENGTH: 24
<212> TYPE: DNA
<213> ORGANISM: Artificial
<220> FEATURE:
<223> OTHER INFORMATION: Mod65. Contains palindrome sequence.

<400> SEQUENCE: 19
gggggggggg ggtgccgatc ggca                                            24

<210> SEQ ID NO 20
<211> LENGTH: 32
<212> TYPE: DNA
<213> ORGANISM: Artificial
<220> FEATURE:
<223> OTHER INFORMATION: Mod66. Contains palindrome sequence.

<400> SEQUENCE: 20
gggggggggg gggggggggg tgccgatcgg ca                                   32

<210> SEQ ID NO 21
<211> LENGTH: 20
<212> TYPE: DNA
<213> ORGANISM: Artificial
<220> FEATURE:
<223> OTHER INFORMATION: Mod29. Contains palindrome sequence.

<400> SEQUENCE: 21
ggtcccgatc gggagggggg                                                 20

<210> SEQ ID NO 22
<211> LENGTH: 21
<212> TYPE: DNA
<213> ORGANISM: Artificial
<220> FEATURE:
<223> OTHER INFORMATION: Mod43. Contains palindrome sequence.

<400> SEQUENCE: 22
gggggtcccc gatcgggagg g                                               21

<210> SEQ ID NO 23
<211> LENGTH: 20
<212> TYPE: DNA
<213> ORGANISM: Artificial
<220> FEATURE:
<223> OTHER INFORMATION: Mod37. Contains palindrome sequence.

<400> SEQUENCE: 23
ggttccgatc ggaaggggggg                                                20

<210> SEQ ID NO 24
<211> LENGTH: 21
<212> TYPE: DNA
<213> ORGANISM: Artificial
<220> FEATURE:
<223> OTHER INFORMATION: Mod44. Contains palindrome sequence.

<400> SEQUENCE: 24 gggggggttcc gatcggaagg g                                              21
```

```
<210> SEQ ID NO 25
<211> LENGTH: 20
<212> TYPE: DNA
<213> ORGANISM: Artificial
<220> FEATURE:
<223> OTHER INFORMATION: Mod38. Contains palindrome sequence.

<400> SEQUENCE: 25
ggtggcgatc gccagggggg                                                  20

<210> SEQ ID NO 26
<211> LENGTH: 21
<212> TYPE: DNA
<213> ORGANISM: Artificial
<220> FEATURE:
<223> OTHER INFORMATION: Mod45. Contains palindrome sequence.

<400> SEQUENCE: 26 gggggggtggc gatcgccagg g                                               21

<210> SEQ ID NO 27
<211> LENGTH: 20
<212> TYPE: DNA
<213> ORGANISM: Artificial
<220> FEATURE:
<223> OTHER INFORMATION: Mod39. Contains palindrome sequence.

<400> SEQUENCE: 27
ggtgacgatc gtcagggggg                                                  20

<210> SEQ ID NO 28
<211> LENGTH: 21
<212> TYPE: DNA
<213> ORGANISM: Artificial
<220> FEATURE:
<223> OTHER INFORMATION: Mod46. Contains palindrome sequence.

<400> SEQUENCE: 28 gggggggtgac gatcgtcagg g                                               21

<210> SEQ ID NO 29
<211> LENGTH: 20
<212> TYPE: DNA
<213> ORGANISM: Artificial
<220> FEATURE:
<223> OTHER INFORMATION: D19. Contains palindrome sequence.

<400> SEQUENCE: 29
ggtgcatcga tgcagggggg                                                  20

<210> SEQ ID NO 30
<211> LENGTH: 21
<212> TYPE: DNA
<213> ORGANISM: Artificial
<220> FEATURE:
<223> OTHER INFORMATION: Mod47. Contains palindrome sequence.

<400> SEQUENCE: 30 gggggggtgca tcgatgcagg g                                               21

<210> SEQ ID NO 31
<211> LENGTH: 24
<212> TYPE: DNA
<213> ORGANISM: Artificial
<220> FEATURE:
<223> OTHER INFORMATION: 2006. Contains palindrome sequence.
```

-continued

<400> SEQUENCE: 31
tcgtcgtttt gtcgttttgt cgtt                                          24

<210> SEQ ID NO 32
<211> LENGTH: 22
<212> TYPE: DNA
<213> ORGANISM: Artificial
<220> FEATURE:
<223> OTHER INFORMATION: 2395. Contains palindrome sequence.

<400> SEQUENCE: 32
tcgtcgtttt cggcgcgcgc cg                                            22

<210> SEQ ID NO 33
<211> LENGTH: 22
<212> TYPE: DNA
<213> ORGANISM: Artificial
<220> FEATURE:
<223> OTHER INFORMATION: 1018. Contains palindrome sequence.

<400> SEQUENCE: 33
tgactgtgaa cgttcgagat ga                                            22

<210> SEQ ID NO 34
<211> LENGTH: 21
<212> TYPE: DNA
<213> ORGANISM: Artificial
<220> FEATURE:
<223> OTHER INFORMATION: C274. Contains palindrome sequence.

<400> SEQUENCE: 34
tcgtcgaacg ttcgagatga t                                             21

<210> SEQ ID NO 35
<211> LENGTH: 20
<212> TYPE: DNA
<213> ORGANISM: Artificial
<220> FEATURE:
<223> OTHER INFORMATION: I1. Contains palindrome sequence.

<400> SEQUENCE: 35
ggggtcaacg ttcagggggg                                               20

<210> SEQ ID NO 36
<211> LENGTH: 20
<212> TYPE: DNA
<213> ORGANISM: Artificial
<220> FEATURE:
<223> OTHER INFORMATION: G9-GACGATCGTC-G1. Contains palindrome sequence.

<400> SEQUENCE: 36
gggggggggg acgatcgtcg                                               20

<210> SEQ ID NO 37
<211> LENGTH: 20
<212> TYPE: DNA
<213> ORGANISM: Artificial
<220> FEATURE:
<223> OTHER INFORMATION: M26. Contains palindrome sequence.

<400> SEQUENCE: 37 gggggggaaaa cgttcttcgc                                              20

<210> SEQ ID NO 38
<211> LENGTH: 20
<212> TYPE: DNA

<213> ORGANISM: Artificial
<220> FEATURE:
<223> OTHER INFORMATION: M27. Contains palindrome sequence.

<400> SEQUENCE: 38 gggggggga aaacgttctt                    20

<210> SEQ ID NO 39
<211> LENGTH: 20
<212> TYPE: DNA
<213> ORGANISM: Artificial
<220> FEATURE:
<223> OTHER INFORMATION: Mod70. Contains palindrome sequence.

<400> SEQUENCE: 39
gggacgacgt cgtcggggggg                  20

<210> SEQ ID NO 40
<211> LENGTH: 20
<212> TYPE: DNA
<213> ORGANISM: Artificial
<220> FEATURE:
<223> OTHER INFORMATION: Mod71. Contains palindrome sequence.

<400> SEQUENCE: 40 ggggggacg acgtcgtcgg                    20

<210> SEQ ID NO 41
<211> LENGTH: 20
<212> TYPE: DNA
<213> ORGANISM: Artificial
<220> FEATURE:
<223> OTHER INFORMATION: Mod72. Contains palindrome sequence.

<400> SEQUENCE: 41
ggaacgacgt cgttgggggg                   20

<210> SEQ ID NO 42
<211> LENGTH: 20
<212> TYPE: DNA
<213> ORGANISM: Artificial
<220> FEATURE:
<223> OTHER INFORMATION: Mod73. Contains palindrome sequence.

<400> SEQUENCE: 42 gggggggaacg acgtcgttgg                  20

<210> SEQ ID NO 43
<211> LENGTH: 21
<212> TYPE: DNA
<213> ORGANISM: Artificial
<220> FEATURE:
<223> OTHER INFORMATION: Contains palindrome sequence.

<400> SEQUENCE: 43
gggggggagc cgatcggctg g                 21

<210> SEQ ID NO 44
<211> LENGTH: 21
<212> TYPE: DNA
<213> ORGANISM: Artificial
<220> FEATURE:
<223> OTHER INFORMATION: Contains palindrome sequence.

<400> SEQUENCE: 44
gggggggagc cgatcggcag g                 21

```
<210> SEQ ID NO 45
<211> LENGTH: 21
<212> TYPE: DNA
<213> ORGANISM: Artificial
<220> FEATURE:
<223> OTHER INFORMATION: Contains palindrome sequence.

<400> SEQUENCE: 45
gggggggtgc cgatcggctg g                                              21

<210> SEQ ID NO 46
<211> LENGTH: 21
<212> TYPE: DNA
<213> ORGANISM: Artificial
<220> FEATURE:
<223> OTHER INFORMATION: Contains palindrome sequence.

<400> SEQUENCE: 46
gggggggagc cgatcggccg g                                              21

<210> SEQ ID NO 47
<211> LENGTH: 21
<212> TYPE: DNA
<213> ORGANISM: Artificial
<220> FEATURE:
<223> OTHER INFORMATION: Contains palindrome sequence.

<400> SEQUENCE: 47
gggggggcgc cgatcggccg g                                              21

<210> SEQ ID NO 48
<211> LENGTH: 21
<212> TYPE: DNA
<213> ORGANISM: Artificial
<220> FEATURE:
<223> OTHER INFORMATION: Mod84. Contains palindrome sequence.

<400> SEQUENCE: 48
gggggggtga cgatcgtcag g                                              21

<210> SEQ ID NO 49
<211> LENGTH: 21
<212> TYPE: DNA
<213> ORGANISM: Artificial
<220> FEATURE:
<223> OTHER INFORMATION: Contains palindrome sequence.

<400> SEQUENCE: 49
gggggggtga cgatcgtctg g                                              21

<210> SEQ ID NO 50
<211> LENGTH: 21
<212> TYPE: DNA
<213> ORGANISM: Artificial
<220> FEATURE:
<223> OTHER INFORMATION: Mod85. Contains palindrome sequence.

<400> SEQUENCE: 50
gggggggaga cgatcgtcag g                                              21

<210> SEQ ID NO 51
<211> LENGTH: 21
<212> TYPE: DNA
<213> ORGANISM: Artificial
<220> FEATURE:
<223> OTHER INFORMATION: Mod83. Contains palindrome sequence.
```

```
<400> SEQUENCE: 51
gggggggaga cgatcgtctg g                                              21

<210> SEQ ID NO 52
<211> LENGTH: 21
<212> TYPE: DNA
<213> ORGANISM: Artificial
<220> FEATURE:
<223> OTHER INFORMATION: Mod87. Contains palindrome sequence.

<400> SEQUENCE: 52 ggggggggcga cgatcgtcag g                                             21

<210> SEQ ID NO 53
<211> LENGTH: 21
<212> TYPE: DNA
<213> ORGANISM: Artificial
<220> FEATURE:
<223> OTHER INFORMATION: Contains palindrome sequence.

<400> SEQUENCE: 53
gggggggtga cgatcgttag g                                              21

<210> SEQ ID NO 54
<211> LENGTH: 21
<212> TYPE: DNA
<213> ORGANISM: Artificial
<220> FEATURE:
<223> OTHER INFORMATION: Contains palindrome sequence.

<400> SEQUENCE: 54
gggggggcga cgatcgtcgg g                                              21

<210> SEQ ID NO 55
<211> LENGTH: 20
<212> TYPE: DNA
<213> ORGANISM: Artificial
<220> FEATURE:
<223> OTHER INFORMATION: G1-GACGATCGTC-G9. Contains palindrome sequence.

<400> SEQUENCE: 55
ggacgatcgt cggggggggg                                                20

<210> SEQ ID NO 56
<211> LENGTH: 30
<212> TYPE: DNA
<213> ORGANISM: Artificial
<220> FEATURE:
<223> OTHER INFORMATION: G10. Contains palindrome sequence.

<400> SEQUENCE: 56
gggggggggg gacgatcgtc gggggggggg                                     30

<210> SEQ ID NO 57
<211> LENGTH: 19
<212> TYPE: DNA
<213> ORGANISM: Artificial
<220> FEATURE:
<223> OTHER INFORMATION: G3-6. Contains palindrome sequence.

<400> SEQUENCE: 57
ggggacgatc gtcggggggg                                                19

<210> SEQ ID NO 58
<211> LENGTH: 20
<212> TYPE: DNA
```

```
<213> ORGANISM: Artificial
<220> FEATURE:
<223> OTHER INFORMATION: 2332. Contains palindrome sequence.

<400> SEQUENCE: 58
ggggacgatc gtcggggggg                                                  20

<210> SEQ ID NO 59
<211> LENGTH: 6
<212> TYPE: DNA
<213> ORGANISM: Artificial
<220> FEATURE:
<223> OTHER INFORMATION: palindrome sequence

<400> SEQUENCE: 59 cgatcg                                                                  6

<210> SEQ ID NO 60
<211> LENGTH: 6
<212> TYPE: DNA
<213> ORGANISM: Artificial
<220> FEATURE:
<223> OTHER INFORMATION: palindrome sequence

<400> SEQUENCE: 60 atcgat                                                                  6

<210> SEQ ID NO 61
<211> LENGTH: 6
<212> TYPE: DNA
<213> ORGANISM: Artificial
<220> FEATURE:
<223> OTHER INFORMATION: palindrome sequence

<400> SEQUENCE: 61 gacgtc                                                                  6

<210> SEQ ID NO 62
<211> LENGTH: 8
<212> TYPE: DNA
<213> ORGANISM: Artificial
<220> FEATURE:
<223> OTHER INFORMATION: palindrome sequence

<400> SEQUENCE: 62 ccgatcgg                                                                8

<210> SEQ ID NO 63
<211> LENGTH: 8
<212> TYPE: DNA
<213> ORGANISM: Artificial
<220> FEATURE:
<223> OTHER INFORMATION: palindrome sequence

<400> SEQUENCE: 63 gcgatcgc                                                                8

<210> SEQ ID NO 64
<211> LENGTH: 8
<212> TYPE: DNA
<213> ORGANISM: Artificial
<220> FEATURE:
<223> OTHER INFORMATION: palindrome sequence

<400> SEQUENCE: 64 acgatcgt                                                                8
```

```
<210> SEQ ID NO 65
<211> LENGTH: 8
<212> TYPE: DNA
<213> ORGANISM: Artificial
<220> FEATURE:
<223> OTHER INFORMATION: palindrome sequence

<400> SEQUENCE: 65 catcgatg                                                                    8

<210> SEQ ID NO 66
<211> LENGTH: 8
<212> TYPE: DNA
<213> ORGANISM: Artificial
<220> FEATURE:
<223> OTHER INFORMATION: palindrome sequence

<400> SEQUENCE: 66 gatcgatc                                                                    8

<210> SEQ ID NO 67
<211> LENGTH: 8
<212> TYPE: DNA
<213> ORGANISM: Artificial
<220> FEATURE:
<223> OTHER INFORMATION: palindrome sequence

<400> SEQUENCE: 67 atcgcgat                                                                    8

<210> SEQ ID NO 68
<211> LENGTH: 8
<212> TYPE: DNA
<213> ORGANISM: Artificial
<220> FEATURE:
<223> OTHER INFORMATION: palindrome sequence

<400> SEQUENCE: 68 gaacgttc                                                                    8

<210> SEQ ID NO 69
<211> LENGTH: 8
<212> TYPE: DNA
<213> ORGANISM: Artificial
<220> FEATURE:
<223> OTHER INFORMATION: palindrome sequence

<400> SEQUENCE: 69 caacgttg                                                                    8

<210> SEQ ID NO 70
<211> LENGTH: 8
<212> TYPE: DNA
<213> ORGANISM: Artificial
<220> FEATURE:
<223> OTHER INFORMATION: palindrome sequence

<400> SEQUENCE: 70 agcgcgct                                                                    8

<210> SEQ ID NO 71
<211> LENGTH: 8
<212> TYPE: DNA
<213> ORGANISM: Artificial
<220> FEATURE:
<223> OTHER INFORMATION: palindrome sequence
```

```
<400> SEQUENCE: 71 acgtacgt                                                              8

<210> SEQ ID NO 72
<211> LENGTH: 8
<212> TYPE: DNA
<213> ORGANISM: Artificial
<220> FEATURE:
<223> OTHER INFORMATION: palindrome sequence

<400> SEQUENCE: 72 tagcgcta                                                              8

<210> SEQ ID NO 73
<211> LENGTH: 8
<212> TYPE: DNA
<213> ORGANISM: Artificial
<220> FEATURE:
<223> OTHER INFORMATION: palindrome sequence

<400> SEQUENCE: 73 acggccgt                                                              8

<210> SEQ ID NO 74
<211> LENGTH: 8
<212> TYPE: DNA
<213> ORGANISM: Artificial
<220> FEATURE:
<223> OTHER INFORMATION: palindrome sequence

<400> SEQUENCE: 74 cgacgtcg                                                              8

<210> SEQ ID NO 75
<211> LENGTH: 8
<212> TYPE: DNA
<213> ORGANISM: Artificial
<220> FEATURE:
<223> OTHER INFORMATION: palindrome sequence

<400> SEQUENCE: 75 cgtcgacg                                                              8

<210> SEQ ID NO 76
<211> LENGTH: 10
<212> TYPE: DNA
<213> ORGANISM: Artificial
<220> FEATURE:
<223> OTHER INFORMATION: palindrome sequence

<400> SEQUENCE: 76
gacgatcgtc                                                           10

<210> SEQ ID NO 77
<211> LENGTH: 10
<212> TYPE: DNA
<213> ORGANISM: Artificial
<220> FEATURE:
<223> OTHER INFORMATION: palindrome sequence

<400> SEQUENCE: 77
ggcgatcgcc                                                           10

<210> SEQ ID NO 78
<211> LENGTH: 10
<212> TYPE: DNA
```

```
<213> ORGANISM: Artificial
<220> FEATURE:
<223> OTHER INFORMATION: palindrome sequence

<400> SEQUENCE: 78
cgatcgatcg                                                             10

<210> SEQ ID NO 79
<211> LENGTH: 10
<212> TYPE: DNA
<213> ORGANISM: Artificial
<220> FEATURE:
<223> OTHER INFORMATION: palindrome sequence

<400> SEQUENCE: 79
gatcgcgatc                                                             10

<210> SEQ ID NO 80
<211> LENGTH: 10
<212> TYPE: DNA
<213> ORGANISM: Artificial
<220> FEATURE:
<223> OTHER INFORMATION: palindrome sequence

<400> SEQUENCE: 80
gcaacgttgc                                                             10

<210> SEQ ID NO 81
<211> LENGTH: 10
<212> TYPE: DNA
<213> ORGANISM: Artificial
<220> FEATURE:
<223> OTHER INFORMATION: palindrome sequence

<400> SEQUENCE: 81
gcatcgatgc                                                             10

<210> SEQ ID NO 82
<211> LENGTH: 10
<212> TYPE: DNA
<213> ORGANISM: Artificial
<220> FEATURE:
<223> OTHER INFORMATION: palindrome sequence

<400> SEQUENCE: 82
cagcgcgctg                                                             10

<210> SEQ ID NO 83
<211> LENGTH: 10
<212> TYPE: DNA
<213> ORGANISM: Artificial
<220> FEATURE:
<223> OTHER INFORMATION: palindrome sequence

<400> SEQUENCE: 83
gacgtacgtc                                                             10

<210> SEQ ID NO 84
<211> LENGTH: 10
<212> TYPE: DNA
<213> ORGANISM: Artificial
<220> FEATURE:
<223> OTHER INFORMATION: palindrome sequence

<400> SEQUENCE: 84
ctagcgctag                                                             10
```

```
<210> SEQ ID NO 85
<211> LENGTH: 10
<212> TYPE: DNA
<213> ORGANISM: Artificial
<220> FEATURE:
<223> OTHER INFORMATION: palindrome sequence

<400> SEQUENCE: 85
cccgatcggg                                                          10

<210> SEQ ID NO 86
<211> LENGTH: 10
<212> TYPE: DNA
<213> ORGANISM: Artificial
<220> FEATURE:
<223> OTHER INFORMATION: palindrome sequence

<400> SEQUENCE: 86
gacggccgtc                                                          10

<210> SEQ ID NO 87
<211> LENGTH: 10
<212> TYPE: DNA
<213> ORGANISM: Artificial
<220> FEATURE:
<223> OTHER INFORMATION: palindrome sequence

<400> SEQUENCE: 87
gccgatcggc                                                          10

<210> SEQ ID NO 88
<211> LENGTH: 10
<212> TYPE: DNA
<213> ORGANISM: Artificial
<220> FEATURE:
<223> OTHER INFORMATION: palindrome sequence

<400> SEQUENCE: 88
tccgatcgga                                                          10

<210> SEQ ID NO 89
<211> LENGTH: 10
<212> TYPE: DNA
<213> ORGANISM: Artificial
<220> FEATURE:
<223> OTHER INFORMATION: palindrome sequence

<400> SEQUENCE: 89
acgtcgacgt                                                          10

<210> SEQ ID NO 90
<211> LENGTH: 10
<212> TYPE: DNA
<213> ORGANISM: Artificial
<220> FEATURE:
<223> OTHER INFORMATION: palindrome sequence

<400> SEQUENCE: 90
acaacgttgt                                                          10

<210> SEQ ID NO 91
<211> LENGTH: 10
<212> TYPE: DNA
<213> ORGANISM: Artificial
<220> FEATURE:
<223> OTHER INFORMATION: palindrome sequence
```

```
<400> SEQUENCE: 91
acgacgtcgt                                                              10

<210> SEQ ID NO 92
<211> LENGTH: 6
<212> TYPE: DNA
<213> ORGANISM: Artificial
<220> FEATURE:
<223> OTHER INFORMATION: palindrome sequence

<400> SEQUENCE: 92 aacgtt                                                                  6

<210> SEQ ID NO 93
<211> LENGTH: 6
<212> TYPE: DNA
<213> ORGANISM: Artificial
<220> FEATURE:
<223> OTHER INFORMATION: palindrome sequence

<400> SEQUENCE: 93 agcgct                                                                  6

<210> SEQ ID NO 94
<211> LENGTH: 21
<212> TYPE: DNA
<213> ORGANISM: Artificial
<220> FEATURE:
<223> OTHER INFORMATION: Contains palindrome sequence.

<400> SEQUENCE: 94 ggggggggtga cgatcgtcgg g                                                21

<210> SEQ ID NO 95
<211> LENGTH: 20
<212> TYPE: DNA
<213> ORGANISM: Artificial
<220> FEATURE:
<223> OTHER INFORMATION: Mod93. Contains palindrome sequence.

<400> SEQUENCE: 95
ggggggggcg acgatcgtcg                                                   20

<210> SEQ ID NO 96
<211> LENGTH: 20
<212> TYPE: DNA
<213> ORGANISM: Artificial
<220> FEATURE:
<223> OTHER INFORMATION: Contains palindrome sequence.

<400> SEQUENCE: 96
ggggggggtg acgatcgtcg                                                   20

<210> SEQ ID NO 97
<211> LENGTH: 20
<212> TYPE: DNA
<213> ORGANISM: Artificial
<220> FEATURE:
<223> OTHER INFORMATION: Mod92. Contains palindrome sequence.

<400> SEQUENCE: 97 gggggggtgac gatcgtcggg                                                  20

<210> SEQ ID NO 98
<211> LENGTH: 20
<212> TYPE: DNA
```

<213> ORGANISM: Artificial
<220> FEATURE:
<223> OTHER INFORMATION: G7-GACGATCGTC-G3. Contains palindrome sequence.

<400> SEQUENCE: 98 gggggggggac gatcgtcggg                                              20

<210> SEQ ID NO 99
<211> LENGTH: 20
<212> TYPE: DNA
<213> ORGANISM: Artificial
<220> FEATURE:
<223> OTHER INFORMATION: Contains palindrome sequence.

<400> SEQUENCE: 99 ggggggggtcg acgtcgtggg                                              20

<210> SEQ ID NO 100
<211> LENGTH: 19
<212> TYPE: DNA
<213> ORGANISM: Artificial
<220> FEATURE:
<223> OTHER INFORMATION: Contains palindrome sequence.

<400> SEQUENCE: 100
gggggggtcg acgtcgtgg                                                19

<210> SEQ ID NO 101
<211> LENGTH: 19
<212> TYPE: DNA
<213> ORGANISM: Artificial
<220> FEATURE:
<223> OTHER INFORMATION: Contains palindrome sequence.

<400> SEQUENCE: 101
gggggggacg acgtcgtgg                                                19

<210> SEQ ID NO 102
<211> LENGTH: 19
<212> TYPE: DNA
<213> ORGANISM: Artificial
<220> FEATURE:
<223> OTHER INFORMATION: Contains palindrome sequence.

<400> SEQUENCE: 102
gggggggtcg acgtcgagg                                                19

<210> SEQ ID NO 103
<211> LENGTH: 19
<212> TYPE: DNA
<213> ORGANISM: Artificial
<220> FEATURE:
<223> OTHER INFORMATION: Contains palindrome sequence.

<400> SEQUENCE: 103
ggggggggac gacgtcgtg                                                19

<210> SEQ ID NO 104
<211> LENGTH: 19
<212> TYPE: DNA
<213> ORGANISM: Artificial
<220> FEATURE:
<223> OTHER INFORMATION: Contains palindrome sequence.

<400> SEQUENCE: 104 gggggggtc gacgtcgag                                                 19

```
<210> SEQ ID NO 105
<211> LENGTH: 20
<212> TYPE: DNA
<213> ORGANISM: Artificial
<220> FEATURE:
<223> OTHER INFORMATION: Contains palindrome sequence.

<400> SEQUENCE: 105
gggggggacg acgtcgtcgg                                              20

<210> SEQ ID NO 106
<211> LENGTH: 19
<212> TYPE: DNA
<213> ORGANISM: Artificial
<220> FEATURE:
<223> OTHER INFORMATION: Contains palindrome sequence.

<400> SEQUENCE: 106
ggggggggac gacgtcgtc                                               19

<210> SEQ ID NO 107
<211> LENGTH: 20
<212> TYPE: DNA
<213> ORGANISM: Artificial
<220> FEATURE:
<223> OTHER INFORMATION: Contains palindrome sequence.

<400> SEQUENCE: 107
gggggggtcg acgtcgaggg                                              20

<210> SEQ ID NO 108
<211> LENGTH: 20
<212> TYPE: DNA
<213> ORGANISM: Artificial
<220> FEATURE:
<223> OTHER INFORMATION: 1668. Contains palindrome sequence.

<400> SEQUENCE: 108
tccatgacgt tcctgatgct                                              20

<210> SEQ ID NO 109
<211> LENGTH: 12
<212> TYPE: DNA
<213> ORGANISM: Artificial Sequence
<220> FEATURE:
<223> OTHER INFORMATION: Palindrome sequence common to Mod29
      (SEQ ID NO:21) and Mod43 (SEQ ID NO:22)

<400> SEQUENCE: 109
tcccgatcgg ga                                                      12

<210> SEQ ID NO 110
<211> LENGTH: 12
<212> TYPE: DNA
<213> ORGANISM: Artificial Sequence
<220> FEATURE:
<223> OTHER INFORMATION: Palindrome sequence common to Mod37
      (SEQ ID NO:23) and Mod44 (SEQ ID NO:24)

<400> SEQUENCE: 110
ttccgatcgg aa                                                      12

<210> SEQ ID NO 111
<211> LENGTH: 12
<212> TYPE: DNA
<213> ORGANISM: Artificial Sequence
<220> FEATURE:
```

<223> OTHER INFORMATION: Palindrome sequence common to Mod38
      (SEQ ID NO:25) and Mod45 (SEQ ID NO:26)

<400> SEQUENCE: 111
tggcgatcgc ca                                                            12

<210> SEQ ID NO 112
<211> LENGTH: 12
<212> TYPE: DNA
<213> ORGANISM: Artificial Sequence
<220> FEATURE:
<223> OTHER INFORMATION: Palindrome sequence common to Mod39
      (SEQ ID NO:27) and Mod46 (SEQ ID NO:28)

<400> SEQUENCE: 112
tgacgatcgt ca                                                            12

<210> SEQ ID NO 113
<211> LENGTH: 12
<212> TYPE: DNA
<213> ORGANISM: Artificial Sequence
<220> FEATURE:
<223> OTHER INFORMATION: Palindrome sequence common to D19
      (SEQ ID NO:29) and Mod47 (SEQ ID NO:30)

<400> SEQUENCE: 113
tgcatcgatg ca                                                            12

<210> SEQ ID NO 114
<211> LENGTH: 12
<212> TYPE: DNA
<213> ORGANISM: Artificial Sequence
<220> FEATURE:
<223> OTHER INFORMATION: Palindrome sequence common to Mod70
      (SEQ ID NO:39) and Mod71 (SEQ ID NO:40)

<400> SEQUENCE: 114
gacgacgtcg tc                                                            12

<210> SEQ ID NO 115
<211> LENGTH: 12
<212> TYPE: DNA
<213> ORGANISM: Artificial Sequence
<220> FEATURE:
<223> OTHER INFORMATION: Palindrome sequence common to Mod72
      (SEQ ID NO:41) and Mod73 (SEQ ID NO:42)

<400> SEQUENCE: 115
aacgacgtcg tt                                                            12

<210> SEQ ID NO 116
<211> LENGTH: 12
<212> TYPE: DNA
<213> ORGANISM: Artificial Sequence
<220> FEATURE:
<223> OTHER INFORMATION: Palindrome sequence

<400> SEQUENCE: 116
tgccgatcgg ca                                                            12

<210> SEQ ID NO 117
<211> LENGTH: 37
<212> TYPE: DNA
<213> ORGANISM: Artificial Sequence
<220> FEATURE:
<223> OTHER INFORMATION: Palindrome Sequence
<220> FEATURE:
<221> NAME/KEY: misc_feature

```
<222> LOCATION: (1)..(10)
<223> OTHER INFORMATION: May be present or absent, and the minimum
      number of nucleotides represented by positions 1-10 is six and the
      maximum is ten.
<220> FEATURE:
<221> NAME/KEY: misc_feature
<222> LOCATION: (1)..(37)
<223> OTHER INFORMATION: The length of the oligonucleotide may be 16 to
      37 nucleotides.
<220> FEATURE:
<221> NAME/KEY: misc_feature
<222> LOCATION: (11)..(11)
<223> OTHER INFORMATION: Any single nucleotide other than guanine.
<220> FEATURE:
<221> NAME/KEY: misc_feature
<222> LOCATION: (12)..(21)
<223> OTHER INFORMATION: May be present or absent, and the minimum
      number of nucleotides represented by positions 12-21 is 0 and the
      maximum is ten. May be A, G, C, or T/U, or other. But does not
      contain four or more consecutive guanines.
<220> FEATURE:
<221> NAME/KEY: misc_feature
<222> LOCATION: (12)..(33)
<223> OTHER INFORMATION: Contains a palindrome sequence having a length
      of at least 8 nucleotides, and the minimum number of nucleotides
      respresented by positions 12-33 is eight and the maximum is 22.
<220> FEATURE:
<221> NAME/KEY: misc_feature
<222> LOCATION: (12)..(33)
<223> OTHER INFORMATION: Contains the sequence of CGATCG (SEQ ID NO:
      59), ATCGAT (SEQ ID NO: 60), or GACGTC (SEQ ID NO: 61).
<220> FEATURE:
<221> NAME/KEY: misc_feature
<222> LOCATION: (12)..(21)
<223> OTHER INFORMATION: The total number of nucleotides represented by
      positions 12 to 21 plus the nucleotides represented by positions
      24 to 33 is at least 6 nucleotides and at most 20 nucleotides.
<220> FEATURE:
<221> NAME/KEY: misc_feature
<222> LOCATION: (24)..(33)
<223> OTHER INFORMATION: May be present or absent, and the minimum
      number of nucleotides represented by positions 24-33 is 0 and the
      maximum is ten. May be A, G, C, or T/U, or other.  But does not
      contain four or more consecutive guanines.
<220> FEATURE:
<221> NAME/KEY: misc_feature
<222> LOCATION: (24)..(33)
<223> OTHER INFORMATION: The total number of nucleotides represented by
      positions 12 to 21 plus the nucleotides represented by positions
      24 to 33 is at least 6 nucleotides and at most 20 nucleotides.
<220> FEATURE:
<221> NAME/KEY: misc_feature
<222> LOCATION: (34)..(34)
<223> OTHER INFORMATION: Any single nucleotide other than guanine.
<220> FEATURE:
<221> NAME/KEY: misc_feature
<222> LOCATION: (35)..(37)
<223> OTHER INFORMATION: May be present or absent, and the minimum
      number of nucleotides represented by positions 35-37 is 0 and the
      maximum is three.

<400> SEQUENCE: 117
gggggggggg nnnnnnnnnn ncgnnnnnnn nnnnggg                              37

<210> SEQ ID NO 118
<211> LENGTH: 37
<212> TYPE: DNA
<213> ORGANISM: Artificial Sequence
<220> FEATURE:
<223> OTHER INFORMATION: Palindrome Sequence
<220> FEATURE:
<221> NAME/KEY: misc_feature
<222> LOCATION: (1)..(10)
<223> OTHER INFORMATION: May be present or absent, and the minimum
      number of nucleotides represented by positions 1-10 is six and
      the maximum is 10.
<220> FEATURE:
<221> NAME/KEY: misc_feature
```

```
<222> LOCATION: (1)..(37)
<223> OTHER INFORMATION: The length of the oligonucleotide may be 16 to
      37 nucleotides.
<220> FEATURE:
<221> NAME/KEY: misc_feature
<222> LOCATION: (11)..(11)
<223> OTHER INFORMATION: Any single nucleotide other than guanine.
<220> FEATURE:
<221> NAME/KEY: misc_feature
<222> LOCATION: (12)..(21)
<223> OTHER INFORMATION: May be present or absent, and the minimum
      number of nucleotides represented by positions 12-21 is 0 and the
      maximum is ten. May be A, G, C, or T/U, or other. But does not
      contain four or more consecutive guanines.
<220> FEATURE:
<221> NAME/KEY: misc_feature
<222> LOCATION: (12)..(21)
<223> OTHER INFORMATION: The total number of nucleotides represented by
      positions 12 to 21 plus the nucleotides represented by positions
      24 to 33 is at least 6 nucleotides and at most 20 nucleotides.
<220> FEATURE:
<221> NAME/KEY: misc_feature
<222> LOCATION: (12)..(33)
<223> OTHER INFORMATION: Contains a palindrome sequence having a length
      of at least 8 nucleotides, and the minimum number of nucleotides
      represented by positions 12-33 is eight and the maximum is 22.
<220> FEATURE:
<221> NAME/KEY: misc_feature
<222> LOCATION: (24)..(33)
<223> OTHER INFORMATION: The total number of nucleotides represented by
      positions 12 to 21 plus the nucleotides represented by positions
      24 to 33 is at least 6 nucleotides and at most 20 nucleotides.
<220> FEATURE:
<221> NAME/KEY: misc_feature
<222> LOCATION: (24)..(33)
<223> OTHER INFORMATION: May be present or absent, and the minimum
      number of nucleotides represented by positions 24-33 is 0 and the
      maximum is ten. May be A, G, C, or T/U, or other. But does not
      contain four or more consecutive guanines.
<220> FEATURE:
<221> NAME/KEY: misc_feature
<222> LOCATION: (34)..(34)
<223> OTHER INFORMATION: Any single nucleotide other than guanine.
<220> FEATURE:
<221> NAME/KEY: misc_feature
<222> LOCATION: (35)..(37)
<223> OTHER INFORMATION: May be present or absent, and the minimum
      number of nucleotides represented by positions 35-37 is 0 and the
      maximum is three.

<400> SEQUENCE: 118
gggggggggg hnnnnnnnnn ncgnnnnnnn nnnhggg                            37
```

IMMUNOSTIMULATORY OLIGONUCLEOTIDES AND USE THEREOF IN PHARMACEUTICALS

TECHNICAL FIELD

The present invention relates to immunostimulatory oligonucleotides and use thereof in pharmaceuticals, and particularly relates to novel oligonucleotides by which an interferon (IFN)-inducing activity is augmented and an inflammatory cytokine-inducing activity is reduced, and pharmaceuticals containing the oligonucleotides and the use thereof.

BACKGROUND ART

Tokunaga et al. have reported that a particular type of bacterial DNA stimulates an immune response (Yamamoto et al., Jpn. J. Cancer Res. 79:866-873, 1988). A major component of the bacterial DNA essential for an immunostimulatory activity is a characteristic short sequence structure containing a CpG dinucleotide motif (hereinafter abbreviated as CpG) which is not methylated. It has been also reported that a synthesized CpG-containing oligonucleotide induces the production of type I IFN (IFN-α and IFN-β) and IFN-γ in macrophages and natural killer (NK) cells and has a cytotoxic activity of the NK cells (JP Hei-4-352724-A). It has been also reported that the CpG-containing oligonucleotide acts upon not only the macrophages but also dendritic cells and B cells and induces a cell proliferative activity and the production of inflammatory cytokines of interleukin-12 (IL-12), tumor necrosis factor (TNF-α) and interleukin-6 (IL-6) (Klinman et al., Proc. Natl. Acad. Sci., 93:2879-2883, 1996). Thus, the CpG-containing oligonucleotide is useful as an adjuvant of a vaccine and for the treatment of allergic diseases because it induces cellular immunity and Th1 responses. On the other hand, it can not be denied that the CpG-containing oligonucleotide might trigger side effects such as sepsis, fever, joint pain, muscular pain and flare because of inducing the production of TNF-α and IL-6.

Tokunaga et al., have found that the oligonucleotide containing the CpG motif and composed of a 6 bases-palindrome motif has strong activity in the cytotoxic activity in the murine NK cells, and have reported that the sequences of 5'-AACGTT-3' (SEQ ID NO:92), 5'-AGCGCT-3' (SEQ ID NO:93) and 5'-GACGTC-3' (SEQ ID NO:61) have the strongest activity (Yamamoto at el., J. Immunol., 148:4072-4076, 1992). Other types of immunostimulatory oligonucleotide sequences have been reported (International Publication No. 1998/018810 Pamphlet, International Publication No. 2003/015711 Pamphlet, International Publication No. 2004/058179 Pamphlet).

Studies for the purpose of augmenting activity of oligonucleotides have been also conducted. Tokunaga et al., have found that NK cell activities and IFN-inducing activities are augmented when a repeating structure of deoxyguanylic acid (poly-G sequence) is inserted outside the 6 bases-palindrome motif containing CpG (JP Hei-4-352724-A). It has been also demonstrated that the sequence outside the 6 bases-sequence containing the CpG motif has no small effect on the activity.

The other CpG-containing sequences known publicly include D-type (or A-type) and K-type (or B-type) of immunostimulatory oligonucleotides (International Publication No. 2000/61151 Pamphlet). The K-type is known to activate the B cells. The D-type, where a poly-G sequence is added outside the CpG-containing palindrome sequence, induces a production of type I IFN in the dendritic cells and activates human NK cells. It has been described that, for the IFN-inducing activity of the D-type, the 3' terminal side is important, and 4 or more bases are required for a length of the poly-G sequence at the 3' terminal (International Publication No. 2000/61151 Pamphlet). Meanwhile, it has been also described that the poly-G sequence at the 3' terminal side is important for activities of inducing the production of inflammatory cytokines of IL-12 and TNF-α, and a poly-G sequence of at least 4 or more bases is required for eliciting these effects (Korea KR 2001-063153). Therefore, the sequences of the publicly known oligonucleotides which enhance immunostimulatory activities, or the structure of a poly-G sequence does not reveal an independency of the induction of IFN and the induction of inflammatory cytokines.

It has been found that the immunostimulatory nucleotide having the palindrome motif of 5'-GACGATCGTC-3' (SEQ ID NO:76) has stronger activity of inducing IFN-α than the conventional unmodified CpG-containing immunostimulatory nucleotides (the effect of modified ones will be described later), by inserting a poly-G sequence having an appropriate length up to 10 at the 3' terminus and the 5' terminus (JP 2005-237328-A). It has been disclosed that to confer a higher activity of inducing IFN-α to the immunostimulatory nucleotides having 5'-GACGATCGTC-3' (SEQ ID NO:76), it is better to put 8 to 10 G bases at the 3' terminus or the 5' terminus, but to inhibit a production of interleukin-10 (IL-10) which is an immunosuppressive cytokine, it is better to put unevenly the base(s) at the 5' terminus only (JP 2005-237328-A). It has been also reported that the activity of inducing the inflammatory cytokines of TNF-α and IL-12 is moderately correlated to the activity of inducing INF-α. These do not reveal an effect by insertion of the poly-G sequence at the 5' terminus in a palindrome sequence other than 5'-GACGATCGTC-3' (SEQ ID NO:76). An optimal base number of the poly-G sequence of the CpG-containing oligonucleotide, by which the activity to induce an inflammatory cytokine is attenuated and the IFN-inducing activity for both IFN-γ and IFN-α is augmented, is not disclosed.

5'-GGTGCCGATCGGCAGGGGG-3' (SEQ ID NO:1) has been found as an oligonucleotide having higher immunostimulatory activity than the conventional D-type of CpC-oligonucleotide (JP 2004-287102-A). Derivatives obtained by substituting one to several bases in this base sequence have been also disclosed. Although no specific sequence obtained by substituting 3 or more bases has been disclosed, only one sequence, 5'-GGGGGGTGCCGATCGGCAGGG-3' (SEQ ID NO:5) obtained by substituting 7 bases has been found to have IFN-inducing activity even when the poly-G sequence at the 3' terminus is composed of three bases (International Publication No. 2006/035939 Pamphlet).

Concerning the other study for the purpose of augmenting the activity, stabilization of the oligonucleotide by chemical modification has been known. Naturally occurring phosphodiester nucleotides are degraded easily by various nucleic acid degradation activities in cells and in cell cultures. Therefore, it has been studied that, the phosphodiester nucleotides are stabilized by substituting an internucleotide phosphodiester bond which is an attack target of the nucleic acids degradation activity, and the resulting activity is augmented. A substitution frequently used is the substitution to phosphorothioate. The study by Klinman et al has shown that the induction of immune response is augmented by modifying a poly-G sequence outside the palindrome motif with phosphorothioate (International Publication No. 2000/61151 Pamphlet).

It has been found in the study using TLR9 knockout mice that a receptor for the bacterial DNA containing non-methylated CpG is TLR9, which is one member in Toll-like receptor (TLR) family (Hemmi, et al., Nature, 408:740-745, 2000). It has been also shown that the optimal CpG sequences to activate human TLR9 and murine TLR9 are different, indicating the presence of species specificity (Bauer, et al., PNAS, 98(16):9237-9242, 2001). In the development for the purpose of a therapy in human, it is essential that the CpG-oligonucleotide has high affinity to human TLR9. Also, it is important that the CpG-oligonucleotide acts upon animals such as mice in preclinical studies using the animals which are in developmental stage.

For the treatment of allergic diseases, not a symptomatic treatment currently used frequently but an immunoregulatory type and an effective radical treatment have been desired. In the patients with allergy, the immune response to an allergen is leans to Th2 and the Th1 immune response is suppressed. Therefore, a therapeutic agent that induces the Th1 immune response and suppresses the Th2 immune response is useful for improving an allergic predisposition. It has been disclosed that the CpG oligonucleotide composed of a certain non-palindrome sequence (JP 2003-286174-A) and the CpG-oligonucleotide containing the 6 base-palindrome 5'-AACGTT-3' (SEQ ID NO:92) (JP 2002-500159—, Tighe, et al., J. Allergy Clin. Immunol., 106:124-134, 2000) have therapeutic effects in a murine asthma model. However, the aforementioned immunostimulatory oligonucleotides are concerned to incur unfavorable side effects when administered at a pharmacologically effective amount because these not only induce the Th1 response but also elicit the inflammatory cytokines.

An allergic symptom is caused by extracellularly releasing granules (degranulation) containing histamine from mast cells, and this degranulation is caused by binding the allergen to IgE on the mast cell. In recent years, an antigen-specific regulatory T cell ($T_{reg}$) has been noted in its function to keep the immune balance. For example, the inhibition of the degranulation by $T_{reg}$ via IgE receptor FcεRI may be included (Till, et al., J. Allergy Clin. Immunol., 113:1025-1034). IFN-α and IFN-β are shown to facilitate the induction of the production of IL-10 (Aman, et al., Blood, 87:4731-4736, 1996). Furthermore, IL-10 promotes the induction of the differentiation of IgG4- and IgA-producing cells. Thus, it is conceivable that the induction of IL-10 is also one of mechanisms in allergy therapeutic effects by the immunostimulatory nucleotide. Therefore, it is desirable that the immunostimulatory nucleotide suitable for the allergy treatment augments the IFN-α-inducing activity and keeps the IL-10-inducing activity.

Hepatitis indicates the disease including hepatic inflammation induced by virus, alcohol, drug, toxin and autoimmunity.

Among them, a majority is the hepatitis caused by hepatitis virus, in particular, A, B and C types are frequent, and additionally the presence of D, E, F, G and idiopathic hepatitis virus has been known. The above viruses distribute in many different viral families of RNA types and DNA types.

Hepatitis B virus and hepatitis C virus cause acute and chronic infection. In acute hepatitis, the symptom appears in an early infection or in recurrence in chronic infected patients. Meanwhile, in chronic hepatitis C, the hepatic inflammation continues for 6 months or longer, and the cells are destroyed, and then hepatic functions are reduced. In the infection with HCV, it is also problematic that a risk to progress from the acute hepatitis to the chronic hepatitis is high. From such a circumstance, early interference by the treatment and a highly effective therapeutic method for hepatitis virus infection disease are desired.

In hepatitis type C, the treatment with various interferon (IFN) formulations alone or the combination treatment using the IFN-α formulation and ribavirin is the first choice of therapeutic means. In the combination treatment, the sustained effect can be expected compared with the treatment with a single medicament, but then, is more expensive and is accompanied with more side effects. However, even when these treatments are given, the therapeutic effect is observed in only about 60% of the total treated patients, and when the treatment is discontinued after the effect was observed, a half or more patients suffer a recurrence. From these circumstances, further developments of therapeutic drugs have been desired.

The therapeutic effects of the CpG oligonucleotide on the hepatitis may include augmentation of anti-viral effect by induction of interferon, the induction of cellular immunity against the cells infected with the virus and resistance to appearance of resistant strains. Concerning the use of the CpG-oligonucleotide for treating the hepatitis due to the infection with HBV or HCV, technical information is available in JP 2003-526662 and JP 2006-515277. The former has disclosed a method of treating without administering the CpG oligonucleotide (immune activation sequence: ISS) together with a hepatitis viral antigen. The latter has disclosed a method of treating individuals with chronic hepatitis type C where an antiviral agent such as interferon was ineffective, and the clinical study result of a developmental number CpG10101 for usefulness in the patients was disclosed in European Association for the Study of Liver Diseases in 2006. However, from this clinical study result, the therapeutic effect of CpG10101 alone is extremely insufficient compared with the conventional therapies. The combination therapy using three agents, pegylated IFN-α, ribavirin and the CpG-oligonucleotide is expected to have a slightly higher effectiveness compared with the result of the standard therapy such as pegylated IFN-α with ribavirin, but has been already demonstrated not to give a sufficient therapeutic effect compared with the combination with the other antiviral agents (e.g., a combination therapy with the inhibitor of a viral enzyme such as polymerase and protease).

It can not be denied that the existing CpC-oligonucleotide might elicit sepsis, fever, joint pain, muscular pain and reddening and unexpected side effects due to inducing the production of TNF-α, IL-12 and IL-6 which are the inflammatory cytokines. In fact, it has been shown that the existing CpG-oligonucleotide deteriorates a symptom of hepatitis in the study example using a murine hepatitis model (Abe, et al., Fukushima J. Med. Sci., 51:41-49, 2005). Therefore, it has been desired to develop CpG-oligonucleotides having the improved immunostimulatory activity suitable for the treatment of hepatitis and whose side effect is reduced.

Depending on an activity of the immunostimulatory oligonucleotides, it becomes possible to reduce a dosage and an administration frequency. As a result, it is highly likely that occurrence of a toxic action is reduced and QOL is improved.

In light of the foregoing, it is very useful and extremely highly beneficial in industrial application to find a sequence by which the IFN-inducing activity is enhanced and the inflammatory cytokine-inducing activity is reduced in human compared with the aforementioned existing immunostimulatory sequence.

DISCLOSURE OF INVENTION

Problem to be Solved by the Invention

It is an object of the present invention to provide a novel immunostimulatory oligonucleotide by which an interferon (IFN)-inducing activity is augmented and an inflammatory cytokine-inducing activity is reduced, and pharmaceuticals containing this immunostimulatory oligonucleotide and use thereof.

Means for Solving Problem

As a result of an extensive study for solving the problem, the present inventors have found that the 5' terminal side outside a sequence containing a CpG motif is important for an IFN-inducing activity. That is, the present inventors have demonstrated that an oligonucleotide having the interferon-inducing activity which is more excellent than in other oligonucleotides is obtained by inserting 6 or more bases of consecutive guanine sequence to the 5' terminal side. As a result of the further study, the present inventors have found that a CpG oligonucleotide having a poly-G sequence of 6 to 10 bases inserted in the terminal side, a poly-G sequence of 0 to 3 bases inserted in the 3' terminal side and a predetermined structural characteristic has a more strongly augmented activity of inducing type I IFN, i.e., IFN-α and IFN-β, and IFN-γ, and exhibits a reduced activity of inducing inflammatory cytokines, and has a higher activity of suppressing IgE production, a higher activity of suppressing Th2 and a higher activity of inducing Th1 than conventionally known oligonucleotides composed of a D-type CpG sequence. In addition to them, as a result of a study in a hepatitis murine model, the present inventors also have found that the oligonucleotide of the present invention also has a therapeutic effect for hepatitis in vivo, and have completed the present invention.

[1] An immunostimulatory oligonucleotide comprising: the base sequence thereof consisting of the sequence represented by the formula: 5'-$(G)_M$PXCGYQ$(G)_N$-3' (C is cytosine, G is guanine; X and Y are mutually independent and represent each an arbitrary sequence which has a length of 0 to 10 nucleotides and does not contain 4 or more consecutive guanine residues, and a length of X+Y is 6 to 20 nucleotides; XCGY contains a palindrome sequence having a length of at least 8 nucleotides and has a length of 8 to 22 nucleotides; P and Q are mutually independent and represent one nucleotide other than guanine, and M represents an integer of 6 to 10 and N represents an integer of 0 to 3; and each nucleotide length of X and Y needs not be necessarily the same length), and has a length of 16 to 37 nucleotides in total, except an oligonucleotide of which the base sequence is represented as SEQ ID NO:5 [GGGGGGTGCCGATCGGCAGGG]).

[2] The immunostimulatory oligonucleotide according to [1], wherein the M represents the integer of 6 to 8 and the total length is 16 to 35 nucleotides.

[3] The immunostimulatory oligonucleotide according to [1] or [2], wherein the XCGY has a length of 9 or 10 nucleotides and the total length is 17 to 23 nucleotides.

[4] The immunostimulatory oligonucleotide according to any one of [1] to [3], wherein the XCGY contains any one base sequence selected from CGATCG (SEQ ID NO:59), ATCCAT (SEQ ID NO:60) and GACGTC (SEQ ID NO:61).

[5] The immunostimulatory oligonucleotide according to any one of [1] to [3], wherein the XCGY contains CGATCG (SEQ ID NO:59).

[6] The immunostimulatory oligonucleotide according to [4] or [5], wherein the immunostimulatory oligonucleotide containing CGATCG (SEQ ID NO:59) is composed of SEQ ID NOS:6, 7, 9 to 11 and 15 to 18, 22, 24, 26, 28, 48, 50 to 52, 54, 95 and 97.

[7] The immunostimulatory oligonucleotide according to [4], wherein the immunostimulatory oligonucleotide containing CGATCG (SEQ ID NO:60) is composed of the base sequence of SEQ ID NO:30.

[8] The immunostimulatory oligonucleotide according to [4], wherein the immunostimulatory oligonucleotide containing CGATCG (SEQ ID NO:61) is composed of SEQ ID NO:40 and 42.

[9] The immunostimulatory oligonucleotide according to [4] or [5], wherein the immunostimulatory oligonucleotide is composed of base sequences SEQ ID NOS: 6, 7, 10 and 15 to 17, 24, 26, 28, 48, 50 to 52, 95 and 97.

[10] The immunostimulatory oligonucleotide according to any one of [1] to [9], wherein a phosphodiester linkage at all or a part of internucleotides is modified with phosphorothioate.

[11] The immunostimulatory oligonucleotide according to [10], wherein the phosphodiester linkage of at least a part of internucleotides, in a consecutive G sequence at the 5' terminus is modified with phosphorothioate.

[12] The immunostimulatory oligonucleotide according to [10] or [11], wherein the phosphodiester linkage of at least a part of internucleotides, at the 3' terminus is modified with phosphorothioate.

[13] A pharmaceutical containing the immunostimulatory oligonucleotide according to any one of [1] to [12] as an active ingredient.

[14] A therapeutic or preventive agent for an allergic disease containing the immunostimulatory oligonucleotide according to any one of [1] to [12] as an active ingredient.

[15] The therapeutic or preventive agent for the allergic disease according to [14], wherein said allergic disease is a pollen allergic disease.

[16] A vaccine containing the immunostimulatory oligonucleotide according to any one of [1] to [12] as an adjuvant.

[17] A therapeutic or preventive agent for hepatitis containing the immunostimulatory oligonucleotide according to any one of [1] to [12] as an active ingredient.

[18] The therapeutic or preventive agent for hepatitis according to [17], wherein the hepatitis is viral hepatitis.

[19] The therapeutic or preventive agent for hepatitis according to [18], wherein the viral hepatitis is hepatitis B or hepatitis C.

[20] Use of the immunostimulatory oligonucleotide according to any one of [1] to [12] as a therapeutic or preventive agent for an allergic disease.

[21] Use of the immunostimulatory oligonucleotide according to any one of [1] to [12] as an adjuvant for a vaccine.

[22] Use of the immunostimulatory oligonucleotide according to any one of [1] to [12] as a therapeutic or preventive agent for hepatitis.

[23] A method for treating or preventing an allergic disease by the immunostimulatory oligonucleotide according to any one of [1] to [12].

[24] A method of using the immunostimulatory oligonucleotide according to any one of [1] to [12] as an adjuvant for a vaccine.

[25] A method of treating or preventing hepatitis by the immunostimulatory oligonucleotide according to any one of [1] to [12].

Effect of the Invention

The novel immunostimulatory oligonucleotide provided by the present invention has high therapeutic effect because of excellent immunostimulatory activities, such as the augmented IFN-inducing activity, the reduced inflammatory cytokine-inducing activity, and high activities of suppressing the IgE production, suppressing Th2 and inducing Th1. In addition, as a result of the study with the murine hepatitis model, it has also been proved to have a therapeutic effect for hepatitis in vivo, too. Furthermore, it is possible to use at high doses because the risks of side effects are reduced. Therefore, the immunostimulatory oligonucleotide of the present invention makes the treatment and prevention of allergic diseases and/or hepatitis possible and allows use as a more efficient and safe vaccine adjuvant for a shorter period, compared with the conventional immunostimulatory oligonucleotides.

BRIEF DESCRIPTION OF DRAWINGS

FIG. 1-2 shows results of stimulating human PBMC with the immunostimulatory oligonucleotides of the present invention and measuring amounts of produced IFN-γ in culture supernatants in Example 1;

FIG. 1-3 shows results of stimulating human PBMC with the immunostimulatory oligonucleotides of the present invention and measuring amounts of produced IFN-α in culture supernatants in Example 1;

FIG. 1-4 shows results of stimulating human PBMC with the immunostimulatory oligonucleotides of the present invention and measuring amounts of produced IFN-γ in culture supernatants in Example 1;

FIG. 1-5 shows results of stimulating human PBMC with the immunostimulatory oligonucleotides of the present invention and measuring amounts of produced IFN-α in culture supernatants in Example 1;

FIG. 1-6 shows results of stimulating human PBMC with the immunostimulatory oligonucleotides of the present invention and measuring amounts of produced IFN-γ in culture supernatants in Example 1;

FIG. 2 shows results of stimulating murine J774 cells with the immunostimulatory oligonucleotides of the present invention and measuring amounts of produced Il-12 p40 in culture supernatants in Example 2;

FIG. 3-1 shows results of stimulating human PBMC with the immunostimulatory oligonucleotides (G6-PXCGYQ-G3) of the present invention or D-type CpG (G2-PXCGYQ-G6) having the same palindrome motif and measuring amounts of produced IFN-α in culture supernatants in Example 3;

FIG. 3-2 shows results of stimulating human PBMC with the immunostimulatory oligonucleotides (G6-PXCGYQ-G3) of the present invention or D-type CpG (G2-PXCGYQ-G6) having the same palindrome motif and measuring amounts of produced IFN-γ in culture supernatants in Example 3;

FIG. 3-3 shows results of stimulating human PBMC with the immunostimulatory oligonucleotides (G6/7-PXCGYQ-G2) of the present invention or D-type CpG (G2/3-PXCGYQ-G6) having the same palindrome motif and measuring amounts of produced IFN-α in culture supernatants in Example 3;

FIG. 4 shows results of stimulating human PBMC with the immunostimulatory oligonucleotides of the present invention and measuring amounts of produced IFN-α in culture supernatants in Example 4;

FIG. 5-1 shows results of stimulating human PBMC with the immunostimulatory oligonucleotides of the present invention or the publicly known oligonucleotides and measuring amounts of produced IFN-α in culture supernatants in Example 7;

FIG. 5-2 shows results of stimulating human PBMC with the immunostimulatory oligonucleotides of the present invention or the publicly known oligonucleotides and measuring amounts of produced IFN-α in culture supernatants in Example 7;

FIG. 5-3 shows results of stimulating human PBMC with the immunostimulatory oligonucleotides of the present invention or the publicly known oligonucleotides and measuring amounts of produced IFN-α in culture supernatants in Example 7;

FIG. 5-4 shows results of stimulating human PBMC with the immunostimulatory oligonucleotides of the present invention or the publicly known oligonucleotides and measuring amounts of produced IFN-α in culture supernatants in Example 7;

FIG. 6 shows results of stimulating human PBMC with the immunostimulatory oligonucleotides of the present invention or the publicly known oligonucleotides and measuring amounts of produced IFN-α in a culture supernatant in Example 8;

FIG. 7-1 shows results of stimulating murine splenic cells with the immunostimulatory oligonucleotides of the present invention or D-type CpG having the same palindrome motif and measuring amounts of produced IFN-γ in culture supernatants in Example 9;

FIG. 7-2 shows results of stimulating murine splenic cells with the immunostimulatory oligonucleotides of the present invention or D-type CpG having the same palindrome motif and measuring amounts of produced IL-10 in culture supernatants in Example 9;

FIG. 8-1 shows results of stimulating murine J774 cells with the immunostimulatory oligonucleotides (G6-PXCGYQ-G3) of the present invention or D-type CpG (G2-PXCGYQ-G6) having the same palindrome motif and measuring amounts of produced IL-12 in culture supernatants in Example 10;

FIG. 8-2 shows results of stimulating murine J774 cells with the immunostimulatory oligonucleotides (G6-PXCGYQ-G3) of the present invention or D-type CpG (G2-PXCGYQ-G6) having the same palindrome motif and measuring amounts of produced TNF-α in culture supernatants in Example 10;

FIG. 12-1 shows results of measuring the amounts of produced IFN-γ in culture supernatants obtained from Cry j1-stimulated splenic cells after eliciting the allergy by treating the mice with the immunostimulatory oligonucleotide of the present invention and the publicly known immunostimulatory oligonucleotide together with the cedar pollen antigen Cry j1 in Example 13;

FIG. 12-2 shows results of measuring the amounts of produced IL-5 in culture supernatants obtained from Cry j1-stimulated splenic cells after eliciting the allergy by treating the mice with the immunostimulatory oligonucleotide of the present invention or the publicly known immunostimulatory oligonucleotide together with the cedar pollen antigen Cry j1 in Example 13;

FIG. 14-1 shows results of comparing and evaluating the effects of the immunostimulatory oligonucleotide of the present invention and the publicly known immunostimulatory oligonucleotide on the elevation of ALT levels in serum in the Con-A induced murine hepatitis model in Example 15; and FIG. 14-2 shows results of comparing and evaluating the effects of the immunostimulatory oligonucleotide of the present invention and the publicly known immunostimulatory oligonucleotide on the elevation of ALT levels in serum in the Con-A induced murine hepatitis model in Example 15.

BEST MODES FOR CARRYING OUT THE INVENTION

Figure 1:
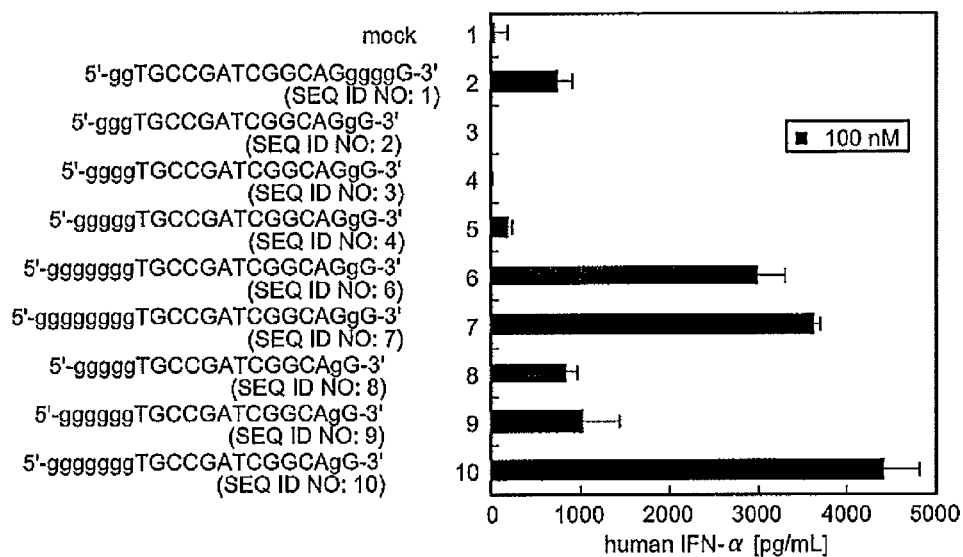
FIG. 1-1 shows results of stimulating human PBMC with the immunostimulatory oligonucleotides of the present invention and measuring amounts of produced IFN-α in culture supernatants in Example 1.

The immunostimulatory oligonucleotide of the present invention is comprising:

the base sequence thereof consisting of the sequence represented by the formula: 5'-$(G)_M$PXCGYQ$(G)_N$-3' (SEQ ID NO: 118)(C is cytosine, G is guanine; X and Y are mutually independent and represent each an arbitrary sequence which has a length of 0 to 10 nucleotides and does not contain 4 or more consecutive guanine residues, and a length of X+Y is 6 to 20 nucleotides; XCGY contains a palindrome sequence having a length of at least 8 nucleotides and has a length of 8 to 22 nucleotides; P and Q are mutually independent and represent one nucleotide other than guanine, and M represents an integer of 6 to 10 and N represents an integer of 0 to 3; and each nucleotide length of X and Y needs not be necessarily the same length), and 16 to 37 nucleotides in total, except an oligonucleotide of which the base sequence is represented as SEQ ID NO:5 [GGGGGGTGCCGATCGGCAGGG]).

The base sequence which constitutes the immunostimulatory oligonucleotide of the present invention is represented by the formula: 5'-$(G)_M$PXCGYQ$(G)_N$-3'. In the formula, "5'-" and "3'-" represent the 5' terminus and the 3' terminus, respectively. C is cytosine, G is guanine, X and Y are mutually independent and represent each an arbitrary sequence. P and Q are mutually independent and represent mutually one nucleotide. $(G)_M$ and $(G)_N$ respectively represent each the consecutive sequence composed of guanine (G) alone, and M and N represent a number of guanine. That is, the aforementioned formula is represented by generalizing the base sequence from the 5' terminus to the 3' terminus of the immunostimulatory oligonucleotide of the present invention. In the present invention, "XCGY" means an entire sequence composed of X, C, G and Y in the aforementioned formula, and "PXCGYQ" means an entire sequence composed of P, X, C, G, Y and Q in the aforementioned formula. For the aforementioned formula, the "length" means a number of the nucleotides (nucleotide length) which constitutes each sequence. Furthermore, "a length of X+Y" means a sum of the length of X and the length of Y.

In the aforementioned formula, each of X and Y has a length in the range of 0 to 10 nucleotides. In particular, it is preferable to be 2 to 6 nucleotides. The sequences of X and Y may be each independently composed of any nucleotides, but it is necessary not to contain 4 or more consecutive guanine bases. Furthermore, it is necessary that a length of X+Y is 6 to 20 nucleotides. The nucleotide length is preferably 6 to 12, more preferably 7 or 8, and most preferably 8. The nucleotide lengths of X and Y may be not always the same.

In the aforementioned formula, it is necessary that a palindrome sequence is contained in XCGY. The palindrome sequence means a base sequence composed of the bases bilaterally symmetric in a complementary style to an axis between arbitrary two bases, and is also referred to as a palindromic sequence. In the present invention, it is necessary that a length of the palindrome sequence contained in XCGY is 8 or more nucleotides. XCGY may be composed only of the palindrome sequence of 8 bases or more, and as long as the palindrome sequence of 8 bases or more is contained, the sequence need not be always fully complementary.

It is preferable that XCGY contains any one base sequence selected from CGATCG (SEQ ID NO:59), ATCGAT (SEQ ID NO:60) and GACGTC (SEQ ID NO:61). In particular, it is the most preferable to contain CGATCG (SEQ ID NO:59). These sequences per se are the palindrome sequences, and it is preferable that the palindrome sequence contained in XCGY contains these sequences as a part thereof.

Examples of the palindrome sequence in the present invention are shown below. In XCGY, the palindrome sequences of 8 bases-sequence may include CCGATCGG (SEQ ID NO:62), GCGATCGC (SEQ ID NO:63), ACGATCGT (SEQ ID NO:64), CATCGATG (SEQ ID NO:65), GATCGATC (SEQ ID NO:66), ATCGCGAT (SEQ ID NO:67), GAACGTTC (SEQ ID NO:68), CAACGTTG (SEQ ID NO:69), AGCGCGCT (SEQ ID NO:70), ACGTACGT (SEQ ID NO:71), TAGCGCTA (SEQ ID NO:72), ACGGCCGT (SEQ ID NO:73), CGACGTCG (SEQ ID NO:74) and CGTCGACG (SEQ ID NO:75). Among them, CCGATCGG (SEQ ID NO:62), GCGATCGC (SEQ ID NO:63), ACGATCGT (SEQ ID NO:64), CATCGATG (SEQ ID NO:65) and CGACGTCG (SEQ ID NO:74) are preferable. In XCGY, the palindrome sequences of 10 bases-sequence may include GACGATCGTC (SEQ ID NO:76), GGCGATCGCC (SEQ ID NO:77), CGATCGATCG (SEQ ID NO:78), GATCGCGATC (SEQ ID NO:79), GCAACGTTGC (SEQ ID NO:80), GCATCGATGC (SEQ ID NO:81), CAGCGCGCTG (SEQ ID NO:82), GACGTACGTC (SEQ ID NO:83), CTAGCGCTAG (SEQ ID NO:84), CCCGATCGGG (SEQ ID NO:85), GACGGCCGTC (SEQ ID NO:86), GCCGATCGGC (SEQ ID NO:87), TCCGATCGGA (SEQ ID NO:88), ACGTCGACGT (SEQ ID NO:89), ACAACGTTGT (SEQ ID NO:90) and ACGACGTCGT (SEQ ID NO:91). Among them, GCCGATCGGC (SEQ ID NO:87), CCCGATCGGG (SEQ ID NO:85), TCCGATCGGA (SEQ ID NO:88), GGCGATCGCC (SEQ ID NO:77), GACGATCGTC (SEQ ID NO:76), GCATCGATGC (SEQ ID NO:81) and ACGACGTCGT (SEQ ID NO:91 are preferable. The palindrome sequence is not necessarily limited to these specific examples as long as its length is at least 8 nucleotides.

A length of XCGY is 8 to 22 nucleotides, and can be controlled within this range depending on the lengths of each X and Y and the types of a palindrome sequence. The length of XCGY is preferably 8 to 14 nucleotides, more preferably 9 or 10 nucleotides and most preferably 10 nucleotides.

P and Q in the aforementioned formula represent one nucleotide other than guanine. Specifically, they are any of adenine (A), thymine (T) and cytosine (C).

M in the aforementioned formula represents an integer of 6 to 10 and preferably 6 to 8. If M is departed from this range, it is not preferable because the IFN-inducing activity becomes insufficient. N represents an integer of 0 to 3. If N is departed from this range, it is not preferable because the inflammatory cytokine-inducing activity can not be reduced sufficiently.

A full length of the immunostimulatory oligonucleotide of the present invention is 16 to 37 nucleotides, and varies depending on M and N and the lengths of X and Y in the aforementioned formula. When M is in the range of 6 to 8 as described above, the full length is 6 to 35 nucleotides. When the length of XCGY is 9 or 10 nucleotides, the full length is 17 to 23 nucleotides.

Examples of the base sequence of the immunostimulatory oligonucleotide of the present invention may include preferably, but are not necessarily limited to, GOGGGGTGAC-GATCGTCGGG (SEQ ID NO:97:Mod92), GGGGGGT-GACGATCGTCAGGG (SEQ ID NO:28:Mod46), GGGGGGGTCCCGATCGGGAGGG (SEQ ID NO:22:Mod43), GGGGGGGTTCCGATCGGAAGGG (SEQ ID NO:24:Mod44), GGGGGGGTGGCGATCGCCAGGG (SEQ ID NO:26:Mod45), GGGGGGGTGCATCGATGCAGGG (SEQ ID NO:30:Mod47), GGGGGGGTGCCGATCG-GCAGGG (SEQ ID NO:6:Mod53), GGGGGGGGGTGC-CGATCGGCAGGG (SEQ ID NO:7:Mod54), GGGGGGT-GCCGATCGGCAGG (SEQ ID NO:9:Mod40), GGGGGGGTGCCGATCGGCAGG (SEQ ID NO:10:Mod55), GGGGGGGTGCCGATCGGCAG (SEQ ID NO:11:Mod41), GGGGGGGTGCCGATCGGCA (SEQ ID NO:15:Mod61), GGGGGGGGTGCCGATCGGCA (SEQ ID NO:16:Mod62), GGGGGGGGGTGCCGATCGGCA (SEQ ID NO:17:Mod63), GGGGGGGGGGGTGCCGATCGGCA (SEQ ID NO:18:Mod64), GGGGGGGAC-GACGTCGTCGG (SEQ ID NO:40:Mod71) and GGGGG-GAACGACGTCGTTGG (SEQ ID NO:42:Mod73). When M is 7 and N is 2 in 5'-$(G)_M$PXCGYQ$(G)_N$-3' (SEQ ID NO:118), the examples may be GGGGGGGAGCCGATCG-GCTGG (SEQ ID NO:43), GGGGGGGAGCCGATCG-GCAGG (SEQ ID NO:44), GGGGGGGTGCCGATCG-GCTGG (SEQ ID NO:45), GGGGGGGAGCCGATCGGCCGG (SEQ ID NO:46), GGGGGGGCGCCGATCGGCCGG (SEQ ID NO:47), GGGGGGGTGACGATCGTCAGG (SEQ ID NO:48:Mod84), GGGGGGGTGACGATCGTCTGG (SEQ ID NO:49), GGGGGGGAGACGATCGTCAGG (SEQ ID NO:50:Mod85), GGGGGGGAGACGATCGTCTGG (SEQ ID NO:51:Mod83), GGGGGGGTGACGATCGTCAGG (SEQ ID NO:52:Mod87), GGGGGGGTGACGATCGT-TAGG (SEQ ID NO:53), GGGGGGGTCGACGTCGTGG (SEQ ID NO:100), GGGGGGGACGACGTCGTGG (SEQ ID NO:101), GGGGGGGTCGACGTCGAGG (SEQ ID NO:102) and GGGGGGGACGACGTCGTCGG (SEQ ID NO:105). Furthermore when M is 7 and N is 3, the examples may be GGGGGGGCGACGATCGTCGGG (SEQ ID NO:54), GGGGGGGTGACGATCGTCGGG (SEQ ID NO:94), GGGGGGGTCGACGTCGTGGG (SEQ ID NO:99) and GGGGGGGTCGACGTCGAGGG (SEQ ID NO:107). When M is 8 and N is 1, the examples may be GGGGGGGGGCGACGATCGTCG (SEQ ID NO:95;Mod93), GGGGGGGGGTGACGATCGTCG (SEQ ID NO:96), GGGGGGGGGACGACGTCGTG (SEQ ID NO:103) and GGGGGGGGGTCGACGTCGAG (SEQ ID NO:104). When M is 8 and N is 0, the example may be GGGGGGGG-GACGACGTCGTC (SEQ ID NO:106).

As specifically shown in the following examples, in the oligonucleotides composed of the base sequences represented by SEQ ID NOS:6, 7, 9 to 11, 15 to 18, 22, 24, 26, 28, 30, 40, 42, 48, 50 to 52, 54, 95 and 97 in Sequence Listing, it has been demonstrated that the IFN-inducing activity is further augmented and the inflammatory cytokine-inducing activity is further reduced compared with the D-type CpG sequences which satisfy the condition of PXCGYQ and do not satisfy the other condition in the aforementioned formula. That is, the palindrome sequence including a CpG motif in oligonucleotides is essential for the IFN-inducing activity, but the number of the bases in the poly-G sequence inserted outside thereof is important for both the augmentation of the IFN-inducing activity and the reduction of the inflammatory cytokine-inducing activity. Therefore, the most important thing in the present invention is not the combination of the poly-G sequence with the particular palindrome sequence, but the insertion mode of the optimal poly-G sequence. Among the oligonucleotides listed above, the oligonucleotide composed of the base sequences of SEQ ID NOS:6, 7, 10, 15 to 17, 24, 26, 28, 48 and 50 to 52, among them, especially SEQ ID NOS:6, 7, 10, 28, 48 and 50 to 52 have the strong interferon (IFN)-inducing activity are particularly preferable.

In the immunostimulatory oligonucleotide of the present invention, all or a part of internucleotide phosphodiester bonds, a ribose sugar moiety and a base moiety of each nucleotide may be chemically modified. But, a methylation to cytosine in XCGY is not preferable because an immunostimulatory activity is lost. A suitable embodiment of the modified immunostimulatory oligonucleotide of the present invention in this way is the substitution and/or modification of an oxygen atom in a phosphoric acid group in the internucleotide phosphodiester bond, and may include phosphorothioate, methylphosphonate and phosphoramidate. A phosphorothioate modification is preferably made in all or the part of the internucleotide phosphodiester bonds in the 5' terminal poly-G sequence [$(G)_M$ in the aforementioned formula)]. In the 5' terminal poly-G sequence, it is preferable that the phosphorothioate modification is made in all internucleotide phosphodiester bonds or in the phosphodiester bond at an extreme terminus. For the 3'-terminal poly-C sequence, it is preferable that a phosphorothioate modification is made in a part or all of the internucleotide phosphodiester bonds except for the base at the extreme terminus. In the oligonucleotides where N=0 or 1 in the aforementioned general formula, the phosphorothioate modification may be given to the phosphodiester bonds except guanine in the 3' terminal side. Further, it is preferable that the phosphodiester bonds in the poly-G sequence at the 5' terminal side and in the extreme terminus at the 3' terminal side are modified with phosphorothioate. Furthermore, as long as the oligonucleotide has an immunostimulatory activity, the chemical modification other than the methylation may be given to cytosine (C in the center of the aforementioned formula) of CpG dinucleotides.

A degradation of the oligonucleotide having a phosphodiester skeleton is mediated by exonuclease and endonuclease. It is known that the resistance to these nucleases is acquired by modifying an internucleotide bond with phosphorothioate. Examples of the oligonucleotide having some internucleotide modifications may include the oligonucleotides having phosphorothioate modifications in 5' and 3' terminal internucleotide bonds and the oligonucleotides having phosphorothioate modifications in internucleotide bonds of a poly-G sequence, which have a resistance to exonuclease. The oligonucleotide having phosphorothioate modifications in all internucleotide bonds has a resistance to exonuclease and endonuclease. The nuclease-resistant CpG-oligonucleotide is stable, for example, prolongs the time period for acting upon a target receptor and keeps a constant concentration, and consequently augments the immunostimulatory activity.

The aforementioned immunostimulatory oligonucleotide of the present invention may bind a molecule other than the nucleic acid, if the requirement for the base sequence described above is satisfied as long as it has the immunostimulatory activity, specifically, the augmented IFN-inducing activity and the reduced inflammatory cytokine-inducing activity.

In the present invention, that the immunostimulatory oligonucleotide has the immunostimulatory activity means that the interferon (IFN)-inducing activity is augmented and the inflammatory cytokine-inducing activity is reduced, Here, the inflammatory cytokine means interleukin-12 (hereinafter, IL-12), tumor necrosis factor-$\alpha$ (hereinafter, TNF-$\alpha$), interleukin-6 (hereinafter, IL-6) and interleukin-1$\beta$ (hereinafter, IL-1$\beta$). An inflammatory refers to a property to induce the fever in a tissue, and to elicit infiltration and activation of the cells. Meanwhile, an immunosuppressive property indicates having a function or a nature to suppress the inflammatory reaction described above. Interleukin-10 (hereinafter, IL-10) is one of immunosuppressive cytokines, and is functionally different from the inflammatory cytokines. An IFN-inducing activity or an inflammatory cytokine-inducing activity indicates an action to induce the production of cytokines from, for examples in the human, peripheral blood mononuclear cells (hereinafter, PBMC) of human specimens having a normal reactivity, and for example in the mouse, bone marrow-derived dendric cells or splenic cells or monocytic cell lines J744 or RAW264 sensitive to an immunostimulatory oligonucleotide having a CpG sequence. In the present invention, it can be shown as the activity indicated by inducement to produce IFN-$\alpha$ and IFN-$\gamma$ from the human peripheral blood mononuclear cells (hereinafter, PBMC) by treating with the immunostimulatory oligonucleotide. Also, it can be shown as the activity indicated by inducement to produce IFN-$\gamma$ and IL-10 from the murine splenic cells by treating with the immunostimulatory oligonucleotide. Furthermore, it can be shown as the activity indicated by inducement to produce interleukin-12 p40 (hereinafter, IL-12 p40) and TNF-$\alpha$ from murine dendritic cells and a J774 cell line by treating with the immunostimulatory oligonucleotide. In the present invention, the augmented IFN-inducing activity, which is used when the activities of several immunostimulatory oligonucleotide sequences are compared, means that when the above cells are stimulated with the immunostimulatory oligonucleotide, a larger amount of the production of IFN-$\alpha$ and IFN-$\gamma$ is induced by lower concentrations of the oligonucleotides compared with the other. Meanwhile, the reduced inflammatory cytokine-inducing activity means that when the above cells are stimulated with the immunostimulatory oligonucleotide, a smaller amount of the production of IL-12 p40 and TNF-$\alpha$ is induced.

A specific method of tests to evaluate the IFN-$\alpha$ and IFN-$\gamma$-inducing activity in vitro in PBMC by the immunostimulatory oligonucleotide of the present invention is shown below. PBMC are isolated from human blood by density gradient centrifugation at 2,000 rpm at room temperature for 25 minutes using Histopaque 1077. The isolated PBMC are suspended at $4.0 \times 10^6$ cells per mL in RPMI 1640 medium containing 10% FCS, and then, seeded in a round-bottomed 96-well microplate at $4.0 \times 10^5$ cells per well, and stimulated in the presence of the immunostimulatory oligonucleotide for 24 hours or 7 days. Then, each culture supernatant is collected. The amounts of produced IFN-$\alpha$ and IFN-$\gamma$ are quantified by ELISA using the culture supernatants stimulated for 24 hours and 7 days.

The specific method of tests to evaluate the IL-12 and TNF-$\alpha$-inducing activity in vitro from PBMC by the immunostimulatory oligonucleotide of the present invention is shown below. PBMC are isolated from human blood by density gradient centrifugation at 2,000 rpm at room temperature for 25 minutes using Histopaque 1077. The isolated PBMC are suspended at $2.0 \times 10^6$ cells per mL in RPMI 1640 medium containing 10% FCS, and then, seeded in a flat-bottomed 96-well microplate at $2.0 \times 10^5$ cells per well, and stimulated in the presence of the immunostimulatory oligonucleotide for 8 hours or 24 hours. Then, each culture supernatant is collected. The amounts of produced IL-12 and TNF-$\alpha$ are quantified by ELISA using the culture supernatants stimulated for 8 hours and 24 hours.

The procedure to identify the presence or absence of the induction of IFN-$\gamma$ and IL-10 production from the murine splenic cells by the immunostimulatory oligonucleotide of the present invention may include an induction evaluation test in vitro. The specific method is shown below. The spleen is removed from a male C57BL/6N mice aged 10 to 25 weeks, and transferred into a petri dish in which RPMI 1640/10% FCS has been placed. The spleen is mashed using two partially scabrous glass slides, the mashed spleen is strained through a cell strainer and the filtrated splenic cells are transferred to a round bottomed centrifuge tube. The transferred sample is centrifuged at 1,000 rpm at 4° C. for 10 minutes, the supernatant is discarded, and then 5 mL of hemolysis buffer (prepared by mixing 0.83% $NH_4Cl$ and 170 mM Tris-HCl, pH 7.65 at 9:1) is added, and then a cell pellet is flaked by pipetting to suspend the cells. After incubating at room temperature for 5 minutes, 5 mL of the medium is added thereto, and mixed upside down, and the mixture is centrifuged at 1,000 rpm at 4° C. for 10 minutes. The supernatant is discarded, and the cell pellet is flaked by pipetting to suspend the cells. After washing the cells twice, the cells are resuspended in the medium, a cell number is counted using trypan blue, and the cells are prepared to be at $4 \times 10^6$ viable cells per mL. The cells are seeded at $4.0 \times 10^5$ cells per well in a round-bottomed 96-well microplate, and stimulated with the immunostimulatory oligonucleotide for 3 days. After the stimulation, the concentrations of IFN-$\gamma$ and IL-10 in the culture supernatant are quantified by ELISA.

The procedure to identify the presence or absence of the induction of IL-12 p40 and TNF-$\alpha$ production in J774 cell line by the immunostimulatory oligonucleotide of the present invention may include an induction evaluation test in vitro. The J774 cells are adjusted to $1 \times 10^6$ cells per mL using the medium (RPMI 1640, 10% FCS, 50 $\mu$M 2-ME). The cells are seeded at $1.0 \times 10^5$ cells per well in a flat bottomed 96-well multiplate and stimulated with the immunostimulatory oligonucleotide for 4 hours, 8 hours or 48 hours. After the stimulations the concentrations of IL-12 p40 and TNF-$\alpha$ in the culture supernatant are quantified by ELISA.

The immunostimulatory oligonucleotide of the present invention can be synthesized by the conventional technology and a nucleic acid synthesizer. These synthesis methods include enzymatic methods, chemical methods and a degradation of a longer sequence than the sequence of the present invention, but are not necessarily limited thereto. The modified oligonucleotide is also synthesized by the conventional technology. For example, the oligonucleotide modified with phosphorothioate is obtained by treating oligonucleotide phosphoramidate with sulfur, but it is not necessarily limited thereto. The synthesis technology and the modification technology to obtain oligonucleotides are also used in Patent Documents and Non-patent Literatures cited herein, in addition, publicly known technologies are confirmed in many reports.

The immunostimulatory oligonucleotide of the present invention described above may be in a form of an oligonucleotide complex for the purpose of the use as pharmaceuticals. As the complex, a mixture or a binding body of the immunostimulatory oligonucleotide with the other substance (e.g., including cytokines, peptides, antigens composed of the protein or non-protein), or a colloid dispersion system or a lipid base system in which the immunostimulatory oligonucleotide has been incorporated may be used. The colloid dispersion system may include polymer complexes, nanocapsules, microspheres and beads. As the lipid base system, for example, an oil in water type emulsifiers, micelles, mixed micelles and liposomes may be selected, but the lipid base system is not necessarily limited thereto. In the suitable embodiment, the above complex is the liposome in which the immunostimulatory oligonucleotide has been embedded and sealed. Embedding and sealing indicate binding to a lipid membrane surface of the liposome, uptaking into a lipid membrane or uptaking in a lumen of the liposome. The liposome may be modified with or bound to particular functional molecule(s), e.g., monoclonal antibody, sugar, glycolipid or protein.

As lipid(s) which composes the liposome, any lipids known for composing the liposome and commonly used can be used alone or in combination of two or more. For example, natural products, e.g., egg yolk, soybeans or the other lipids obtained from animals or plants, and these lipids can be used by hydrogenating to reduce an unsaturation degree. Specifically, for example, sterols (e.g., cholesterol), phosphatidyl ethanolamines (e.g., dipalmitoyl phosphatidyl ethanolamine, distearoyl phosphatidyl ethanolamine), phosphatidyl inositols, phosphatidyl cholines (e.g., dipalmitoyl phosphatidyl choline, distearoyl phosphatidyl choline), phosphatidyl glycerols, phosphatidyl serines (e.g., dipalmitoyl phosphatidyl serine, distearoyl phosphatidyl serine), phosphatidic acids (dipalmitoyl phosphatidic acid, distearoyl phosphatidic acid), sphingomyelins and cardiolipin are included, but are not limited thereto.

The liposome is prepared by using the publicly known method. A vortex method and an ultrasonic method are common. In addition, an ethanol injection method, an ether method, a mechanochemical method, a warming method, a lipid dissolution method and a reverse phase evaporation method can be applied, and can be used in combination. For example, in the vortex method and the ultrasonic method, a predetermined lipid is dissolved in an organic solvent, e.g., methanol, ethanol, chloroform or the mixture thereof, e.g., the mixture of methanol and chloroform, and subsequently the organic solvent is evaporated and removed to yield a thin film of the lipid. At that time, by dissolving the above lipids in various combinations at concentration ratios in the organic solvent, it is possible to produce various liposomes. Subsequently, an aqueous medium is added to this thin film of the lipid and the vortex treatment or the ultrasonic treatment is given thereto to form the liposome. At that time, by mixing, dissolving or suspending a substance to be embedded and sealed in the liposome in the above aqueous medium, it is possible to embed and seal a substance in the liposome. The concentration of the substance to be embedded and sealed, which is dissolved in an aqueous medium, is not particularly limited, and it is preferably 0.00375 to 375 mg/mL for the protein and 0.5 to 5,000 μg/mL for the immunostimulatory oligonucleotide. Generally, a particle diameter of the liposome is preferably in the range of 0.01 to 10 μm.

The above immunostimulatory oligonucleotide of the present invention can be used as an active ingredient of the pharmaceuticals for various uses. A suitable indication in one embodiment may include allergic diseases. The allergic disease is caused by an antigenic substance derived from pollens, mites, animals such as dogs and cats, foods and house dusts, and the allergic disease has a symptom of an inflammation such as rhinitis, conjunctivitis, dermatitis and asthma. The more suitable embodiment may include the use as the active ingredient of a therapeutic or preventive agent for pollen allergy among the above allergic diseases. As pollen allergies, the allergy caused by proteins derived from cedar pollens as an antigen is common, but antigens may be the substance derived from the other pollens of Japanese cypress, white birch, alder, ragweed, tansy and cocksfoot.

For example, when the murine splenic cells sensitized with the cedar pollen antigen are stimulated with the cedar pollen antigen, the production of IL-5 and IL-4, which are the indicator of an antigen specific Th2 response, is typically induced and it is not demonstrated that the production of IFN-γ, which is the indicator of a Th1 response, is induced. However, when the cells are stimulated with the cedar pollen antigen simultaneously with the immunostimulatory oligonucleotide of the present invention, it is demonstrated that the production of IFN-γ is effectively induced. When the mouse is treated with the immunostimulatory oligonucleotide of the present invention and subsequently the Th2 response is elicited with the mixture of the antigen and alum, it is demonstrated that the production of antigen specific IgE in serum is suppressed and the level of antigen specific IgG2a is increased. By this test method, the therapeutic effect on asthma can be demonstrated when an asthma-inducing antigen is used as the antigen treating for a sensitization and a therapy.

Therefore, the above immunostimulatory oligonucleotide of the present invention exhibits high therapeutic and preventive effects on various allergic symptoms.

The above immunostimulatory oligonucleotide of the present invention can be used as a single agent, or as the therapeutic agent for a hyposensitization therapy by using together with the above allergen.

Furthermore, the immunostimulatory oligonucleotide of the present invention has an action to suppress a production of IgE in human cells. As the procedure to identify such an action, a specific method of the test to evaluate the activity of suppressing the production of IgE in vitro is shown below. PBMC isolated from the human blood by the method described above are prepared at $4.0 \times 10^6$ cells per mL in RPMI 1640 containing 10% FCS, and then seeded at $4.0 \times 10^5$ cells per well in the flat bottomed 96-well microplate. The cells are stimulated with human IL-4 and anti-CD40 antibody together with the immunostimulatory oligonucleotide for 14 days, and then the culture supernatant is collected. The amount of produced IgE is quantified by ELISA.

The suitable indication in an embodiment of the present invention may be a vaccine containing the immunostimulatory oligonucleotide of the present invention as an adjuvant. Diseases for which the vaccine can be used are infections and allergies. An infection is caused by viruses, bacteria, fungi and protozoa, but the cause is not necessarily limited thereto.

Typically, a vaccine refers to an antigenic suspension or solution which is administrated to a patient to generate an active immunity, and which contains an infectious factor, a specific part of the infectious factor or a factor derived from animals or plants. An antigenic portion which composes the vaccine may be any of a protein, a peptide, a lipid, a polysaccharide or a nucleic acid. The preferable embodiment is not particularly limited, and is a mixed solution of the immunostimulatory oligonucleotide of the present invention and the vaccine. It may be the complex of the immunostimulatory oligonucleotide of the present invention with the antigenic portion of the vaccine.

Furthermore, the suitable applicable symptom for one embodiment is hepatitis, specifically hepatitis with activation of immune system, non-viral hepatitis and/or viral hepatitis, and more preferably hepatitis C and/or hepatitis B caused by infection with HBV and/or HCV.

Symptoms of the infection with HBV and/or HCV in the present specification include the symptoms caused by acute and chronic hepatitis. The clinical symptoms of viral hepatitis include, but are not necessarily limited to, jaundice, abdominal pain, fatigue, nausea and emesis, as well as clinical/laboratory hepatitis associated-findings such as elevated levels of hepatic enzymes (e.g., alanine aminotransferase [ALT], aspartic acid aminotransferase [AST] and/or lactic acid dehydrogenase [LDH]), elevation of hilirubin level, HCV viremia or elevation of an antigenic level, portal hypertension and anorexia.

The therapeutic effect of the immunostimulatory oligonucleotide of the present invention for hepatitis B and/or hepatitis C can be evaluated by examining the above clinical symptoms (jaundice, fatigue, abdominal pain), hepatitis-associated laboratory findings (e.g., levels of hepatic enzymes in blood), amplification and replication of virus, or the amount of the virus (titer) as the indicators. That is, comparing individual not treated with the present invention with an individuals treated with the immunostimulatory oligonucleotide of the present invention, disappearance, remission and amelioration of the clinical symptoms of hepatitis B and/or hepatitis C, or reduction of symptomatic levels, and further shortening of a diseased period can be expected. The therapeutic effect could be reflected in the hepatitis-associated laboratory findings, the replication of virus and the viral amount. A decrease of the viral titer includes an elimination of the virus from an infected site or individual.

A method of evaluation may be selected from detection of the symptoms, measurement of hepatic functions by clinical examinations, hepatic biopsy, direct or indirect measurement of portal vein pressure, and the measurement of viral particles, viral nucleic acids and viral antigen titers, and any procedure known in the art including the detection and the measurement of anti-viral antibody. Subjective physical symptoms such as abdominal pain and fatigue are determined by the presence or absence of the symptom, and jaundice is determined by qualitative base and quantified by measuring the level of bilirubin in blood or serum. The laboratory findings for hepatitis, for example, the levels of the hepatic enzyme, AST and ALT in blood or serum, are measured by hematological, biochemical and histological tests. The viral titer in blood or serum sample is measured by the methods well-known in the art, e.g., quantification of the viral particles (e.g., by separation or visualization, or assay of DNase resistant particles), the detection of viral antigen in the blood or serum sample (quantification of antigen amount by ELISA), the detection of viral antibody in the blood or serum sample, or the detection of viral nucleic acids (RNA and DNA) (PCR amplification using HCV gene specific primers or in situ hybridization using a viral specific probe). A biopsy sample from hepatic tissue can also be evaluated by the above methods.

Subjects to be treated by the above therapeutic agent of the present invention are vertebrate animals, preferably mammalian animals and more preferably human beings. The vertebrate animals other than the human being may include, but are not necessarily limited to, dogs, cats, horses, cattle, swines, sheeps, goats, chickens, monkeys, rats or mice.

The immunostimulatory oligonucleotide of the present invention may be administered to individuals likely infected with HBV and/or HCV (e.g., cases of having no physical symptom and an embryo in a mother carrying HCV), to individuals confirmed to be infected with HBV and/or HCV, and to individuals with the above clinical symptoms of hepatitis B and/or hepatitis C (e.g., including chronic hepatitis or acute hepatitis due to early infection or recurrence after chronic infection). Frequency of administration of the immunostimulatory oligonucleotide varies depending on degrees of the infection with HBV and/or HCV or the symptoms thereof. The treatment using the immunostimulatory oligonucleotide may be used for the individuals where a treatment such as interferon therapy (and its effect) was insufficient or unsuccessful. Furthermore, the immunostimulatory oligonucleotide may be administered once or multiple times.

In the case of using a preventive or therapeutic agent for allergic diseases and hepatitis, its administration route is not particularly limited, and is preferably subcutaneous injection, intradermal injection, intravenous injection, intramuscular injection, injection to diseased tissue, oral administration, nasal administration, transocular administration, laryngeal administration, lung administration, percutaneous administration and sublingual administration. A dosage is appropriately selected depending on a condition of a patient, a therapeutic purpose and an administration route, and is typically 0.1 pmol to 10 µmol and preferably 1 pmol to 1 µmol per adult per day as the amount of the oligonucleotide. When administered as the adjuvant, a dosage is also appropriately selected depending on a therapeutic purpose and an administration route, and may be typically almost the same dosage as the above. The immunostimulatory oligonucleotide of the present invention is typically formulated by a well-known method of formulating into a dosage form to be employed.

These immunostimulatory oligonucleotides can be used as a therapeutic or preventive agent for allergic diseases, an adjuvant of a vaccine and a therapeutic or preventive agent for hepatitis, and can also be used as a method for treating or preventing allergic diseases, a method for utilizing as an adjuvant for the vaccine or the method for treating or preventing hepatitis.

EXAMPLES

Examples will be described in detail below. But, the technical scope of the present invention is not limited to these Examples.

Abbreviations and properties of the sequences of the immunostimulatory oligonucleotides used in the following description are described in Sequence Listing. The sequences, the abbreviations and the properties of the publicly known immunostimulatory oligonucleotides described in Examples were shown in Table 1.

Table 1

TABLE 1

PUBLICLY KNOWN IMMUNOSTIMULATORY OLICONUCLEOTIDES [ODN]

| ODN ABBREVIATION | (SEQ ID NOS) | SEQ ID NOS IN PATENT OR NONPATENT DOCUMENT | | MODIEICATION |
|---|---|---|---|---|
| Mod2 | (SEQ ID NO: 1) | WO2006/035939 | SEQ ID NO: 1 | PHOSPHOROTHIOATE MODIF. TO INTERNUCLEOTITDE BONDS OF POLY-G AT 5' AND 3' TERMINUS |
| Mod33 | (SEQ ID NO: 5) | WO2006/035939 | SEQ ID NO: 14 | PHOSPHOROTHIOATE MODIF. TO INTERNUCLEOTITDE BONDS OF POLY-G AT 5' AND 3' TERMINUS |
| Mod39 | (SEQ ID NO: 27) | WO2006/035939 | SEQ ID NO: 18 | PHOSPHOROTHIOATE MODIF. TO INTERNUCLEOTITDE BONDS OF POLY-G AT 5' AND 3' TERMINUS |
| I1 | (SEQ ID NO: 35) | J P 10-506265 | SEQ ID NO: 1 | PHOSPHOROTHIOATE MODIF. TO INTERNUCLEOTITDE BONDS OF POLY-G AT 5' AND 3' TERMINUS |
| D19 | (SEQ ID NO: 29) | WO2000/061151 | SEQ ID NO: 72 | PHOSPHOROTHIOATE MODIF. TO INTERNUCLEOTITDE BONDS OF POLY-G AT 5' AND 3' TERMINUS |
| 2006 | (SEQ ID NO: 31) | J P 2001-503267 WO1998/018810 | SEQ ID NO: 56 SEQ ID NO: 56 | PHOSPHOROTHIOATE MODIF. TO ALL INTERNUCLEOTIDE BONDS |
| 2395 | (SEQ ID NO: 32) | WO2003/015711 | SEQ ID NO: 1 | PHOSPHOROTHIOATE MODIF. TO ALL INTERNUCLEOTIDE BONDS |
| 1018 | (SEQ ID NO: 33) | J P 2002-517156 J P 2002-500159 | SEQ ID NO: 2 SEQ ID NO: 19 | PHOSPHOROTHIOATE MODIF. TO ALL INTERNUCLEOTIDE BONDS |
| C274 | (SEQ ID NO: 34) | WO2004/058179 | SEQ ID NO: 27 | PHOSPHOROTHIOATE MODIF. TO ALL INTERNUCLEOTIDE BONDS |
| G9-GACGATCGTC-G1 | (SEQ ID NO: 36) | J P 2005-237328 | SEQ ID NO: 7 | NONE |
| G7-GACGATCGTC-G3 | (SEQ ID NO: 98) | J P 2005-237328 | SEQ ID NO: 5 | NONE |
| G1-GACGATCGTC-G9 | (SEQ ID NO: 55) | J P 2005-237328 | SEQ ID NO: 1 | NONE |
| M26 | (SEQ ID NO: 37) | KR2001-063153 | SEQ ID NO: 11 | NONE |
| M27 | (SEQ ID NO: 38) | KR2001-063153 | SEQ ID NO: 12 | NONE |
| M26-GS | (SEQ ID NO: 37) | KR2001-063153 | SEQ ID NO: 11 | PHOSPHOROTHIOATE MODIF. TO INTERNUCLEOTITDE BONDS OF POLY-G AT 5' AND 3' TERMINUS |
| M27-GS | (SEQ ID NO: 38) | KR2001-063153 | SEQ ID NO: 12 | PHOSPHOROTHIOATE MODIF. TO INTERNUCLEOTITDE BONDS OF POLY-G AT 5' AND 3' TERMINUS |
| G10 | (SEQ ID NO: 56) | WO2005/014110 | SEQ ID NO: 3 | NONE |
| G3-6 | (SEQ ID NO: 57) | WO2005/014110 | SEQ ID NO: 6 | NONE |
| 2332 | (SEQ ID NO: 58) | J P 2003-510290 | SEQ ID NO: 35 | PHOSPHOROTHIOATE MODIF. TO INTERNUCLEOTITDE BONDS OF POLY-G AT 5' AND 3' TERMINUS |

MODIF.: MODIFICATION

Example 1

Comparison of Base Numbers of 5' Terminal Poly-G Sequences Essential for the IFN-Inducing Activity in Human PBMC Among Immunostimulatory Oligonucleotides CpG oligonucleotides to which the poly-G sequence composed of various numbers of bases had been inserted were synthesized, and a length of the bases essential for IFN-inducing activities was examined. Twenty immunostimulatory oligonucleotides (SEQ ID NOS:1 to 20) were constructed by inserting the oligonucleotide containing the poly-G sequence modified with phosphorothioate in both terminal sides or only in the 5'-terminal side outside the palindrome sequence TGCCGATCGGCA (SEQ ID NO:116) containing the palindrome sequence CGATCG (SEQ ID NO:59) (Sequences 49 and 15 in JP Hei-4-352724-A) shown by Tokunaga et al. Mod2 (SEQ ID NO:1) and Mod33 (SEQ ID NO:5) have been shown to have IFN-inducing activity in International Publication No. 20061035939 Pamphlet. Further, the oligonucleotides composed of these constructed-sequences were screened for having the activity of inducing the production of IFN-α and IFN-γ in human PBMC (FIGS. 1-1 to 1-6, Table 2). The activity of inducing the production of IFN-α and IFN-γ was evaluated, according to the procedure and conditions shown as the specific method of a test for evaluating the in vitro activity of inducing the production of IFN-α and IFN-γ in human PBMC, based on the amount produced in the culture supernatant obtained by stimulating for 24 hours and 7 days.

Table 2

TABLE 2

IFN PRODUCTION AMOUNT IN HUMAN PBMC

| Name | Sequence 5'-3' | (SEQ ID NO) | IFN-α PRODUCTION AMOUNT [pg/mL] | IFN-γ PRODUCTION AMOUNT [pg/mL] |
|---|---|---|---|---|
| Mod2 | ggTGCCGATCGGCAGggggC | (SEQ ID NO: 1) | 749.08 ± 171.94 | 1651.96 ± 553.15 |
| Mod52 | gggTGCCGATCGGCAGgG | (SEQ ID NO: 2) | 0 | 210.32 ± 70.72 |
| Mod51 | ggggTGCCGATCGGCAGgG | (SEQ ID NO: 3) | 0 | 307.38 ± 168.47 |
| Mod42 | gggggTGCCGATCGGCAGgG | (SEQ ID NO: 4) | 188.45 ± 49.64 | 1058.77 ± 34.67 |
| Mod53 | ggggggTGCCGATCGGCAGgG | (SEQ ID NO: 6) | 2986.90 ± 312.97 | 3877.35 ± 3677.68 |

TABLE 2-continued

IFN PRODUCTION AMOUNT IN HUMAN PBMC

| Name Sequence 5'-3' (SEQ ID NO) | | IFN-α PRODUCTION AMOUNT [pg/mL] | IFN-γ PRODUCTION AMOUNT [pg/mL] |
|---|---|---|---|
| Mod54ggggggggTGCCGATCGGCAGgG | (SEQ ID NO: 7) | 3604.07 ± 74.79 | 2942.62 ± 967.95 |
| Mod56ggggTGCCGATCGGCAgG | (SEQ ID NO: 8) | 843.31 ± 128.25 | 1407.49 ± 546.66 |
| Mod40gggggTGCCGATCGGCAgG | (SEQ ID NO: 9) | 1031.75 ± 411.33 | 1864.08 ± 510.72 |
| Mod55gggggggTGCCGATCGGCAgG | (SEQ ID NO: 10) | 4409.68 ± 411.82 | 3999.59 ± 2475.58 |
| Mod41gggggTGCCGATCGGCaG | (SEQ ID NO: 11) | 1022.33 ± 253.36 | 2525.58 ± 783.73 |
| Mod49ggggggTGCCGATCGGCAGggggG | (SEQ ID NO: 13) | 1955.15 ± 403.32 | 2094.17 ± 475.09 |
| Mod50ggggggTGCCGATCGCAGggggG | (SEQ ID NO: 14) | 4739.47 ± 212.16 | 3453.13 ± 146.83 |

The amounts of produced IFN shown in Table 2 were obtained when the concentration of the immunostimulatory oligonucleotide was 100 nM (final concentration). Lowercase letters in the sequences in Tables and Figs. represent the bases modified with phosphorothioate.

Figures 1, 2:
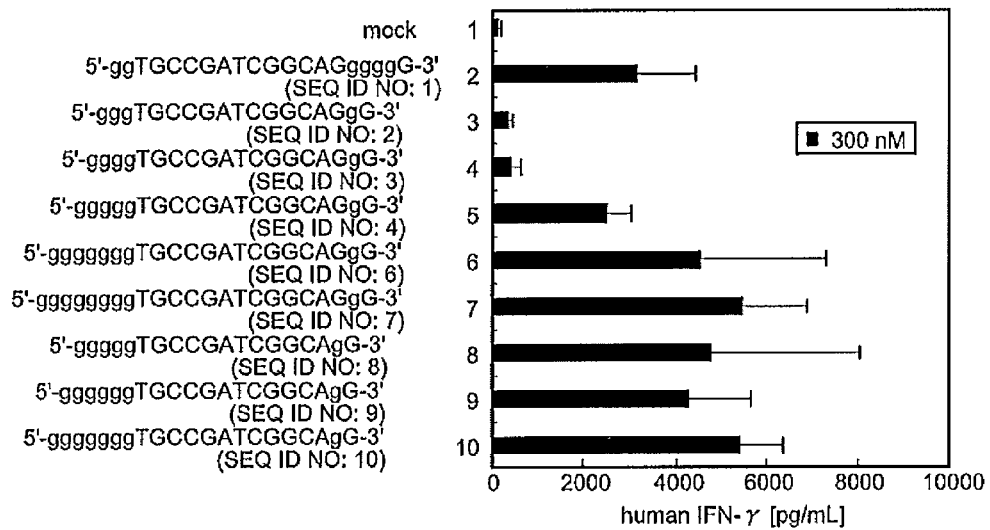

FIGS. 1-1 and 1-2 show the amounts of IFN-α produced when the oligonucleotide concentration was 100 nM (final concentration) of Mod2 (SEQ ID NO:1, Lane 2), Mod52 (SEQ ID NO:2, Lane 3), Mod51 (SEQ ID NO:3, Lane 4), Mod42 (SEQ ID NO:4, Lane 5), Mod53 (SEQ ID NO:6, Lane 6), Mod54 (SEQ ID NO:7, Lane 7), Mod56 (SEQ ID NO:8, Lane 8), Mod40 (SEQ ID NO:9, Lane 9) or Mod55 (SEQ ID NO:10, Lane 10), and the amounts of IFN-γ produced when the oligonucleotide concentration was 300 nM (final concentration) of the same sequences, respectively. Concerning the IFN-α-inducing activity (Table 2 and FIG. 1-1), in the group having 3 bases (N=3) (Lanes 3 to 7 in FIG. 1-1) of a poly-G sequence at the 3' terminus, the activity was high when the oligonucleotides had 6 or more bases (M is 7 or more) (Lanes 6 and 7) of a poly-G sequence at the 5'-terminus. In the group having 2 bases (N=2) of a poly-G sequence at the 3' terminus (Lanes 8 to 10), the activity was high when they had 6 or more bases of a poly-G sequence at the 5' terminus (Lanes 9 and 10). Comparing with Mod2 (M=2/N=6, Lane 2) having the structure of a typical CpG sequence, the activity of Mod52 (M=3/N=3, Lane 3), Mod51 (M=4/N=3, Lane 4) or Mod42 (M=5/N=3, Lane 5) was attenuated or was completely lost. Thus, it was found that the oligonucleotide having the enhanced IFN-α-inducing activity was not always obtained only by designing sequences by changing the numbers of bases from 4 to 6 of the poly-G sequences in Mod2. Concerning the IFN-γ-inducing activity (FIG. 1-2), a similar tendency was observed except for Mod56 (SEQ ID NO:8, M=5/N=2, Lane 8). In particular, the IFN-γ-inducing activity of Mod53 (M=7/N=3, Lane 6), Mod54 (M=8/N=3, Lane 7) or Mod55 (M=7/N=2, Lane 10) was significantly enhanced compared with that of Mod2 having 6 bases of the poly-G sequence at a 3' terminus (t-test, p<0.01). This result indicates that, an IFN-γ-inducing activity of oligonucleotides depends on the 5' terminal side and the poly-G sequence is required to have a length of at least 6 or more bases.

Subsequently, in order to elucidate the relation between a length of the poly-G sequence at the 5' terminus and IFN-inducing activity, the IFN-γ-inducing activity was evaluated for the oligonucleotides obtained by inserting up to 20 bases of a poly-G sequence into the 5' terminus (FIGS. 1-3 and 1-4).

Figures 1, 2, 3:
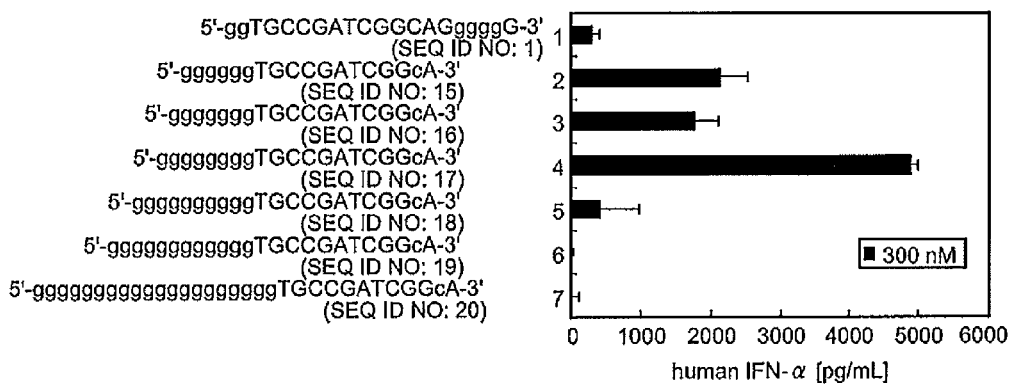

FIGS. 1-3 and 1-4 show the amounts of IFN-α and IFN-γ produced when the oligonucleotide concentration was 300 nM of Mod2 (Lane 1), Mod61 (SEQ ID NO:15, Lane 2), Mod62 (SEQ ID NO:16, Lane 3), Mod63 (SEQ ID NO:17, Lane 4), Mod64 (SEQ ID NO:18, Lane 5), Mod65 (SEQ ID NO:19, Lane 6) or Mod66 (SEQ ID NO:20, Lane 7). As a result, at a concentration of 300 nM, the IFN-α-inducing activity of the oligonucleotides having up to 8 bases of poly-G sequences was significantly enhanced (FIG. 1-3, M=6 to 8/n=0, Lanes 2 to 4), and the oligonucleotide having 10 bases of a poly-G sequence (M=10/N=0) showed slightly higher activity than that of Mod2 (FIG. 1-3, Lane 5). Meanwhile, the oligonucleotides having 12 or more bases of poly-G sequences (M=12 or 20/N=0) lost the most activities (Lanes 6 and 7). In the IFN-γ-inducing activity, the similar tendency to the IFN-α-inducing activity was observed, but the oligonucleotides having even 12 or more bases of poly-G sequences had activities equivalant to Mod2 having a conventional D-type CpG sequence (FIG. 1-4, Lanes 1, 6 and 7).

Furthermore, the relation between the base number of a poly-G sequence at the 3' terminus and the IFN-inducing activity was evaluated. FIGS. 1-5 and 1-6 show the amounts of IFN-α produced when the oligonucleotide concentration was 100 nM (final concentration) of Mod2 (Lane 2), Mod50 (SEQ ID NO:14, lane 3), Mod49 (SEQ ID NO:13, Lane 4), Mod40 (Lane 5) or Mod41 (SEQ ID NO:11, Lane 6), and the amounts of IFN-γ produced when the oligonucleotide concentration was 300 nM (final concentration) of the same sequences, respectively. When the length of a poly-G sequence at the 5' terminus was changed from 2 bases (Mod2: M=2/N=6, Lane 2) to 6 bases (Mod50: M=6/N=6, Lane 3), the amounts of produced IFN-α and IFN-γ was increased (Table 2, FIGS. 1-5 and 1-6) to the levels equivalent to Mod55 (M=7/N=2, see Lane 10 in FIGS. 1-1 and 1-2). The IFN-α-inducing activity of the oligonucleotides having 6 bases of poly-G sequences at a 5' terminus (M=6/N=0 to 6) tended to depend on the length of poly-G sequences at the 3' terminus, but was not lost completely and exceeded the activity of Mod2 (Lanes 3 to 6 in FIG. 1-5). The IFN-γ-inducing activity of all oligonucleotides at 300 nM exceeded the activity of Mod2 (Lanes 2 to 6 in FIG. 1-6).

From the above results, it was demonstrated that when the base number (M) of poly-G sequences at the 5' terminus is 6 to 10, preferably 6 to 8, even though the oligonucleotide had no poly-G sequence at the 3' terminus, that led to the more enhanced IFN-inducing activity compared with the activity of the conventional D-type CpG sequence having the same PXCGYQ as in the aforementioned formula.

Example 2

Comparison of Base Numbers of 3' Terminal Poly-G Sequences Essential for the Inflammatory Cytokine-Inducing Activity in Murine J774 Cells Among Immunostimulatory Oligonucleotides Concerning the immunostimulatory oligonucleotides obtained by inserting 6 bases of a poly-G sequence at the 5' terminus, in vitro an induction evaluation test was performed to identify the presence or absence of induction of the IL-12 p40 production in murine J774 cells described above. That is, J774 cells were stimulated with each oligonucleotide for 48 hours, and the amount of the inflammatory cytokine IL-12 (IL-20 p40) produced in the culture supernatant was evaluated. As a result, in the production of IL-12 p40 by Mod50 (Lane 2), Mod49 (SEQ ID NO:13, Lane 3), Mod48 (SEQ ID NO:12, Lane 4), Mod33 (SEQ ID NO:5, Lane 5), Mod40 (lane 6) or Mod41 (Lane 7) at a final concentration of 300 nM of each sequences, the oligonucleotides having 4 or more bases of poly-G sequences at the 3' terminus (M=6/N=4 to 6, lanes 2 to 4) induced the IL-12 production, but no activity was observed in the oligonucleotides having 3 or less bases of poly-G sequences (M=6/N=0 to 3; Lane 5 to 7) (FIG. 2).

In light of the foregoing, it was demonstrated that the oligonucleotides having 3 or less bases of poly-G sequences at the 3' terminus reduced or lost the inflammatory cytokine-inducing activity even if the 6 bases of a poly-G sequence was inserted at the 5' terminus.

Example 3

Comparison of IFN Production-Inducing Effects in Human PBMC Between the Immunostimulatory Oligonucleotides of the Present Invention Containing a Sequence of CGATCG (SEQ ID NO:59), ATCGAT (SEQ ID NO:60) or GACGTC (SEQ ID NO:61) as Palindrome Motif, and D-Type CpG Oligonucleotide The oligonucleotides (G6-PXCGYQ-G3, M=6/N=3) including the immunostimulatory oligonucleotides of the present invention inserting poly-G sequences composed of 6 bases at the 5' terminus and 3 bases at the 3' terminus into 6 types of the palindrome motifs where P was T (thymine), Q was A (adenine) and XCGY was composed of 10 bases in the formula: 5'-$(G)_M$PXCGYQ$(G)_N$-3' (SEQ ID NO: 118), and the D-type CpG sequence inserting poly-G sequences composed of 2 bases at the 5' terminus and 6 bases at the 3' terminus (D-type CpG: G2-PXCGYQ-G6, M=2/N=6) were synthesized. In addition, their IFN-inducing activities were evaluated in human PBMC. The palindrome motif in each oligonucleotide is shown in Sequence Listing, FIGS. 3-1, 3-2 and 3-3, and is CCCGATCGGG of Lane 1 in Mod29 (SEQ ID NO:21) and Mod43 (SEQ ID NO:22), TCCGATCGGA of Lane 2 in Mod37 (SEQ ID NO:23) and Mod44 (SEQ ID NO:24), GGCGATCGCC of Lane 3 in Mod38 (SEQ ID NO:25) and Mod45 (SEQ ID NO:26), GACGATCGTC of Lane 4 in Mod39 (SEQ ID NO:27) and Mod46 (SEQ ID NO:28), or GCATCGATGC of Lane 5 in D19 (SEQ ID NO:29) and Mod47 (SEQ ID NO:30). The IFN-inducing activity in human PBMC using the above oligonucleotides was evaluated in the same procedure and conditions as in Example 1.

As a result of measuring the activity of the D-type CpG sequence and the immunostimulatory oligonucleotides of the present invention at a concentration of 100 nM, the IFN-α-inducing activity was enhanced in all palindrome motifs evaluated in the immunostimulatory oligonucleotides (FIG. 3-1, G6-PXCGYQ-G3) of the present invention compared with the D-type CpG sequences (G2-PXCGYQ-G6), and was augmented to 1.4 to 74.5 times more than the ability of D-type CpG. In the IFN-γ-inducing activity at 100 nM of the above oligonucleotide, the similar tendency to IFN-α was observed (FIG. 3-2).

The IFN-α-inducing activities of two immunostimulatory oligonucleotides, where P in the aforementioned formula was A (adenine) and Q was C (cytosine) or T (thymine) and 8 bases of a palindrome motif CGACGTCG SEQ ID NO:74) was contained, and the IFN-α-inducing activity of the D-type CpG were evaluated in the human PBMC. As a result, the activities of Mod71 (SEQ ID NO:40, M=7/N=2) and Mod73 (SEQ ID NO:42, M=6/N=2) which were the immunostimulatory oligonucleotides of the present invention was more remarkably augmented at 300 nM than the activity of Mod70 (SEQ ID NO:39, M=3/N=6) and Mod72 (SEQ ID NO:41, M=2/N=6) which respectively correspond D-type CpG sequences (FIG. 3-3).

These results indicate that the inserted-type of the poly-G sequences in the novel immunostimulatory oligonucleotides of the present invention augments the IFN-inducing activity without depending on the particular palindrome structure.

Example 4

IFN-α Production-Inducing Effect in Human PBMC by the Immunostimulatory Oligonucleotides of the Present Invention Having CGATCG (SEQ ID NO:59) as Palindrome Motif Optimal sequences of immunostimulatory oligonucleotides of the present invention were examined. P and Q in the immunostimulatory oligonucleotide of the present invention, where M=7 and N=2, and XCGY was GACGATCGTC SEQ ID NO:76), were examined. The oligonucleotide (Mod83, SEQ ID NO:51) where P was A (adenine) and Q was T (thymine), the oligonucleotide (Mod84, SEQ ID NO:48) where P was T and Q was A, the oligonucleotide (Mod85, SEQ ID NO:50) where both P and Q were A and the oligonucleotide (Mod87, SEQ ID NO:52) where P was C and Q was A were synthesized. The IFN-α-inducing activity of Mod46 having particularly strong IFN-inducing activity among the immunostimulatory oligonucleotides of the present invention found in Example 3, and the IFN-α-inducing activities of these oligonucleotides were compared and evaluated in human PBMC. The IFN-inducing activity in human PBMC was evaluated in the same procedure and conditions as in Example 1, except that the oligonucleotides were replaced and only IFN-α was measured.

Figures 1, 2, 3, 4:
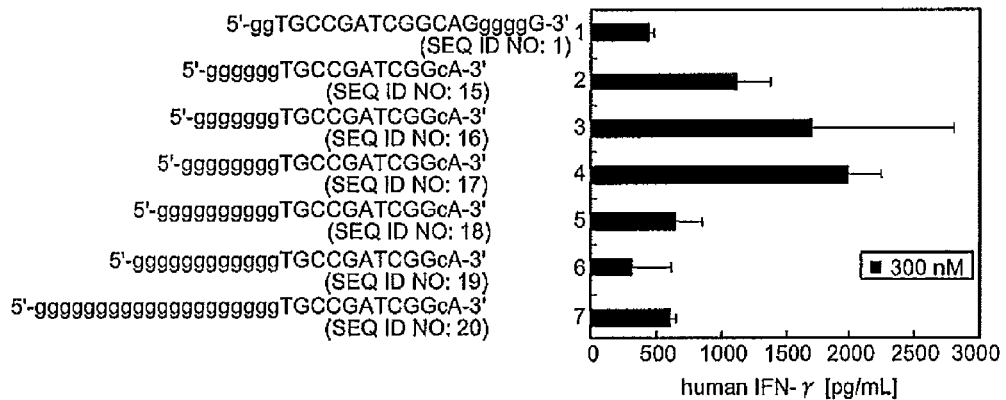

As a result, at 100 nM of the oligonucleotides, Mod83, Mod84, Mod85 and Mod87 exhibited IFN-α-inducing activities equivalent to the activity of Mod46 (FIG. 4). This result indicates that P and Q in the immunostimulatory oligonucleotide of the present invention may be any one other than G, i.e., any of A, T and C; even if they are not complementary nucleotides each other, the oligonucleotide has the strong IFN-α-inducing activity.

Example 5

Comparison of IFN-Inducing Activities in Human PBMC Between the Immunostimulatory Oligonucleotides of the Present Invention, and the Oligonucleotides of 09-GACGATCGTC-G1 (SEQ ID NO:36) and G7-GACGATCGTC-G3 (SEQ ID NO:98)

The IFN-inducing activities in human PBMC by immunostimulatory oligonucleotides of the present invention, and those by the oligonucleotides of G9-GACGATCGTC-G1 (SEQ ID NO:36) and G7-GACGATCGTC-G3 (SEQ ID NO:98) known as the sequences having strong IFN-α-inducing activity in JP 2005-237328-A were compared.

Mod92 (SEQ ID NO:97) and Mod93 (SEQ ID NO:95) which were the immunostimulatory oligonucleotides of the present invention, which had the most approximate sequences to 09-GACGATCGTC-G1 (SEQ ID NO:36) and 07-GACGATCGTC-G3 (SEP ID NO:98) and were synthesized without modifying with phosphorothioate, and then their IFN-α-inducing activities in human PBMC were compared (Tables 3 and 4). The IFN-inducing activity in human PBMC was evaluated in the same procedure and conditions as in Example 1, except that the oligonucleotides were replaced.

As a result, Mod92 and Mod 93 exhibited higher IFN-α-inducing activity than those of G7-GACGATCGTC-G3 (SEQ ID NO:98) and G9-GACGATCGTC-G1 (SEQ ID NO:36).

Table 3

TABLE 3

IFN-α PRODUCTION AMOUNT IN HUMAN PBMC

| CpG | Sequence 5'-3' | IFN-α [pg/mL] |
|---|---|---|
| Mod92 | GGGGGGTGACGATCGTCGGG (SEQ ID NO: 97) | 3263.3 ± 424.5 |
| G7-GACGATCGTC-G3 (SEQ ID NO: 98) | GGGGGGGGACGATCGTCGGG (SEQ ID NO: 98) | 2515.1 ± 307.0 |

The amounts of IFN represented in Table 3 are the values of the produced IFN when the concentration (final concentration) of the immunostimulatory oligonucleotides was 100 nM. No modification with phosphorothioate was given to all of the above oligonucleotides.

Table 4

TABLE 4

IFN-α PRODUCTION AMOUNT IN HUMAN PBMC

| CpG | Sequence 5'-3' | IFN-α [pg/mL] |
|---|---|---|
| Mod93 | GGGGGGGGCGACGATCGTCG (SEQ ID NO: 95) | 2442.5 ± 171.4 |
| G9-GACGATCGTC-G1 (SEQ ID NO: 36) | GGGGGGGGGGACGATCGTCG (SEQ ID NO: 36) | 684.0 ± 277.9 |

The amounts of IFN represented in Table 4 are the values of the produced IFN when the concentration (final concentration) of the immunostimulatory oligonucleotides was 100 nM. No modification with phosphorothioate was given to all of the above oligonucleotides.

In light of the foregoing, it was demonstrated that the immunostimulatory oligonucleotides of the present invention had strong IFN-α-inducing activity, even if they had not been modified with phosphorothioate. It was also shown that it was important that P and Q in the general formula were the bases other than G. Therefore, it was shown that the IFN-α-inducing activity was further enhanced by inserting at least one base nucleotide between the palindrome sequence such as GACGATCG (SEQ ID NO:76) exhibiting the excellent IFN-α-inducing activity and the poly-G sequence.

Example 6

Comparison of IL-12-Inducing Activities in Human PBMC Between the Immunostimulatory Oligonucleotides of the Present Invention, and the Oligonucleotides of G9-GACGATCGTC-G1 (SEQ ID NO:36) and G7-GACGATCGTC-G3 (SEQ ID NO:98)

The IL-12-inducing activity of immunostimulatory oligonucleotide of the present invention which was Mod93 used in Example 5, and the IL-12-inducing activity of G9-GACGATCGTC-G1 SEQ ID NO:36) or G7-GACGATCGTC-G3 SEQ ID NO:98) disclosed in JP 2005-237328-A were compared in human PBMC. The levels of IL-12 were measured in accordance with the specific method of the aforementioned test to evaluate the IL-12-inducing activity in vitro.

As a result, Mod93 of the present invention did not induce the production of IL-12 at all; on the contrary, it tended to suppress the IL-12 production compared with the control which had not been stimulated (Table 5). Meanwhile, G9-GACGATCGTC-G1 (SEQ ID NO:36) exhibited an weak increase in the IL-12 production. Therefore, it was shown that the inflammatory cytokine-inducing activity in human was also low by the immunostimulatory oligonucleotide of the present invention.

Table 5

TABLE 5

IL-12 PRODUCTION IN HUMAN PBMC

| CpG | Sequence 5'-3' | IL-12 [pg/mL] |
|---|---|---|
| no CpG-ODN | | 4.878 ± 0.610 |
| Mod93 | GGGGGGGGCGACGATCGTCG (SEQ ID NO: 95) | 1.423 ± 0.932 |
| G9-GACGATCGTC-G1 (SEQ ID NO: 36) | GGGGGGGGGGACGATCGTCG (SEQ ID NO: 36) | 5.895 ± 0.704 |

The amounts of IL-12 represented in Table 5 are the values of produced IL-12 when no stimulation was added (no CpG-ODN) or the concentration (final concentration) of the immunostimulatory oligonucleotides was 300 nM. No modification with phosphorothioate was given to all of the above oligonucleotides.

In the stimulation with the immunostimulatory oligonucleotide alone, because no remarkable production of IL-2 from human peripheral blood cells was observed, by stimulating with an immunostimulatory oligonucleotide together with lipopolysaccharide (LPS) being an endotoxin which was a potent inducer of the inflammatory response, the effect on the IL-12 production was evaluated. That is, the PBMC isolated according to the aforementioned method were prepared at $2.0 \times 10^6$ cells per in L in RPMI 1640 medium containing 10% FCS, seeded at $2.0 \times 10^5$ cells per well in a round bottomed 96-well microplate, and cultured in coexistence of LPS and the immunostimulatory oligonucleotide for 24 hours. Then, the culture supernatant was collected, and the production of IL-12 was quantified by ELISA. As the immunostimulatory oligonucleotides, Mod92, Mod93, G9-GACGATCGTC-G1 (SEQ ID NO:36) and G7-GACGATCGTC-G3 (SEQ ID NO:98) were used. As a result, any of the immunostimulatory oligonucleotides did not augment the IL-12 production induced by the stimulation with LPS (50 ng/mL). Rather, the suppressive effect on its production was observed, and Mod93 which was the immunostimulatory oligonucleotide of the present invention exhibited the strongest inhibitory activity (Table 6).
Table 6

TABLE 6

IL-12 PRODUCTION IN HUMAN PBMC BY CpG-ODN IN THE PRESENCE OF LPS

| CpG | Sequence 5'-3' | IL-12 [pg/mL] |
|---|---|---|
| no CpG-ODN | | 620.2 ± 49.9 |
| Mod92 | GGGGGGTGACGATCGTCGGG (SEQ ID NO: 97) | 535.6 ± 44.9 |
| G7-GACGATCGTC-G3 (SEQ ID NO: 98) | GGGGGGGGACGATCGTCGGG (SEQ ID NO: 98) | 569.0 ± 14.3 |
| Mod93 | GGGGGGGGCGACGATCGTCG (SEQ ID NO: 95) | 488.1 ± 17.3 |
| G9-GACGATCGTC-G1 (SEQ ID NO: 36) | GGGGGGGGGGACGATCGTCG (SEQ ID NO: 36) | 584.8 ± 46.6 |

The amounts of IL-12 represented in Table 6 are the values of produced IL-12 when no stimulation (no CpG-ODN) was added or the concentration (final concentration) of the immunostimulatory oligonucleotides was 100 nM in the presence of LPS. No modification with phosphorothioate was given to all of the above oligonucleotides.

From the above results, it was demonstrated that the immunostimulatory oligonucleotides of the present invention exhibited lower inflammatory cytokine-inducing activity than the oligonucleotides having the publicly known sequences and had an anti-inflammatory action.

Example 7

Comparison of IFN-Inducing Activities in Human PBMC Between the Immunostimulatory Oligonucleotides of the Present Invention, and the Oligonucleotides of M26, M27, M26-GS, M27-GS, I1, 2006, 2395, 1018, C274, G9-GACGATCGTC-G1 (SEQ ID NO:36) and D19

Figures 1, 2, 3, 4, 5:
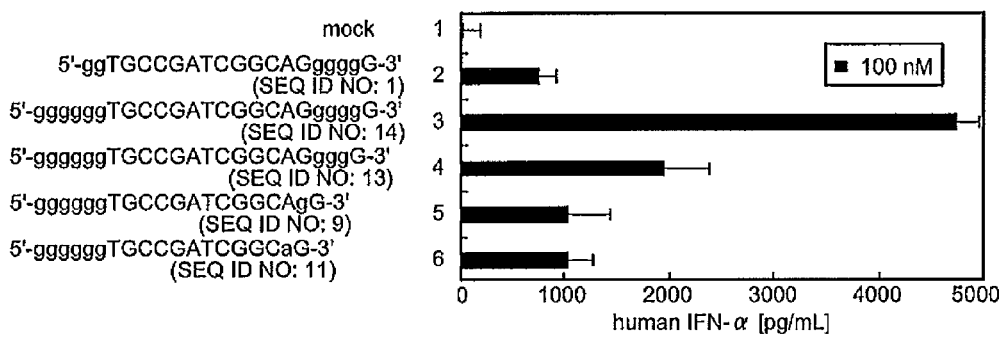

The IFN-α-inducing activities of the oligonucleotide sequences of M26 (SEQ ID NO:37) and M27 (SEQ ID NO:38) disclosed in KR 2001-0063153 (Korea Patent Office), the IFN-α-inducing activities of M26-CS and M27-CS obtained by giving the phosphorothioate modification to the internucleotide bonds of the poly-G sequence thereof, and IFN-α-inducing activities of the immunostimulatory oligonucleotides Mod55 and Mod 46 of the present invention found in Examples 1 and 3, were compared and evaluated. The IFN-inducing activity in human PBMC in Example 5 was evaluated in the same procedure and conditions as in Example 1, except that the oligonucleotides were replaced and only IFN-α was measured. As a result, at 100 nM of the oligonucleotides, the immunostimulatory oligonucleotides of the present invention exhibited much higher IFN-α-inducing activity than the other oligonucleotides (FIG. 5-1).

Subsequently, the IFN-α-inducing activities of the oligonucleotide sequence of G9-GACGATCGTC-G1 (SEQ ID NO:36) known as the representative sequence having a strong IFN-α-inducing activity in JP 2005-237328-A, and the IFN-α-inducing activities of the immunostimulatory oligonucleotides of the present invention which were Mod53, Mod54, Mod55, Mod61, Mod62, Mod45, Mod46, Mod71 and Mod73 found in Examples 1 and 3, were compared and evaluated. As a result, the immunostimulatory oligonucleotides of the present invention exhibited higher IFN-α-inducing activity at a concentration of 1 µM (FIG. 5-2).

The IFN-α-inducing activities of the oligonucleotide sequence I1 shown in JP Hei-10-506265, the IFN-α-inducing activity of the immunostimulatory oligonucleotide of the present invention which was Mod46 found in Example 3, and the IFN-α-inducing activities of Mod 39 and Mod 33 which were the D-type CpG having the same palindrome sequence as in Mod46, were compared and evaluated. As a result, the other oligonucleotides scarcely exhibited any activity whereas the immunostimulatory oligonucleotide of the present invention exhibited a remarkably high IFN-α-inducing activity at a concentration of 30 nM (FIG. 5-3).

The IFN-α-inducing activities in human PBMC by the oligonucleotide sequence (D19) shown in International Publication No. 00/61151 Pamphlet, IFN-α-inducing activities of the oligonucleotide sequences (2006) shown in JP 2001-503267 and International Publication No. 1998/018810 Pamphlet, the IFN-α-inducing activity of the oligonucleotide sequence (2395) shown in International Publication No. 03/015711 Pamphlet, of the oligonucleotide sequences (1018) shown in JP 2002-517156 and JP-2002-500159, and of the oligonucleotide sequence (C274) shown in International Publication No. 04/058179 Pamphlet, and the IFN-α-inducing activity of the immunostimulatory oligonucleotide of the present invention which is Mod46 (SEQ ID NO:28), were compared. As a result, at 100 nM of oligonucleotides, it was demonstrated that the immunostimulatory oligonucleotide of the present invention had the strongest IFN-α-inducing activity (FIG. 5-4).

In light of the foregoing, it was revealed that the immunostimulatory oligonucleotide of the present invention exhibited a higher IFN-α-inducing activity than those of immunostimulatory oligonucleotides having the publicly known CpG sequences.

Example 8

Comparison of IFN-α-Inducing Activities in Human PBMC Between the Immunostimulatory Oligonucleotides of the Present Invention: Mod46, Mod83, Mod85 and Mod87, and Publicly Known CpG Oligonucleotides: G10, G3-6, G9-GACGATCGTC-G1 (SEQ ID NO:36), G1-GACGATCGTC-G9 (SEQ ID NO:55) and 2332, which have Poly-G Sequence and Palindrome Sequence GACGATCGTC (SEQ ID NO:76)

Figures 1, 2, 3, 4, 5, 6:
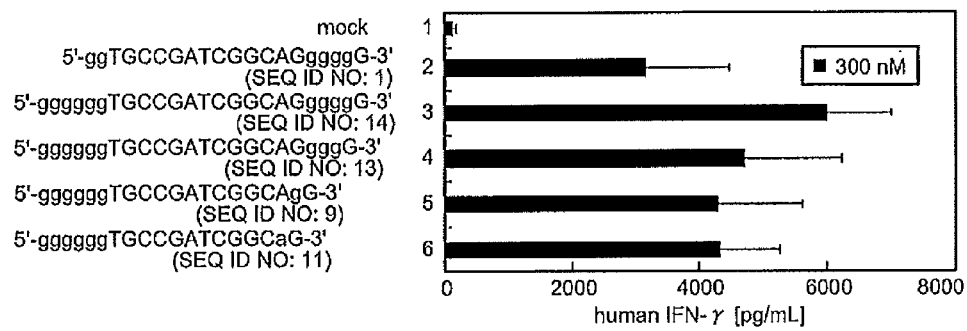
Figure 2:
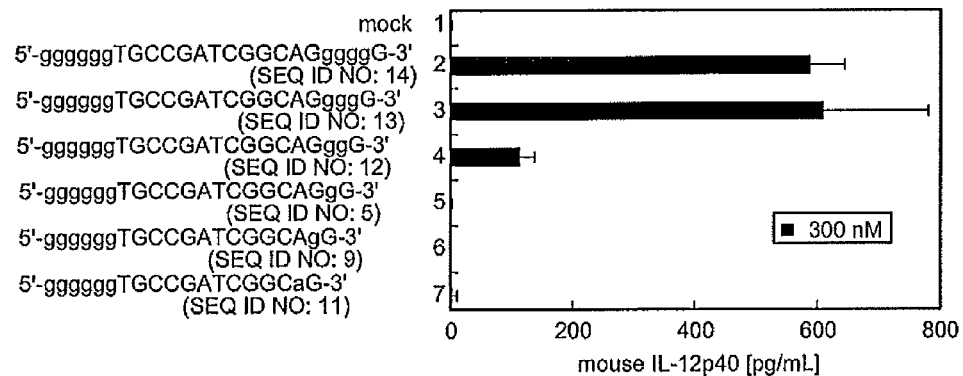
Figures 1, 3:
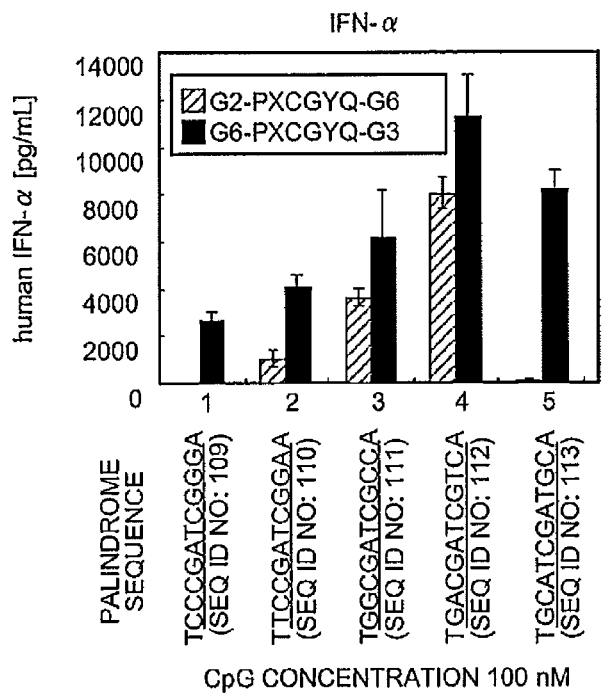
Figures 2, 3:
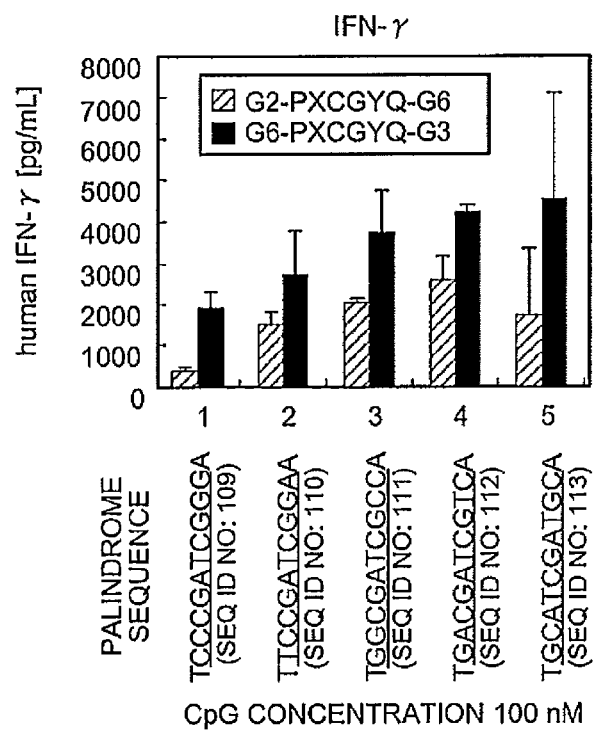
Figures 1, 5:
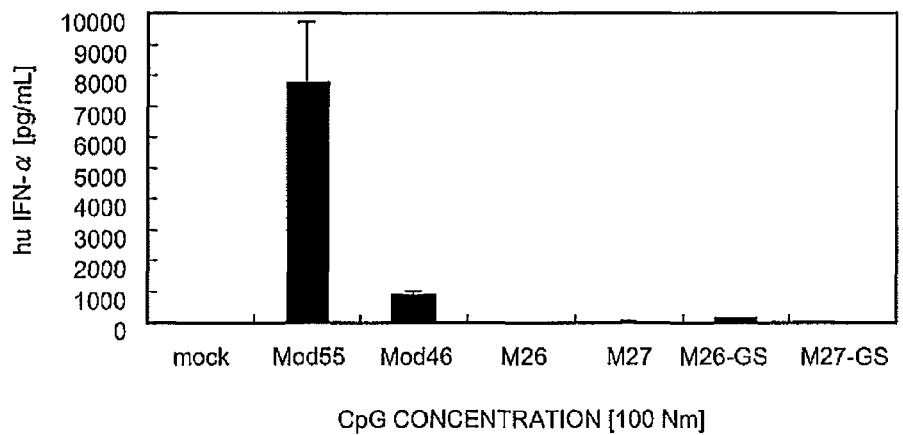
Figures 2, 5:
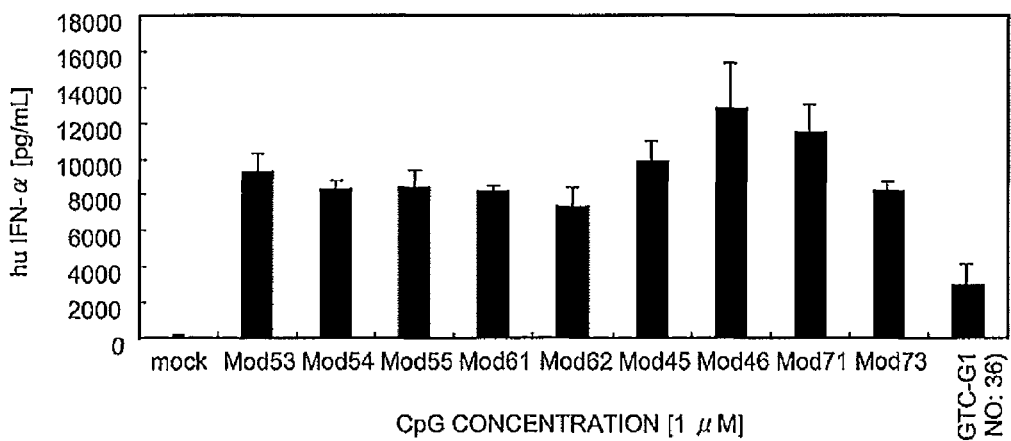
Figures 3, 5:
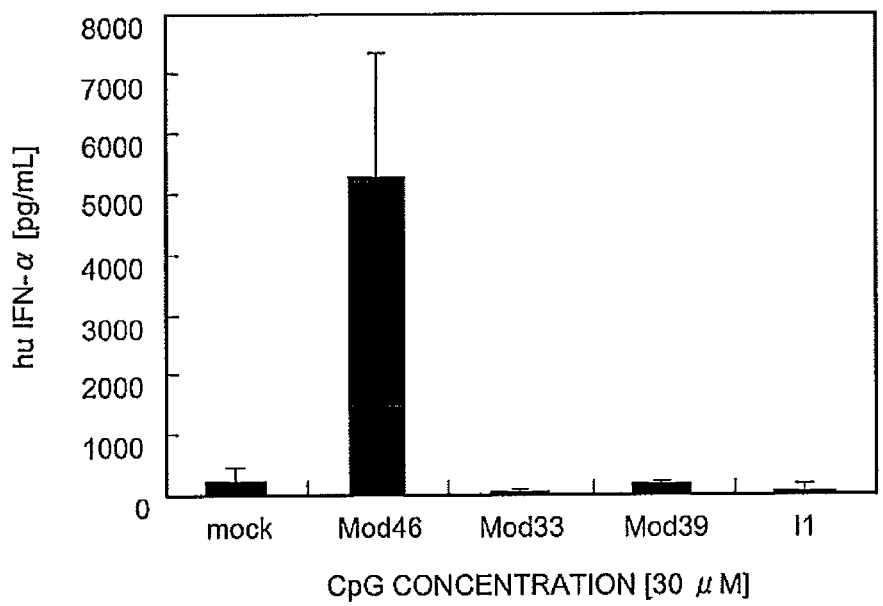
Figures 4, 5:
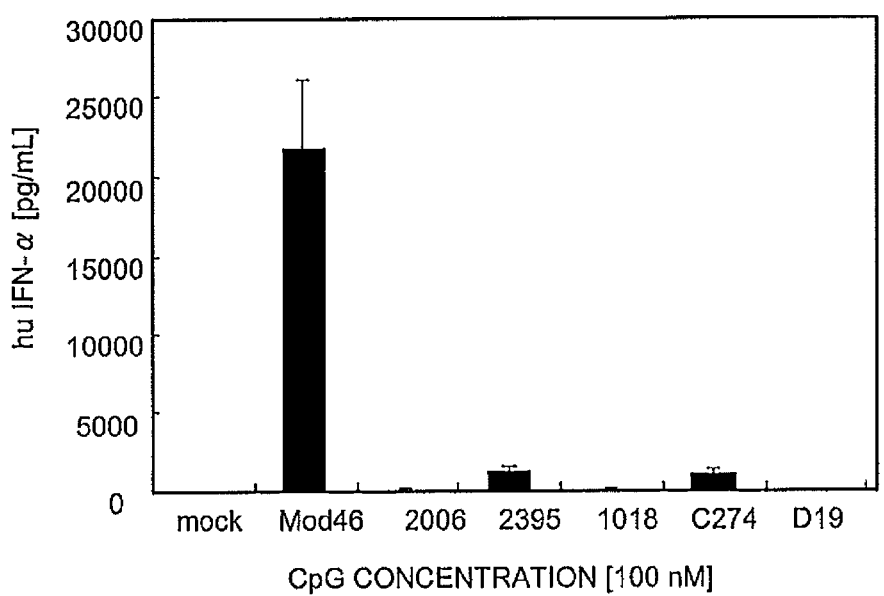
Figure 6:
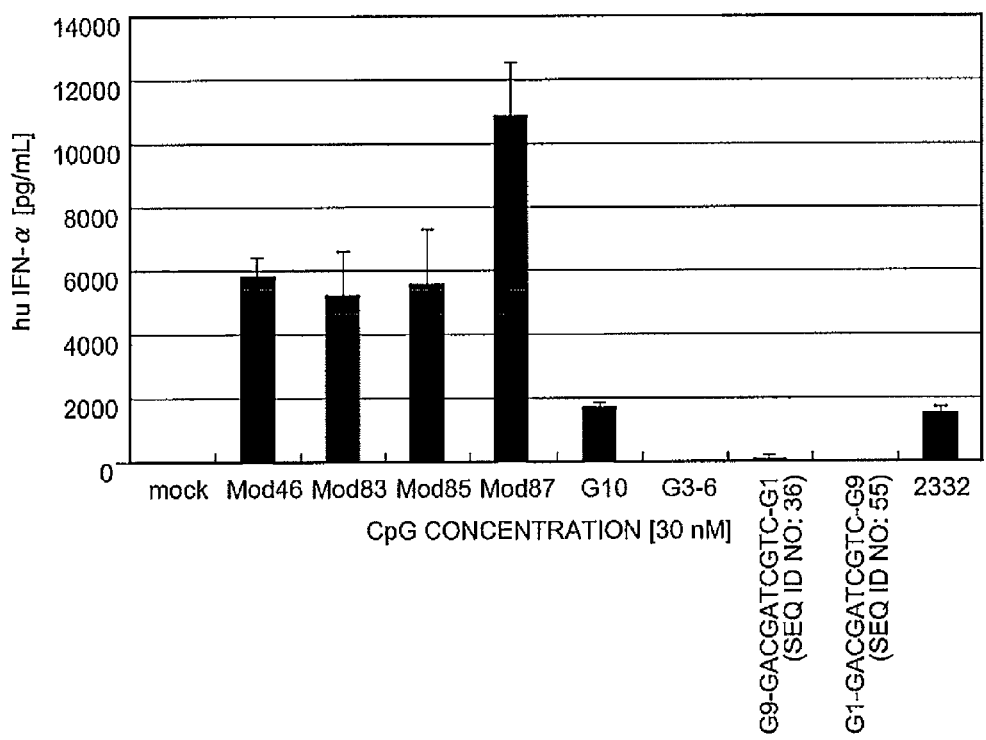

The publicly known CpG oligonucleotides where the poly-G sequence has been inserted outside the palindrome sequence GACGATCGTC (SEQ ID NO:76) may include the oligonucleotide sequences of G9-GACGATCGTC-G1 (SEQ ID NO:36) and G1-GACGATCGTC-G9 (SEQ ID NO:55) disclosed in JP 2005-237328-A, G10 (SEQ ID NO:56) and the sequence of G3-6 (SEQ ID NO:57) disclosed in International Publication No. 2005/014110 Pamphlet, and the sequence of 2332 (SEQ ID N0:58) disclosed in JP 2003-510290. Then, the IFN-α-inducing activities of the immunostimulatory oligonucleotides of the present invention being Mod46, Mod83, Mod85 and Mod87, and those of the above publicly known CpG oligonucleotides were compared and evaluated. The IFN-inducing activity in human PBMC was evaluated in the same procedure and conditions as in Example 1, except that the oligonucleotides were replaced and only IFN-α was measured. As a result, at 30 nM of the oligonucleotides, the immunostimulatory oligonucleotides of the present invention exhibited higher IFN-α-inducing activity than the other oligonucleotides (FIG. 6).

Example 9

Comparison of Cytokine Production-Inducing Activities in Murine Splenic Cells Among the Immunostimulatory Oligonucleotides: Mod2, Mod33, Mod39 and Mod46

Using murine splenic cells derived from C57BL/6 mice, the cytokine production-inducing activities were compared and evaluated among the immunostimulatory oligonucleotides of the present invention, Mod46 and Mod33 found in Examples 1 and 3, and Mod39 and Mod2 which were the D-type CpG oligonucleotides.

Figures 1, 7:
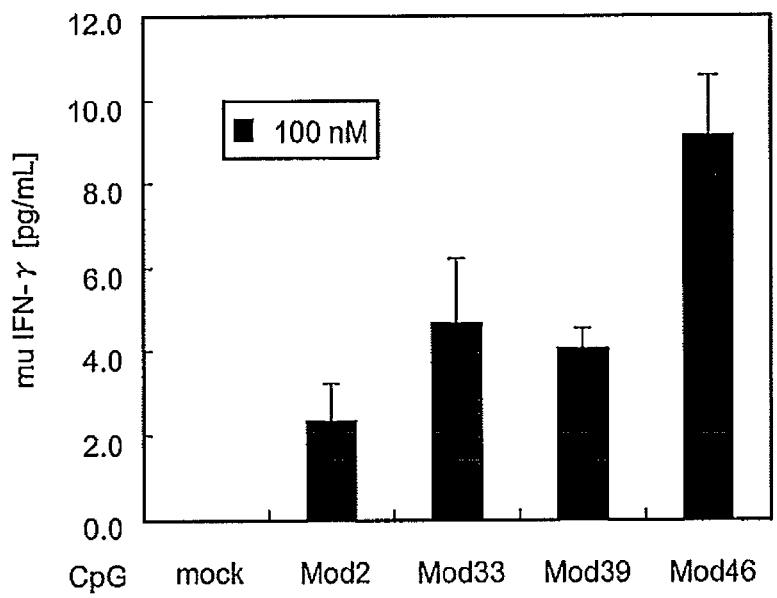
Figures 2, 7:
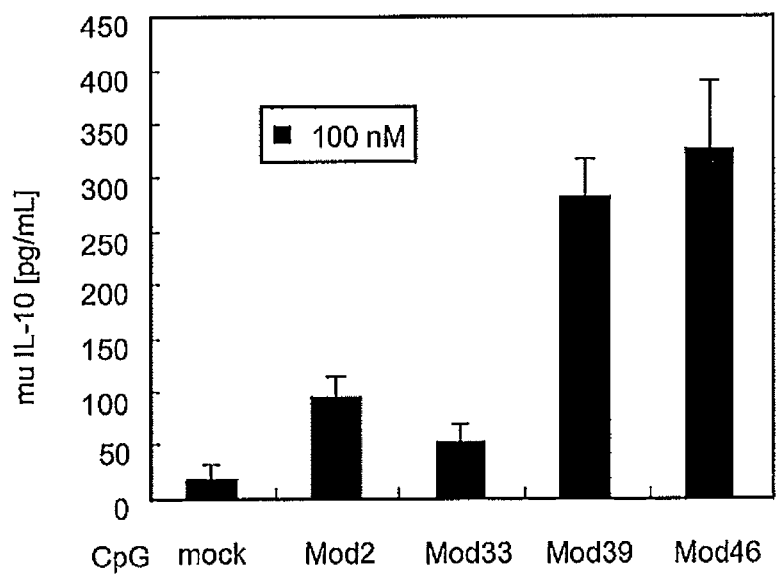

The IFN-γ-inducing activity and the IL-10-inducing activity of the D-type CpG and the immunostimulatory oligonucleotides of the present invention at 100 nM were measured. The measurement was performed according to the procedure and conditions presented as the specific method of identifying the presence or absence of the induction of IFN-γ and IL-10 production in the murine splenic cells described above. As a result, the immunostimulatory oligonucleotide Mod46 of the present invention exhibited more augmented IFN-γ-inducing activity than Mod39 which was the D-type CpG having the same palindrome sequence as Mod46, and the activity of Mod46 was much higher than that of Mod33 (FIG. 7-1). Meanwhile, the IL-10-inducing activities of Mod33 and Mod46 were almost equivalent to those of Mod2 and Mod39, respectively (FIG. 7-2). It was suggested that the induction of the immunosuppressive cytokine IL-10 production by the immunostimulatory oligonucleotide might be different from the induction of the inflammatory cytokine in mechanisms.

The above results indicate that the novel immunostimulatory oligonucleotide of the present invention augments the IFN-inducing activity without depending on the palindrome motif with maintaining the IL-10-inducing activity. Although the immunostimulatory activity has species specificity depending on the CpG sequence, it was demonstrated that the immunostimulatory oligonucleotides of the present invention augmented the IFN-inducing activity without being affected by species difference, and it was suggested that those of the present invention have a universal structure to augment the activity.

Example 10

Figures 1, 8:
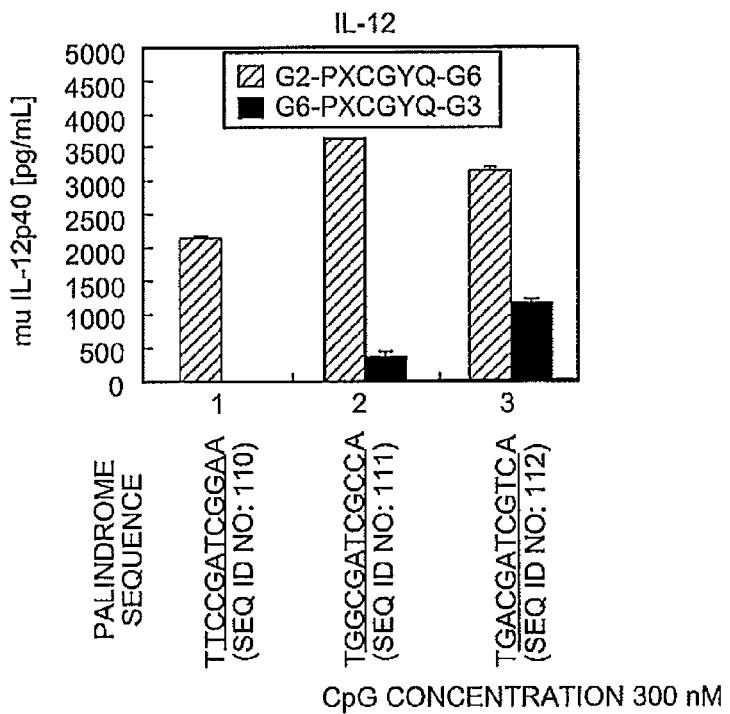
Figures 2, 8:
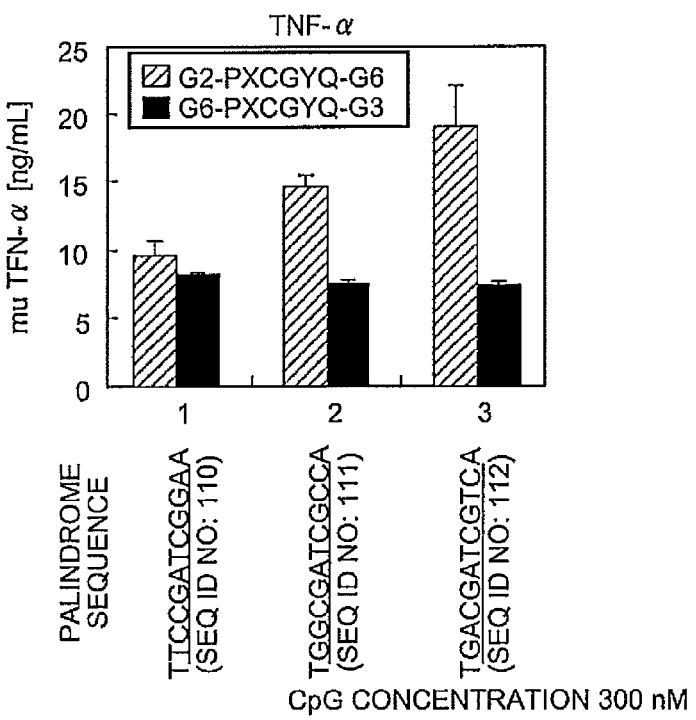

Reduction of Inflammatory Cytokine-Inducing Activity by the Novel Immunostimulatory Oligonucleotides of the Present Invention in J774 Cell Line The inflammatory cytokine production-inducing activity of the immunostimulatory oligonucleotides of the present invention found in Example 3 was compared with the activity of the D-type CpG oligonucleotides having the same palindrome, and the results were evaluated. The palindrome motif in each oligonucleotide is shown in Sequence Listing or in FIGS. 8-1 and 8-2, and TCCGATCGGA (SEQ ID NO:88) of Mod37 and Mod44 is in Lane 1, GGCGATCGCC (SEQ ID NO:77) of Mod38 and Mod45 is in Lane 2, GACGATCGTC (SEQ ID NO:76) of Mod39 and Mod46 is in Lane 3. The evaluation was performed according to the procedure and conditions presented as a test to evaluate the IL-12- or TNF-α-inducing activity in J774 cells described above. As a result, at 300 nM remarkably, Mod44, Mod45 and Mod46 which were the immunostimulatory oligonucleotides of the present invention suppressed both IL-12-inducing activity (FIG. 8-1) and TNF-α-inducing activity (FIG. 8-2) compared with the D-type CpG having the same palindrome sequence correspondingly: Mod37, Mod38 and Mod39.

As the above results, the novel immunostimulatory oligonucleotides having an inserted-type of the poly-G sequence found in the present invention exhibited further reduced inflammatory cytokine-inducing activity compared with the conventional D-type CpG having the same palindrome motif.

Example 11

Comparison of TNF-α-Inducing Activities in J774 Cell Line between the Immunostimulatory Oligonucleotides of the Present Invention and Oligonucleotides of 2006, 2395, 1018 and C274

Figure 9:
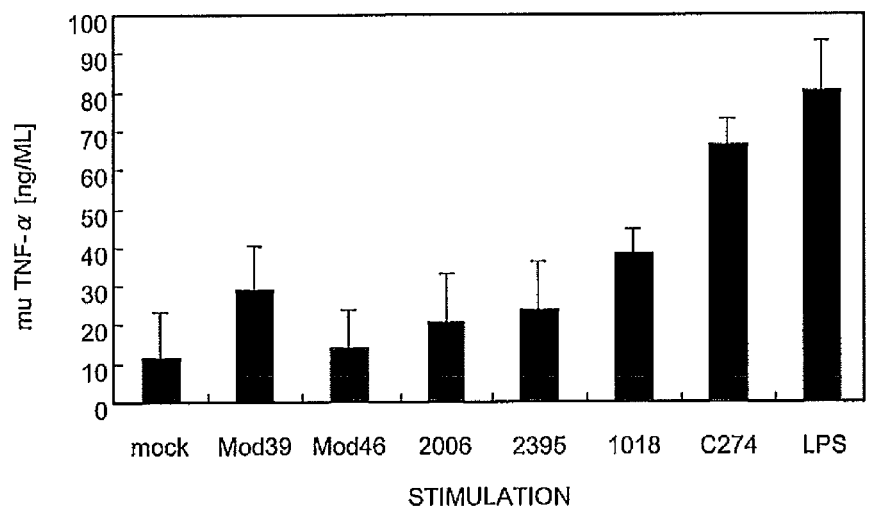
FIG. 9 shows results of stimulating murine J774 cells with the immunostimulatory oligonucleotides of the present invention or D-type CpG having the same palindrome motif or the publicly known immunostimulatory oligonucleotides and measuring amounts of produced TNF-α in culture supernatants in Example 11.

TNF-α-inducing activities of the immunostimulatory oligonucleotides of the present invention of Mod46 found in Example 8 and the TNF-α-inducing activities of the publicly known CpG oligonucleotides were evaluated. J774 cells were stimulated with each immunostimulatory oligonucleotide (final concentration of 300 nM) or lipopolysaccharide (LPS: final concentration of 100 ng/mL) as a positive control for 8 hours, and then the amount of TNF-α produced in the culture supernatant was measured. The other procedure and conditions were the same as in Example 10. As a result, Mod46 exhibited considerably attenuated TNF-α-inducing activity compared with the oligonucleotides 2006 (SEQ ID NO:31), 2395 (SEQ ID NO:32), 1018 (SEQ ID NO:33) and C274 (SEQ ID NO:34) shown in Example 4, and Mod39 and LPS (FIG. 9). From this and also considering the results shown in Examples 2 and 6, it was shown that the immunostimulatory oligonucleotides of the present invention having 3 or less bases of poly-G sequence at the 3' terminus attenuated the inflammatory cytokine-inducing activity.

Example 12

Comparison of IgE Production-Suppressing Activities in Human PBMC between the Immunostimulatory Oligonucleotides Mod87 of the Present Invention, and the Oligonucleotides of Mod39 and 1018

Figure 10:
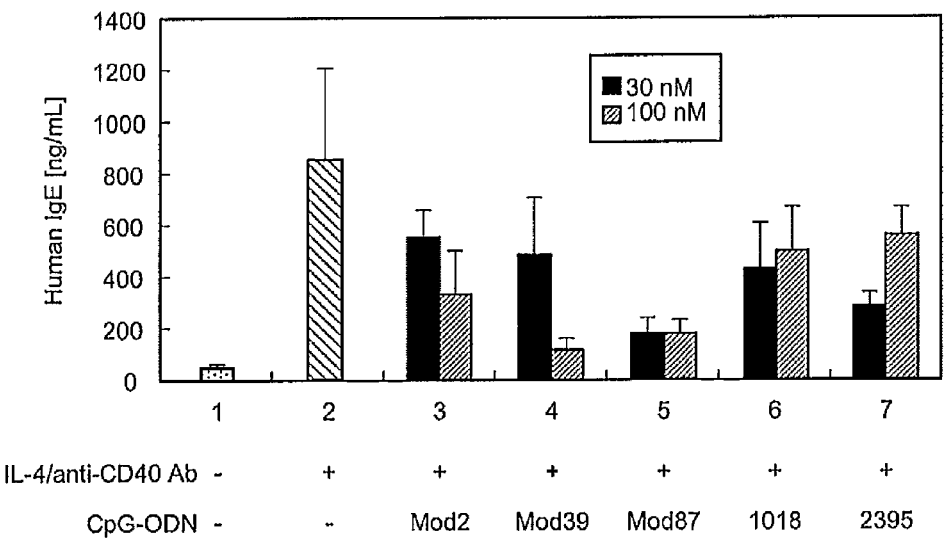
FIG. 10 shows results of stimulating human PBMC with the immunostimulatory oligonucleotides of the present invention or D-type CpG having the same palindrome motif or the publicly known immunostimulatory oligonucleotides together with anti-CD40 antibody and IL-4 and measuring amounts of produced IgE in culture supernatants in Example 12.

The IgE production-suppressing activity of the immunostimulatory oligonucleotide of the present invention which was Mod87 found in Example 8 and the IgE production-suppressing activities of publicly known CpG oligonucleotides, were evaluated according to the procedure and conditions presented as the specific method of a test to evaluate the activity of suppressing the IgE production in vitro described above, based on the amount of IgE produced in the culture supernatant obtained by the stimulation for 14 days. That is, the PBMC were prepared at $4.0 \times 10^6$ cells per mL in RPMI medium containing 10% FCS, seeded at $4.0 \times 10^5$ cells per well in a flat bottomed 96-well microplate, and stimulated with the immunostimulatory oligonucleotide at a final concentration of 30 or 100 nM together with 20 ng/mL of human IL-4 and 0.2 µg/mL of anti-CD40 antibody for 14 days. Then, the amount of IgE produced in the culture supernatant was measured by ELISA (FIG. 10).

As a result, concerning the IgE production induced by IL-4 and anti-CD40 antibody, the immunostimulatory oligonucleotide Mod87 of the present invention (Lane 5 in FIG. 10) more strongly suppressed an IgE production compared with Mod2 (Lane 3 in FIG. 10) and Mod39 (Lane 4) disclosed in International Publication No. 2006/035939 Pamphlet, 1018 (Lane 6) disclosed in JP 2002-500159 and 2395 (Lane 7) disclosed in International Publication No. 03/015711 pamphlet.

In light of the foregoing, it was shown that the immunostimulatory oligonucleotide of the present invention had higher activity of suppressing the IgE production than the immunostimulatory oligonucleotides having a publicly known CpG sequence and might be effective for a therapy for human allergy.

Example 13

Suppressive Effect of the Immunostimulatory Oligonucleotide of the Present Invention on IgE Production in Animals An anti-allergic therapeutic effect of the immunostimulatory oligonucleotide Mod87 of the present invention showing the remarkable activity of suppressing the IgE production in Example 12, was evaluated by measuring the amount of serum IgE produced when a Th2 response specific for an allergen was elicited in mice. A cedar pollen antigen of Cry j1 known as one of the allergens causing cedar pollens allergy was used as an allergen. Cry j1 was purified in accordance with the publicly known method (H. Yasueda et al., J. Allergy Clin. Immunol., 71, 77-86, 1983; M. Sakaguchi et al., 45, 309-312, 1990). In JP 2002-517156, a method of making the antigen proximate to a immunostimulatory oligonucleotide is disclosed as the means to enhance an anti-allergic therapeutic effect. Specifically, the method using a covalent bond or the method using a microcapsule such as liposome are available, and in International Publication No. 2006/035939 Pamphlet it has been reported that when a liposome complex enclosing Mod2 and Cry j1 was exposed to the allergen, the level of IgE induced in blood was suppressed. It was demonstrated that this suppressive effect on the IgE production was higher than the effect of the oligonucleotides having the publicly known CpG sequences. Then, anti-allergic therapeutic effects of Md87 and Mod2 were evaluated by the above test method using "adjoining technique" by a liposome.

A liposome complex enclosing Cry j1 and the immunostimulatory oligonucleotide was prepared as follows. As a negative control, a liposome complex enclosing Cry j1 but no immunostimulatory oligonucleotide was prepared. Cholesterol and dipalmitoyl phosphatidyl choline (DPPC) were mixed at a molar ratio of 1:1, and the mixture was dissolved in a solution of chloroform:methanol (=2:1) to form a lipid film in a pear-shaped flask. Subsequently, 3.75 mg/mL of Cry j1, or Cry j1 and 10 to 20 nM of the immunostimulatory oligonucleotide were added to the lipid film, and stirred at 40° C. to make liposomes. The amount of Mod87 was used in one condition (1×Mod87), and the amounts of Mod2 were used in two conditions (1×Mod2: equivalent to the amount of Mod87) and (3×Mod2: 3 times amount of Mod87). Particle sizes of these liposomes were granulated 5 times with applying the pressure at the range of 0.2 to 1 MPa to a filter of 1 µm using an extruder which was a particle size granulator. Subsequently, the liposomes were collected by centrifugation, and suspended in PBS (−). Free Cry j1 and free immunostimulatory oligonucleotides outside of the liposome were removed by repeating 3 times of suspension, centrifugation and supernatant removal. In an analysis of resulting liposomes, the amounts of cholesterol, Cry j1 and the immunostimulatory oligonucleotide were measured using commercially available kits, Cholesterol E Test Wako (Wako Pure Chemical Industries Ltd., 439-17501), Modified Lowry Protein Assay Reagent Kit (Pierce, 23240) and OliGreen ssDNA Quantitation Kit (Molecular Probes, O-11492), respectively. The amounts of 1×Mod87, 1×Mod2 and 3×Mod2 per 1 µg of Cry j1 in a liposome liquid were 4.751, 5.425 and 16.867 ng, respectively.

The abbreviations of the liposome complex shown in the following Examples are as follows. "Cry j1+1×Mod2/L" is the liposome complex in which Cry j1 and 1×Mod2 have been enclosed, "Cry j1+3×Mod2/L" is the liposome complex in which Cry j1 and 3×Mod2 have been enclosed, and "Cry j1+1×Mod87/L" is the liposome complex in which Cry j1 and 1×Mod87 have been enclosed. In "1×Mod", about 5 ng of the immunostimulatory oligonucleotide per 1 g of Cry j1 is contained. In "3×Mod", 3 times amount of 1×, i.e., about 15 ng of the immunostimulatory oligonucleotide per 1 µg of Cry j1 was contained. "Cry j1/L" means that Cry j1 alone has been enclosed in a liposome. "Cry j1" means that Cry j1 has been directly administered without being enclosed in a liposome.

Each subject substance being tested was administered to BALB/c mice aged 6 weeks (Charles River Japan Inc.) by intradermal inoculation (i.d.) at three times with one week interval, i.e., 0 W, 1 W and 3 W when the week of starting the administration was 0 W. As the subject substance, Cry j1, Cry j1/L, Cry j1+1×Mod2/L, Cry j1+3×Mod2/L or Cry j1+1×Mod87/L were prepared in PBS so that the Cry j1 protein amount was 1 µg/100 µL, and 100 µL per once was administered. The mixed solution of Cry j1 and alum was twice administered by intraperitoneal injection one week (3 W) and two week (4 W) after the final administration of the subject substance in order to elicit the Th2 response. At 6 W, fundus blood sample was collected. The blood was centrifuged and then the serum was frozen and stored at −20° C. The obtained serum was used as the sample for measuring the amount of total TqE in serum, which was the indicator of the Th2 response. After the final collection of the blood sample, spleen was removed from each individual and homogenized, and the splenic cells were prepared in accordance with the method described in the specific method herein to identify the presence or absence of the induction of the IFN-γ and IL-10 production (RPMI 1640 medium containing 10% fetal calf serum). A splenic cell suspension from each individual was seeded at $4 \times 10^5$ cells per well in a round bottomed 96-well multiplate, and cultured in the presence of Cry j1 (final concentration of 25 µg/mL) in a $CO_2$ incubator for 72 hours. Then, the culture supernatant was collected. The amounts of IL-5 (indicator of Th2 response) and IFN-γ (indicator of Th1 response) in the collected culture supernatant were measured by ELISA.

Figure 11:
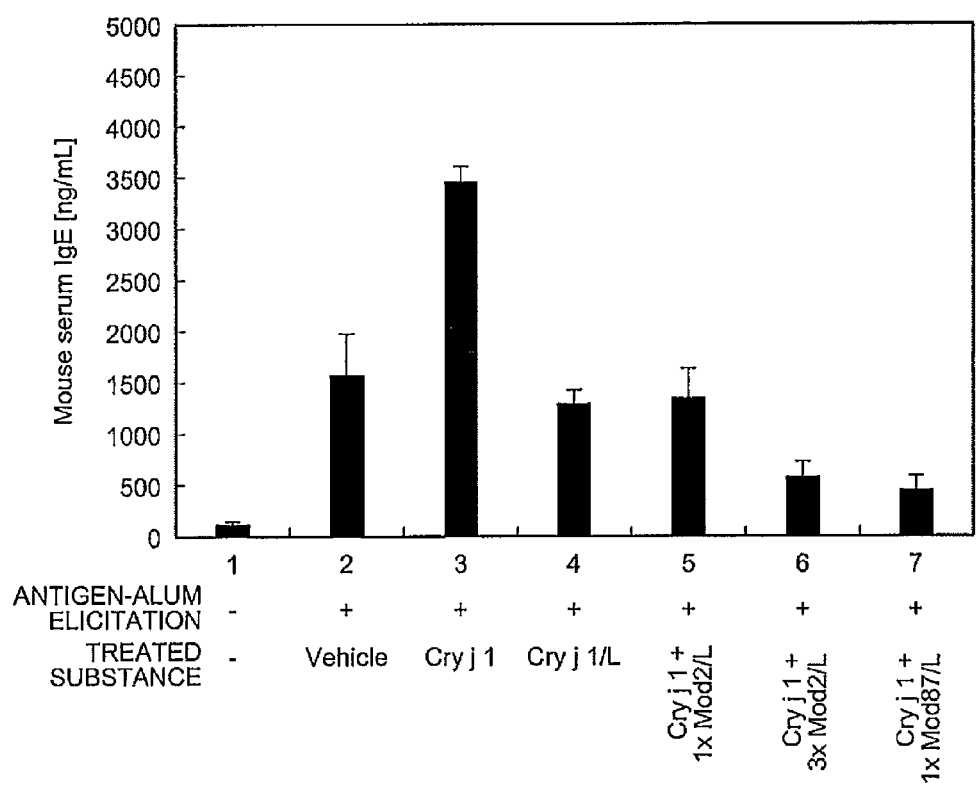
FIG. 11 shows results of measuring the amounts of produced IgE in serum after eliciting the allergy by treating the mice with the immunostimulatory oligonucleotide of the present invention and the publicly known immunostimulatory oligonucleotide together with a cedar pollen antigen Cry j1 in Example 13.

As a result of measuring the amount of IgE in the serum at 6 W, the amounts of IgE in the Cry j1-treated group were twice or more higher than in the Vehicle-treated group. The amounts of IgE in the Cry j1+1×Mod87/L-treated group were the lowest, and became low in the order of Cry j1+3×Mod2/L, Cry j1/L and Cry j1+1×Mod2/L (FIG. 11). Statistic processing (t-test) was performed between the Cry j1+1×Mod2/L-treated group and the Cry j1+1×Mod87/L-treated group. As a result, the amount of produced IgE was significantly low in the Cry j1+1×Mod87/L-treated group (p<0.05).

Figures 1, 12:
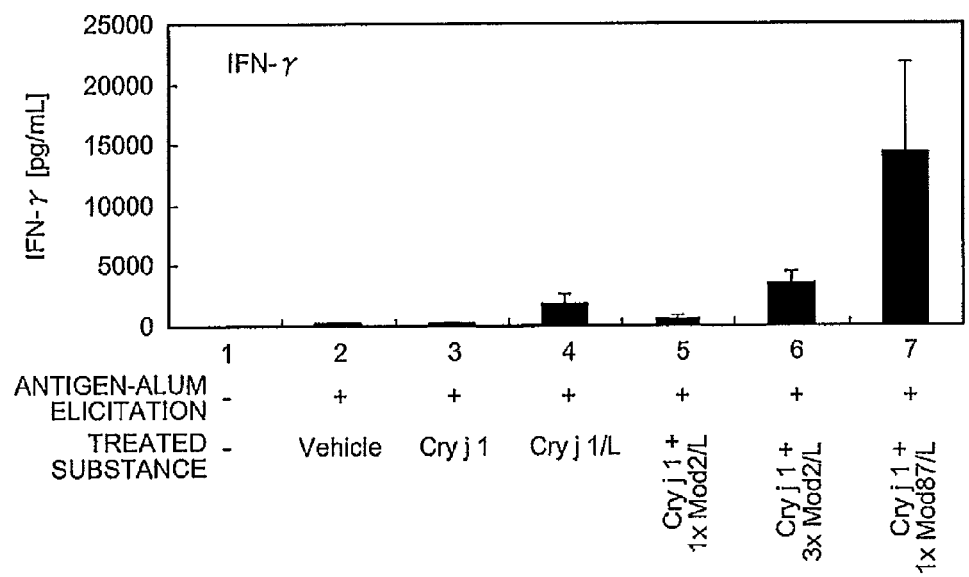
Figures 2, 12:
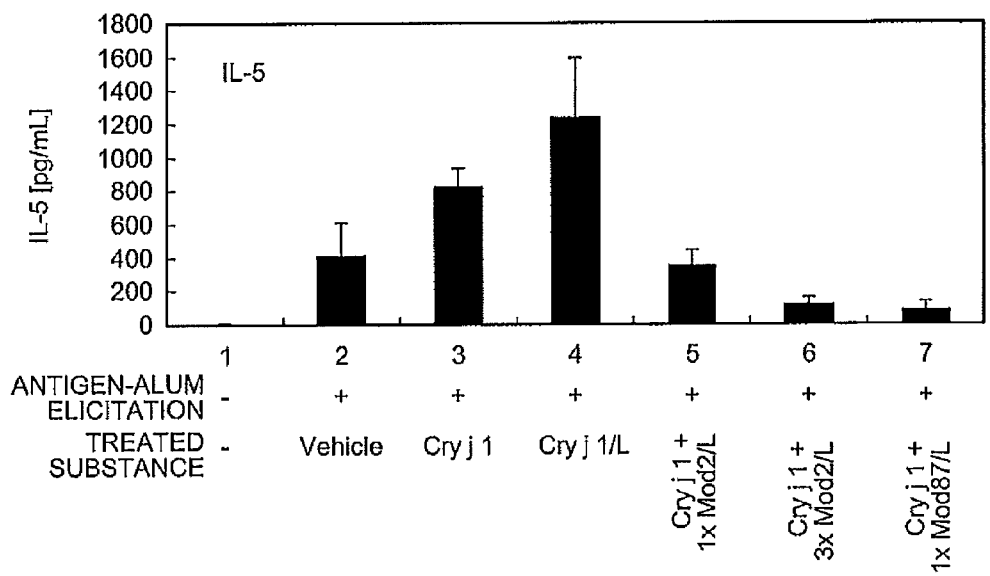

Subsequently, in order to identify the induction of the Th2 response or Th1 response in the mice treated with the subject substance, the spleen was removed from the mice, and the amounts of IL-5 (indicator of Th2 response) and IFN-γ (indicator of Th1 response) produced in the culture supernatant from the splenic cells stimulated with Cry j1 were measured (FIG. 12-1). As a result of measuring the amounts of IFN-γ which was the indicator of Th1 response, the amount was the largest in the Cry j1+1×Mod87/L-treated group (14324.62±7444.07 pg), and next was high in the order of the Cry j1+3×Mod2/L-treated group (3475.30±907.56 pg) and the Cry j1/L-treated group (1782.02±849.23 pg). Although the same amount of the immunostimulatory oligonucleotide as in the Cry j1+1×Mod87/L-treated group was administered, the production of IFN-γ was scarcely observed in the Cry j1+3×Mod2/L-treated group.

Subsequently, the amounts of produced IL-5 were measured. As a result, the production of IL-5 was not suppressed in the Cry j1/L-treated group, but was remarkably decreased by adding the immunostimulatory oligonucleotide. The suppressive activity was the strongest in the Cry j1+1×Mod87/L-treated group. The suppressive activity in the IL-5 production by the liposome complex enclosing the CpG oligonucleotide and Cry j1 was inversely correlated with the IFN-γ-inducing activity, and well-correlated with the suppressive activity in the IgE production. The statistic processing (t-test) was performed between the Cry j1+1×Mod2/1-treated group and the Cry j1+1×Mod87/L-treated group. As a result, the amount of produced IL-5 was significantly lower in the Cry j1+1×Mod87/L-treated group (p<0.05) (FIG. 12-2).

In light of the foregoing, it was found that the liposome enclosing the immunostimulatory oligonucleotide of the present invention and the allergen more strongly suppressed the Th2 response and the IgE production upon exposure to the allergen compared with the allergen technology by the liposome enclosing the publicly known immunostimulatory oligonucleotide and allergen, and potently induced a Th1-inducing activity.

In light of the foregoing, it was shown that the immunostimulatory oligonucleotide of the present invention was useful as a therapeutic or preventive agent for allergic diseases when administered to a patient with an allergic disease, because the immunostimulatory oligonucleotide of the present invention enhanced the activity of suppressing the IgE production, the activity of suppressing the Th2 response and the activity of inducing the Th1 response compared with the publicly known D-type CpG oligonucleotides and had the effective therapeutic effect in a small dose in the allergy model using the animals.

Example 14

Therapeutic Effect on Hepatitis by the Immunostimulatory Oligonucleotide of the Present Invention in Mice Using a concanavalin A (Con A)-induced hepatitis model generally utilized as a murine hepatitis model, the anti-inflammatory effect in vivo of the immunostimulatory oligonucleotide of the present invention was evaluated. The Con A-induced hepatitis model develops hepatitis by eliciting the rapid inflammatory response, and is used as the hepatitis model with activation of the immune response. There is a publicly known example where K-type CpG, 1668 (SEQ ID NO:108) inversely worsened the symptom of hepatitis in the test to evaluate the CpG oligonucleotides in the Con A-induced hepatitis model (Abe et al, Fukushima J. Med. Sci., 51, 41-49, 2005). No report has been disclosed that the immunostimulatory oligonucleotide containing CpG has suppressed the elevation of ALT value which is the marker of hepatitis in the Con A-induced hepatitis model was not reported.

The Con A-induced murine hepatitis model was prepared and the ALT values in the serum were measured as follows.

Female BALB/c mice aged 5 weeks (Charles River Japan Inc.) were used. The mice to be administered with Con A were starved from an evening on the day before the administration to the completion of Con A administration, and feeding was restarted after the Con A administration. The group in which no Con A was administered was made as a Naive group. The immunostimulatory oligonucleotide was administered once 3, 6 or 24 hours before the Con A administration. The immunostimulatory oligonucleotide was prepared at 10 μg/mL with PBS (−), and 100 μL thereof was injected in a tail vein. That is, 1 μg per mouse was administered. Con A was prepared at a concentration of 4 mg/mL using saline as a solvent, and 100 μL thereof was injected in the tail vein of the mouse. That is, 0.4 mg per mouse was administered. A blood sample was collected 24 hours after the Con A administration, and the blood was centrifuged at 10,000 rpm at 4° C. for 5 minutes to obtain the serum. The ALT value in the serum was measured using Fuji Drychem (DRY-CHEM 5500V, FUJIFILM Corporation).

Figure 13:
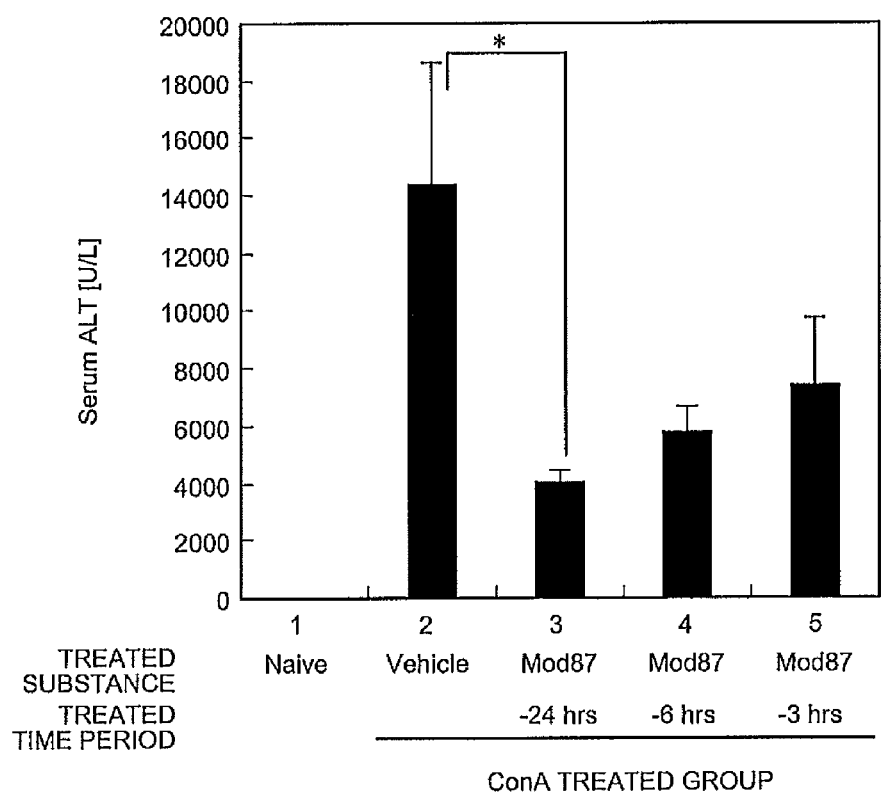
FIG. 13 shows results of evaluating the effect of the immunostimulatory oligonucleotide of the present invention on elevation of ALT levels in serum in a Con-A induced murine hepatitis model in Example 14.

The elevation of ALT values in the serum 24 hours after eliciting the inflammation in the Con A-induced murine hepatitis model was evaluated. As a result (FIG. 13), the immunostimulatory oligonucleotide of Mod87 (SEQ ID NO:52) of the present invention suppressed the elevation of ALT values in the serum depending on treated time periods (Lanes 3 to 5 in FIG. 13). The tendency to suppress the elevation was observed in the treatment before 3 hours (Lane 5). The ALT value in the serum with the treatment before 24 hours was significantly low (Lane 3), and 28.5% of the ALT value of the vehicle group (Lane 2) (t-test, p<0.05).

From the above results, it was demonstrated that the immunostimulatory oligonucleotide of the present invention had the therapeutic effect on hepatitis in vivo.

Example 15

Comparison of Hepatitis Therapeutic Effects by Immunostimulatory Oligonucleotide Mod87 of the Present Invention, with the Effect by 2395, 1018 and 09-GACGATCGTC-G1 (SEQ ID NO:36)

The therapeutic effects on hepatitis using the Con A-induced murine hepatitis model were compared among the oligonucleotide sequence (2395, SEQ ID NO:32) which had the same sequence as pG10101 under the clinical study for chronic hepatitis C and was disclosed in International Publication No. 03/015711 pamphlet and JP 2006-515277, the oligonucleotide sequence (1018, SEQ ID NO:33) disclosed in JP 2003-526662, the oligonucleotide sequence G9-GACGATCGTC-G1 (SEQ ID NO:36) disclosed as the representative sequence having the strong IFN-α-inducing activity in JP 2005-237328-A, and the immunostimulatory oligonucleotide Mod87 (SEQ ID NO:52) of the present invention.

Figures 1, 14:
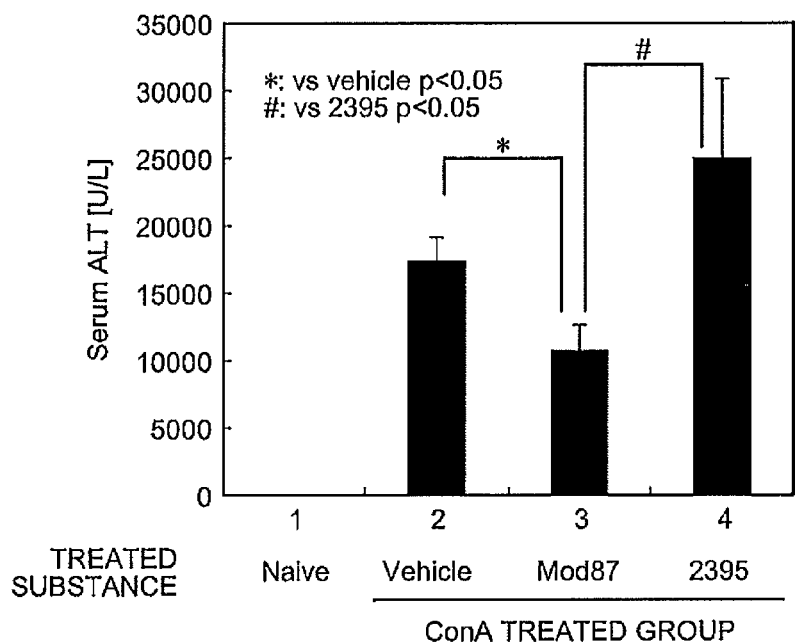
Figures 2, 14:
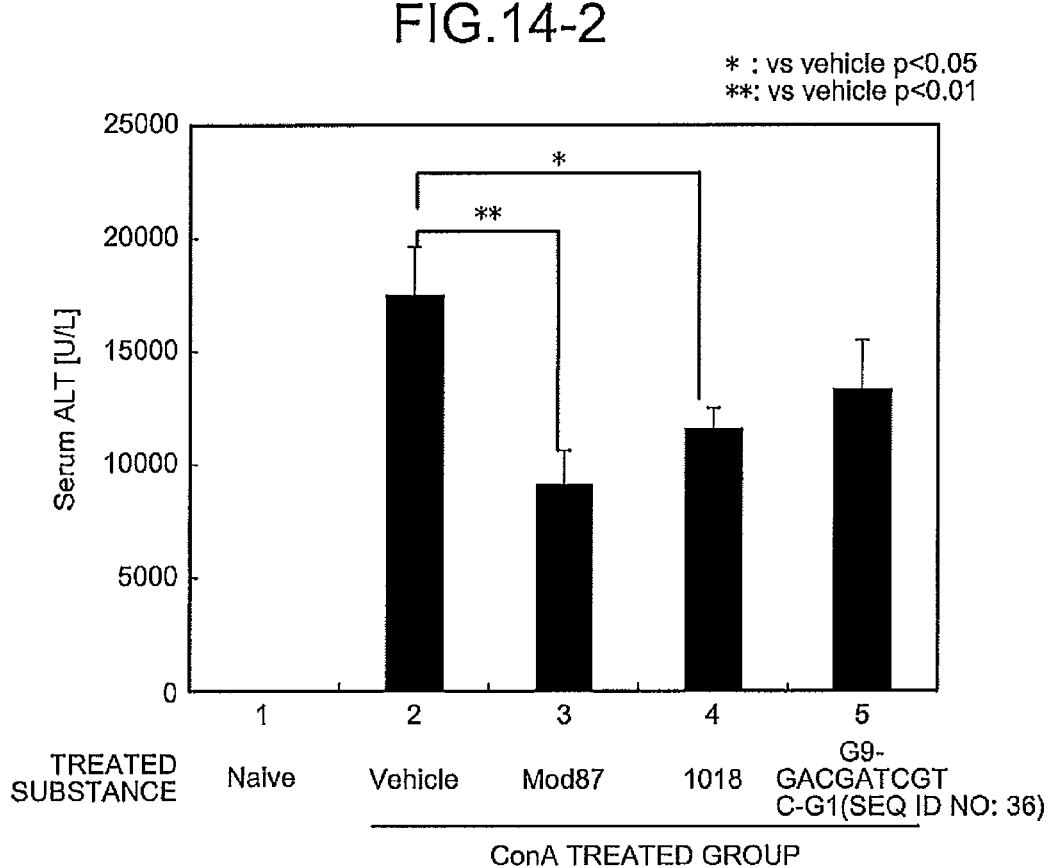

According to the method shown in Example 14, the therapeutic effect of the immunostimulatory oligonucleotides on hepatitis was evaluated by examining a suppression of ALT value elevation in the serum as an indicator. The therapeutic effects of Mod87 and 2395 on hepatitis were compared and evaluated. 1 μg Of the immunostimulatory oligonucleotide was administered to the mouse 6 hours before the Con A administration, and the blood sample was collected 24 hours after eliciting the inflammation with Con A. Then, the ALT value in the serum was measured. As a result, the immunostimulatory oligonucleotide Mod87 of the present invention significantly suppressed the elevation of the ALT value (Lane 3 in FIG. 14-1) (t-test, $p<0.05$), but the oligonucleotide 2395 had no effect at all (Lane 4).

Subsequently, the therapeutic effects of Mod87, 1018 and G9-GACGATCGTC-G1 (SEQ ID NO:36) on hepatitis were compared and evaluated. 1 µg Of the immunostimulatory oligonucleotide was administered to the mouse 24 hours before the Con A administration, and the blood sample was collected 24 hours after eliciting the inflammation with Con A. Then, the ALT value in the serum was measured. As a result, the immunostimulatory oligonucleotide Mod87 of the present invention suppressed the elevation of the ALT value most strongly (Lane 3 in FIG. 14-2), and then 1018 (Lane 4 in FIGS. 14-2) and G9-GACGATCGTC-G1 (SEQ ID NO:36) (Lane 5 in FIG. 14-2) suppressed it in this order. Mod87 and 1018 suppressed the elevation of the ALT value significantly (t-test, Mod87: $p<0.01$, 1018: $p<0.05$). The oligonucleotide G9-GACGATCGTC-G1 (SEQ ID NO:36) did not suppress it significantly.

Therefore, it was demonstrated that the immunostimulatory oligonucleotide of the present invention had a higher therapeutic effect on hepatitis than the publicly known immunostimulatory oligonucleotides having CpG.

By the comparative test in vitro using the human PBMC in Example 6, it has been shown that the immunostimulatory oligonucleotide of the present invention had a stronger activity of suppressing the production of IL-12 than the oligonucleotides having the similar sequences. Thus, it was shown that the anti-inflammatory action in vitro might be correlated with the therapeutic effect on hepatitis in mice.

In light of the foregoing, it was shown that the immunostimulatory oligonucleotide of the present invention had the therapeutic effect on hepatitis in addition to the excellent interferon-inducing activity and the reduced inflammatory cytokine-inducing activity. Thus, it was demonstrated that when administered to a patient with hepatitis C, the immunostimulatory oligonucleotide of the present invention was useful as a therapeutic or preventive agent for hepatitis C.

The invention claimed is:

1. An artificial immunostimulatory oligonucleotide comprising:

the nucleotide sequence represented by the formula:
5'-$(G)_M$PXCGYQ$(G)_N$-3' (SEQ ID NO.: 117) wherein, C is cytosine;

G is guanine;

X and Y are mutually independent and each represent an arbitrary sequence which has a length of 0 to 10 nucleotides and does not contain 4 or more consecutive guanine residues, and the entire length of X+Y is 6 to 20 nucleotides;

XCGY contains a palindrome sequence having a length of at least 8 nucleotides and XCGY has a length of 8 to 22 nucleotides;

P and Q are mutually independent and each represent one nucleotide other than guanine, M represents an integer of 6 to 10, N represents an integer of 0 to 3;

and the length of X and Y may be the same or different, and wherein the length of the artificial immunostimulatory oligonucleotide is 16 to 37 nucleotides in total, wherein the palindrome sequence contains CGATCG (SEQ ID NO: 59), ATCGAT (SEQ ID NO: 60), or GACGTC (SEQ ID NO: 61), but the artificial immunostimulatory nucleotide is not SEQ ID NO:5 GGGGGGTGCCGATCGGCAGGG.

2. The artificial immunostimulatory oligonucleotide according to claim 1, wherein the M represents the integer of 6 to 8 and the total length of said artificial immunostimulatory oligonucleotide is 16 to 35 nucleotides.

3. The artificial immunostimulatory oligonucleotide according to claim 1, wherein the XCGY has a length of 9 or 10 nucleotides and the total length of said artificial immunostimulatory oligonucleotide is 17 to 23 nucleotides.

4. The artificial immunostimulatory oligonucleotide according to claim 1, wherein the nucleotide sequence of the artificial immunostimulatory oligonucleotide consists of the nucleotide sequence of SEQ ID NO:30.

5. The artificial immunostimulatory oligonucleotide according to claim 1, wherein a phosphodiester linkage at all or a part of internucleotides is modified with phosphorothioate.

6. The artificial immunostimulatory oligonucleotide according to claim 5, wherein the phosphodiester linkage of at least a part of internucleotides, in a consecutive G sequence at the 5' terminus is modified with phosphorothioate.

7. The artificial immunostimulatory oligonucleotide according to claim 5, wherein the phosphodiester linkage of at least a part of internucleotides, at the 3' terminus is modified with phosphorothioate.

8. A pharmaceutical containing the artificial immunostimulatory oligonucleotide according to claim 1 as an active ingredient.

9. A therapeutic agent for an allergic disease containing the artificial immunostimulatory oligonucleotide according to claim 1 and an allergen as active ingredients.

10. The therapeutic agent for the allergic disease according to claim 9, wherein said allergic disease is a pollen allergic disease and said allergen is a pollen allergen.

11. An immunological adjuvant containing the artificial immunostimulatory oligonucleotide according to claim 1.

12. A therapeutic agent for hepatitis containing the artificial immunostimulatory oligonucleotide according to claim 1 as an active ingredient.

13. The therapeutic agent for hepatitis according to claim 12, wherein the hepatitis is viral hepatitis.

14. The therapeutic agent for hepatitis according to claim 13, wherein the viral hepatitis is hepatitis B or hepatitis C.

15. An interferon-alpha inducing agent containing the artificial immunostimulatory oligonucleotide according to claim 1.

16. The artificial immunostimulatory oligonucleotide according to claim 1, wherein the nucleotide sequence of the artificial immunostimulatory oligonucleotide is a nucleotide sequence selected from the group consisting of SEQ ID NOs: 7, 17, 28, 40, 42, and 52.

* * * * *